(12) United States Patent
Joseph et al.

(10) Patent No.: US 6,593,342 B1
(45) Date of Patent: Jul. 15, 2003

(54) PHARMACEUTICAL COMPOSITIONS COMPRISING 2-QUINOLONES

(75) Inventors: Benoît Joseph, Orleans Cedex 2 (FR); Francis Darro, Brussels (BE); Gérald Guillaumet, Orleans Cedex 2 (FR); Robert Kiss, Brussels (BE); Armand Frydman, Maisons Alfort (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/743,766

(22) PCT Filed: Jul. 13, 1999

(86) PCT No.: PCT/FR99/01716
§ 371 (c)(1),
(2), (4) Date: Jan. 16, 2001

(87) PCT Pub. No.: WO00/03990
PCT Pub. Date: Jan. 27, 2000

(30) Foreign Application Priority Data

Jul. 15, 1998 (FR) .............................. 98 09060

(51) Int. Cl.⁷ ...................... A61K 31/47; C07D 215/16; C07D 215/20
(52) U.S. Cl. ........................ 514/312; 546/157; 546/158
(58) Field of Search .......................... 514/312; 546/157, 546/158

(56) References Cited

U.S. PATENT DOCUMENTS 5,614,532 A * 3/1997 Carling ........................ 514/312
5,726,184 A   3/1998 Zelle

FOREIGN PATENT DOCUMENTS

| EP | 0 024 638 A1 | 3/1981 |
| JP | 49-75877 * | 7/1974 |
| WO | WO 93/11115 | 6/1993 |
| WO | WO 94/02145 | 2/1994 |
| WO | 95/23145 * | 8/1995 |
| WO | WO 9523145 * | 8/1995 |

OTHER PUBLICATIONS

CA 62:36734, abstract of Sampei, Sankyo Kenkyusho Nempo, 16, pp. 42–48, 1964.*
CA 78:43231, Abstract of Pharm Inst, Tohoku Univ, Sendai Japan, Kametani, 1972.*
CA 90:54787, abstract of Indian J Chem, Sect B, 1978, 16B(8), pp 744–745, Roy.*
CA 92:128694, abstract of Indian J Chem, Sect B, 1979, 18B(4), 324–330, Manimaran.*
CA 102:6125, Abstract of Indian J Chem, Sect B, 1984, 23B(8), 720–727, Natarajan.*
CA 120:244601, abstract of Heterocycles, 1993, 36(10), 2315–2325, Alonso.*
CA 124:117055, abstract of Liebigs Ann, 1995, (10), 1895–1899, Ferrer.*
CA 126:251058, abstract of J Chem Soc, Perkin Trans 1, 1997, (3), 229–233, Lopez–Alvarado.*
CA 127:34101, abstract of Heterocycles, 1997, 45(4), 683–690, Croisy.*
Abstract: XP–002095829, vol. 82, No. 3 (1975).

* cited by examiner

Primary Examiner—D. Margaret Seaman
(74) Attorney, Agent, or Firm—Jacobson Holman PLLC

(57) ABSTRACT

The invention concerns a pharmaceutical composition having an activity on the proliferation of clonogenic cells in tumours and comprising an efficient amount of a compound selected among the compounds of formulae (I) and (Ia) wherein: X, $R_1$, $R_2$, $R_3$, $R_4$, $R_5$, $R_6$ are as defined in claim 1.

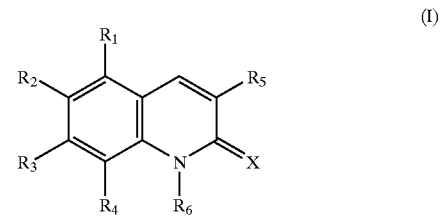

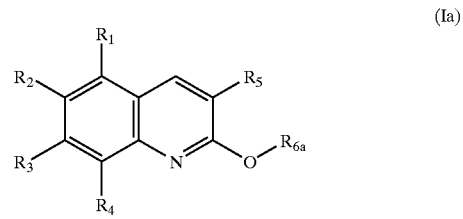

22 Claims, No Drawings

PHARMACEUTICAL COMPOSITIONS COMPRISING 2-QUINOLONES

This application is a 371 of PCT/FR99/01716, filed Jul. 13, 1999.

The present invention relates to pharmaceutical compositions comprising 2-quinolones or derivative compounds.

A cancer is a disorder of the somatic genes in the course of which genetic dysfunctions are amplified as the tumoral process progresses from the state of precancerous lesion to that of malignant transformation, the cancer tumor becoming metastatic and often resistant to cytotoxic medicines.

Despite the very considerable efforts made in all the developed countries, in particular through experimental and clinical research programs, mortality due to various cancers (solid tumors and hematological neoplasties) remains unacceptably high. In many countries, cancer is the second most common cause of death, just after cardiovascular diseases.

In terms of newly diagnosed cancers, the distribution between solid tumors and hematological neoplasties (bone marrow, blood, lymphatic system) shows that 9 out of 10 cancers are solid tumors. In contrast with what is observed in hematological oncology (therapeutic successes in 40% to 90% of cancers of blood cells), only a small number of advanced or disseminated solid tumors respond to chemotherapy treatments alone. It is partly for this reason that the overall death by cancer grew in the USA between 1973 and 1992.

Unfortunately, it is not certain that this tendency may be reversed merely by the appearance, alongside the established chemotherapy arsenal, of new antitumor medicines such as taxanes (paclitaxel and docetaxel) which interfere with the formation of microtubules (W. P. McGuire et al., Am. Intern. Med., 1989), topoisomerase I inhibitors derived from camptothecin (topotecan and irinotecan), vinorelbine (novel alkaloid derived from periwinkle), gemcitabine (novel cytotoxic antimetabolite), raltitrexed (thymidylate synthetase inhibitor) and miltefosine (first representative of the alkyl-lysophospholipid family). These treatments are added, either as a first line treatment or as a second line treatment, to medicines whose specific activity is now well recognized, such as doxorubicin, cysplatin, vincristine, methotrexate and 5-fluorouracil.

One of the most difficult current problems in anticancer chemotherapy is due to the fact that many populations of malignant cells show considerable resistance to the established cytotoxic substances. Usually, this situation results from the existence of multi-drug-resistance genes or from the frequency of genetic mutations in certain types of tumors. Thus, the treatment of cancers requires novel approaches, complementary to those currently used, and designed to better combat the extension and heterogeneity of the tumor load and the acquisition of "cytotoxic multidrug" resistance.

Among these novel approaches, some are already promising. This is the case for the induction of apoptosis, the inhibition of tumor angiogenesis and of metastatic processes, not to mention gene therapy or immunotherapy.

The inventors have become interested in a different approach. The desired objective was to make the population of tumor cells more sensitive to the standard anticancer treatments in order to achieve a twofold benefit:

1) to increase the cytotoxic activity and thus the efficacy, and
2) to reduce the frequency and severity of certain side effects by means of reducing the dosage which might follow the induction of the increase in the antitumor efficacy.

It is this strategy which underlies the discovery of compositions capable of inducing a highly significant increase in the cytotoxic activity of tested anticancer medicines. These compositions have the capacity either of stimulating the recruitment of clonogenic cells in the tumor, thus making it more sensitive to the conventional treatment with cytotoxic agents, or of inhibiting the proliferation of clonogenic cells, thus contributing toward the regression of the tumor.

A subject of the present invention is thus the use, in the treatment of cancers with at least one antitumor agent chosen from cytotoxic agents, of a compound having activity on the proliferation of clonogenic cells in tumors, chosen from the compounds of formulae:

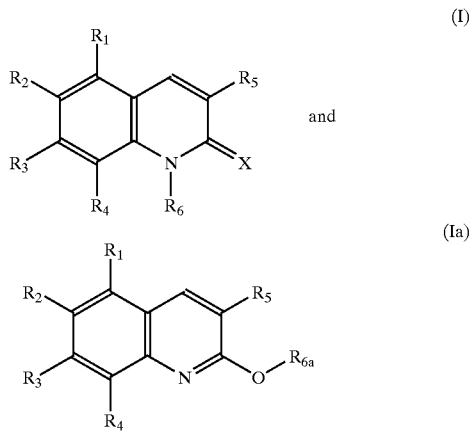

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —OCOR$_8$, a phenyl ($C_1$–$C_4$ alkoxy) group, a group —O—SO$_2$—R'$_8$, R'$_8$ being a $C_1$–$C_4$ alkyl group or a CF$_3$ group, and a group derived from a saccharide, $R_6$ is chosen from H, a $C_1$–$C_4$ alkyl group, a group —CO—$R_9$ and a group —A—$R_{10}$, $R_{6a}$ is chosen from a $C_1$–$C_4$ alkyl group, a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —COOR$_{11}$, —CONR$_{12}$R$_{13}$, a group —NR$_{14}$R$_{15}$ and a group —COR$_{16}$, R$_{11}$, R$_{12}$, R$_{13}$, R$_{14}$, R$_{15}$ and R$_{16}$ being chosen independently from a hydrogen atom, a $C_1$–$C_4$ alkyl group and a phenyl($C_1$–$C_4$ alkyl) group, $R_4$ and $R_6$ together also possibly forming a —CO—CH$_2$—CH$_2$— group.

The cytotoxic agents may be used at their usual dose and, in this case, their efficacy is improved, or at lower doses given the increase in their antitumor efficacy.

In one preferred embodiment, the compound used is a compound of formula (I) in which:

$R_1$ is a $C_1$–$C_4$ alkoxy group
$R_2$ is a hydrogen atom
$R_3$ is a $C_1$–$C_4$ alkoxy group
$R_4$ is a hydrogen atom, and in particular a compound of formula (I) in which:

$R_5$ is a 4-($C_1$–$C_4$ alkoxy)phenyl group, and most particularly a compound of formula (I) in which:

$R_1$ is a methoxy group,
$R_3$ is a methoxy group, and
$R_5$ is a 4-methoxyphenyl group.

It has also been discovered that at least some of the compounds of formula (I) had antitumor activity themselves.

A subject of the present invention is also a composition having activity on the proliferation of clonogenic cells in tumors by interfering with the generation of clonogenic cells, either by stimulating proliferation and recruitment, or by inhibiting proliferation, and which comprises an effective amount of a compound of formulae:

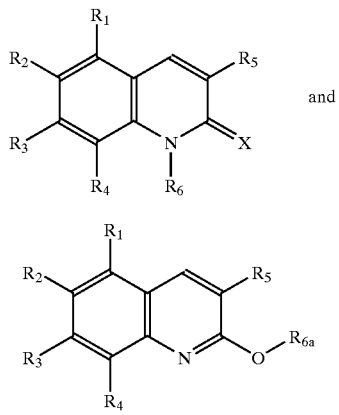

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —OCOR$_8$, a phenyl ($C_1$–$C_4$ alkoxy) group, a group —O—$SO_2$—R'$_8$, R'$_8$ being a $C_1$–$C_4$ alkyl group or a $CF_3$ group, and a group derived from a saccharide, $R_6$ is chosen from H, a $C_1$–$C_4$ alkyl group, a group —CO—$R_9$ and a group —A—$R_{10}$, $R_{6a}$ is chosen from a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —COOR$_{11}$, —CONR$_{12}$R$_{13}$, a group —NR$_{14}$R$_{15}$ and a group —COR$_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl($C_1$–$C_4$ alkyl) group, $R_4$ and $R_6$ together also possibly forming a —CO—$CH_2$—$CH_2$— group.

A subject of the present invention is also novel compounds, namely compounds of formulae:

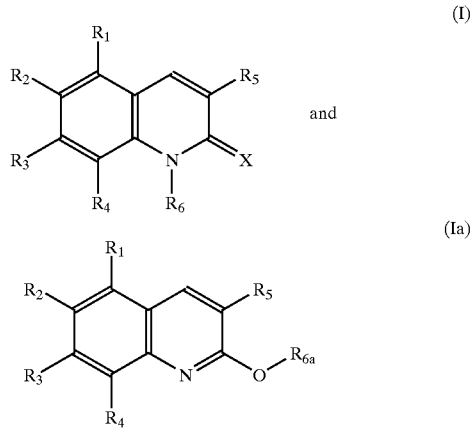

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —OCOR$_8$, a phenyl ($C_1$–$C_4$ alkoxy) group, a group —O—$SO_2$—R'$_8$, R'$_8$ being a $C_1$–$C_4$ alkyl group or a $CF_3$ group, and a group derived from a saccharide, $R_6$ is chosen from H, a $C_1$–$C_4$ alkyl group, a group —CO—$R_9$ and a group —A—$R_{10}$, $R_{6a}$ is chosen from a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —COOR$_{11}$, —CONR$_{12}$R$_{13}$, a group —NR$_{14}$R$_{15}$ and a group —COR$_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl($C_1$–$C_4$ alkyl) group, $R_4$ and $R_6$ together also possibly forming a —CO—$CH_2$—$CH_2$— group, with the exclusion of the compounds in which X=O, $R_6$=H and two of the substituents $R_1$, $R_2$, $R_3$ and $R_4$ are OH or $OCH_3$.

In the chemotherapy treatment of cancers with cytotoxic agents, the compounds of formulae (I) and (Ia) can be administered at the start of the chemotherapy treatments either once or over several days at the start of these treatments (for example for 5 to 7 days) and, depending on the chemotherapy protocol, at the start of each treatment cycle (for example for 2 to 5 days) in the course of each cure.

The compounds of formulae (I) and (Ia) are advantageously administered by infusion (generally in 1 to 3 hours) at doses of from 5 to 50 mg/kg/day or 200 to 2000 mg/m$^2$/day.

In order to obtain a maximal effect on the production (inhibition or stimulation) of clonogenic cells, the compounds of formulae (I) and (Ia) should be administered such that the tissue concentrations obtained are as high as can possibly be envisaged.

For the treatment protocols in the acute phases of the cures, the intravenous route is preferred, using:

ready-to-use infusion solutions (bags, bottles, etc.) intended to be administered without any modification, by intravenous infusion using an infusion line and at the recommended rate:

lyophilizates to be redissolved for intravenous infusion using pharmaceutical solutions known to those skilled in the art;

for maintenance treatments, it is also possible to envisage the oral route when the chemotherapy treatment favors the oral administration of cytostatic agents. To this end, lozenges (for oral or perlingual absorption), immediate-release or delayed-release tablets, oral solutions, suspensions, granules, gel capsules, etc. may be used.

The cytotoxic agents may be chosen from:
i) intercalating agents, in particular doxorubicin (Adriamycin), daunorubicin, epirubicin, idarubicin, zorubicin, aclarubicin, pirarubicin, acridine, mitoxanthrone, actinomycin D, eptilinium acetate;
ii) alkylating agents chosen from platinum derivatives (cisplatin, carboplatin, oxaliplatin);
iii) a compound chosen from the other groups of alkylating agents:

cyclophosphamide, ifosfamide, chlormetrine, melphalan, chlorambucil, estramustine, busulfan, mitomycin C, nitrosoureas: BCNU (carmustine), CCNU (lomustine), fotemustine, streptozotocin, triazines or derivatives: procarbazine, dacarbazine, pipobroman, ethyleneimines: altretamine, triethylene-thio-phosphoramide, iv) a compound chosen from the other groups of anti-metabolic agents:

antifolic agents: methotrexate, raltitrexed, antipyrimidine agents: 5-fluorouracil (5-FU), cytarabine (Ara-C), hydroxyurea antipurine agents: purinethol, thioguanine, pentostatin, cladribine, cytotoxic nucleoside synthesis inducers: gemcitabine, v) a compound chosen from the other groups of tubulin-affinity agents, vinca alkaloids which disrupt the mitotic spindle: vincristine, vinblastine, vindesine, navelbine, agents which block the depolymerization of the mitotic spindle: paclitaxel, docetaxel, agents which induce DNA cleavage by inhibition of topoisomerase II: etoposide, teniposide, topoisomerase I inhibitors which induce DNA cleavage: topotecan, irinotecan, vi) a DNA splitting or fragmenting agent, such as bleomycin, vii) one of the following compounds: plicamycin, L-asparaginase, mitoguazone, dacarbazine, viii) an anticancer progestative steroid; medroxy-progesterone, megestrol, ix) an anticancer estrogen steroid: diethylstilbestrol; tetra-sodium fosfestrol, x) an antiestrogen agent: tamoxifen, droloxifen, raloxifen, aminoglutethimide, xi) a steroidal antiandrogenic agent (eg cyproterone) or a non-steroidal antiandrogenic agent (flutamide, nilutamide).

In particular, the compounds of formulae (I) and (Ia) may be combined with all the major treatments with cytotoxic agents used in solid tumor polychemotherapies, such as:

doxorubicin alkylating agents: oxazophorines (cyclophosphamide, ifosfamide, chlorambucil, melphalan)

nitrosoureas mitomycin C antimetabolites such as methotrexate, 5-FU, Ara-C, capecitabine agents which interfere with tubulin: vinca alkaloids (vincristine, vinblastine, vindesine, navelbine), taxoids (paclitaxel, docetaxel), epipodophyllotoxin derivatives (etoposide, teniposide)

bleomycin topoisomerase I inhibitors: topotecan, irinotecan.

Similarly, the compounds of formulae (I) and (Ia) may be combined with the treatments with the major cytotoxic agents used in oncohematology for the treatment of blood cancers:

Hodgkin's disease: cyclophosphamide, mechlorethamine, chlorambucil, melphalan, ifosfamide, etoposide, doxorubicin, daunorubicin;

acute leukemias: methotrexate, 6-mercaptopurine, cytarabine, vinblastine, vincristine, doxorubicin, daunorubicin, L-asparaginase;

non-Hodgkin's malignant lymphomas: mechlorethamine, chlorambucil, cyclophosphamide, melphalan, ifosfamide, methotrexate, cytarabine, vinblastine, vincristine, etoposide, doxorubicin, daunorubicin, carmustine, lomustine, cisplatin;

chronic lymphoid leukemias: mechlorethamine, chlorambucil, cyclophosphamide, melphalan, ifosfamide.

In general, the compounds of formula (I) may be prepared according to the following reaction schemes:

SCHEME I

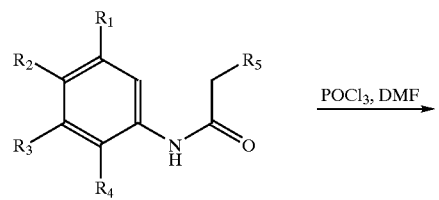

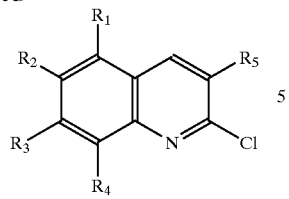

↓ AcOH, H₂O

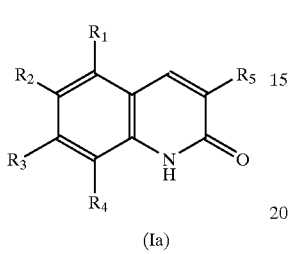

(Ia)

SCHEME II

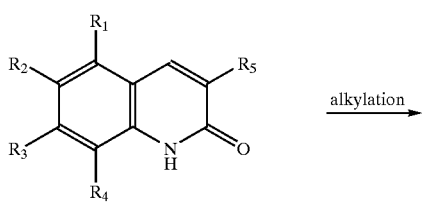

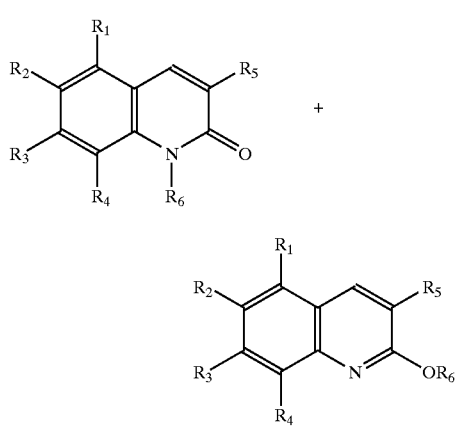

A reagent of the type XR₆ in which X=I, Br or Cl may be used as alkylating agent.

As a variant, a compound CH₂=CH—R can be used to attach a group R₆=—CH₂—CH₂—R (corresponding to the group —A—R₁₀ defined above).

SCHEME III

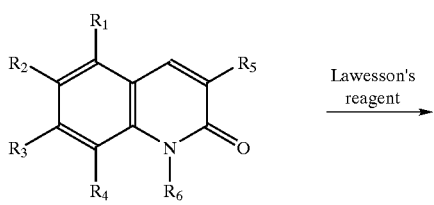

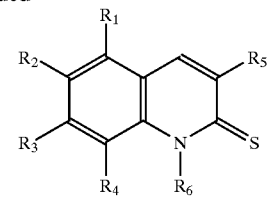

SCHEME IV

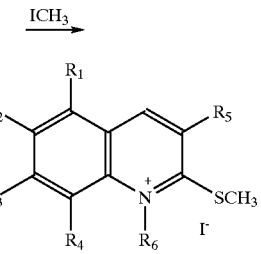

↓ ICH₃

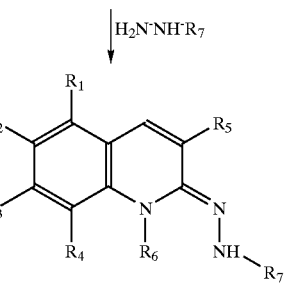

↓ H₂N-NH-R₇

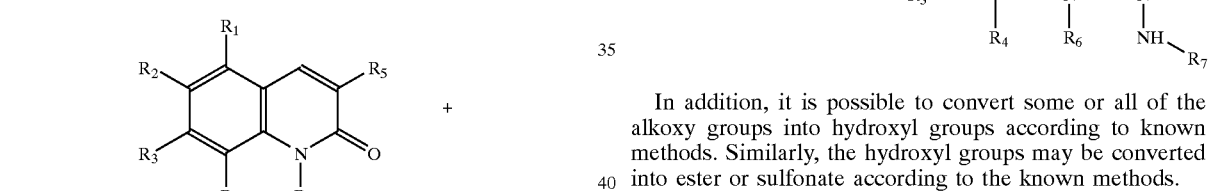

In addition, it is possible to convert some or all of the alkoxy groups into hydroxyl groups according to known methods. Similarly, the hydroxyl groups may be converted into ester or sulfonate according to the known methods.

Similarly, it is possible to convert a group —A—COOR₁₁, in which R₁₁ is an alkyl or phenylalkyl group, into a group —A—COOH and to convert a group —A—COOH into a group —A—CONR₁₂R₁₃, according to known methods.

The compounds in which R₄ and R₆ form a —CO—CH₂—CH₂— group can be obtained by cyclization of a compound in which R₄=H and R₆=—CH₂—CH₂—COOH.

EXAMPLE 1

5,7-Dimethoxy-3-(4-methoxhphenyl)-1,2-dihydro-2-quinolinone (Compound 1)

a) N-(3,5-Dimethoxyphenyl)-2-(4-methoxyphenyl)acetamide (Compound 2)

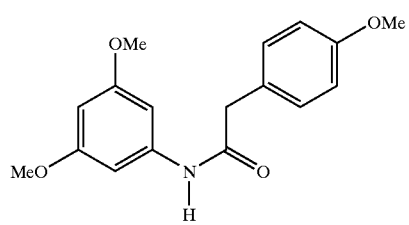

500 mg (3.3 mmol) of 3,5-dimethoxyaniline are dissolved in toluene (7 ml) at 0° C., under a nitrogen atmosphere. A solution of 4-methoxyphenylacetyl chloride (0.5 ml, 3.3 mmol) in 5 ml of toluene is added dropwise to the medium. The reaction mixture is stirred at room temperature for 1 h and the medium is then hydrolyzed with cold sodium hydrogen carbonate solution. The two-phase system is stirred vigorously for 30 min and the organic phase is then collected. The aqueous phase is-extracted with ethyl acetate (twice). The organic phase is dried over MgSO$_4$ and then evaporated. The residue obtained is crystallized from petroleum ether to give 810 mg (82%) of compound 2.

m.p. 135–137° C. (toluene); IR (KBr) n 3292, 1658, 1615 cm$^{-1}$; $^1$H NMR (250 MHz, CDCl$_3$): d 3.66 (s, 2H, CH$_2$), 3.74 (s, 6H, OCH$_3$), 3.82 (s, 3H, OCH$_3$), 6.20 (t, 1H, J=2.2 Hz, H$_{Ar}$), 6.62–6.66 (m, 2H, H$_{Ar}$), 6.95 (d, 2H, J=7.5 Hz, H$_{Ar}$), (broad s, 1H, NH), 7.23 (d, 2H, J=7.5 Hz, H$_{AR}$). $^{13}$C NMR (62.90 MHz, CDCl$_3$): d 44.0, 55.3, 55.4 (2), 96.7, 97.9 (2), 114.4 (2), 126.2, 130.7 (2), 139.4, 159.0, 161.0 (2), 169.5. MS (ionspray): 302 (M+1)$^+$.

b) 2-Chloro-5,7-dimethoxy-3-(4-methoxyphenyl)-1, 2-dihydroquinoline (Compound 3)

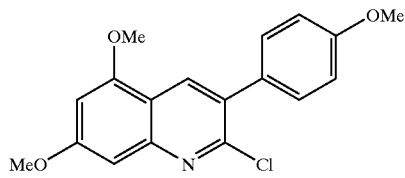

0.31 ml (4.0 mmol, 1.5 eq) of N,N-dimethyl-formamide is added dropwise to 1.75 ml (20.0 mmol, 7.5 eq) of POCl$_3$, under a nitrogen atmosphere and at −30° C. The medium is stirred for 15 min at −30° C., followed by addition of 810 mg of amide 2 (2.7 mmol). The reaction mixture is warmed to room temperature with stirring and is then heated at 75° C. for 2.5 h. At the end of the reaction, this solution is poured onto crushed ice, neutralized with 30% aqueous ammonia solution and then extracted with dichloromethane. The organic phase is dried over MgSO$_4$ and then evaporated. The residue obtained is purified by chromatography on a column of silica (eluent: 3/7 EtOAc/PE) to give 270 mg (30%) of compound 3.

m.p. 156–157° C. (toluene); $^1$H NMR (250 MHz, CDCl$_3$): d 3.87 (s, 3H, OCH$_3$), 3.93 (s, 3H, OCH$_3$), 3.95 (s, 3H, OCH$_3$), 6.52 (d, 1H, J=2.0 Hz, H$_{Ar}$), 6.97–7.01 (m, 3H, H$_{Ar}$), 6.95 (d, 2H, J=8.7 Hz, H$_{Ar}$), 8.35 (s, 1H, H$_{Ar}$). $^{13}$C NMR (62.9 MHz, CDCl$_3$): d 55.3, 55.7, 55.8, 98.6, 98.9, 113.6 (2), 115.8, 125.9, 130.5, 131.0 (2), 133.8, 149.0, 150.5, 156.0, 159.4, 162.1. MS (ionspray): m/z 330 (M+1)$^+$, 332 (M+3)$^+$.

c) 5,7-Dimethoxy-3-(4-methoxyphenyl)-1,2-dihydro-2-quinolinone (Compound 1)

(CRL8246)

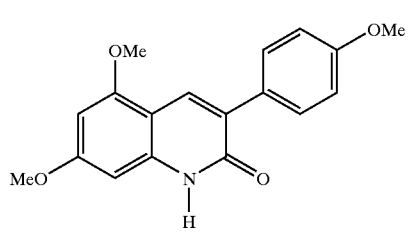

Compound 3 (250 mg, 0.76 mmol) dissolved in acetic acid (1.2 ml, 26.25 mmol per mmol of 3) and water (0.04 ml, 2.77 mmol per mmol of 3) is refluxed for 3 h. The acetic acid is evaporated off. The residue obtained is taken up in water, neutralized with 25% sodium hydroxide solution and finally extracted with dichloromethane. The organic phase is dried over MgSO$_4$ and then evaporated under reduced pressure. The residue is taken up in ethyl acetate, this operation bringing about crystallization of the final product. The crystals thus obtained are filtered off to give 200 mg (85%) of compound 1.

The overall yield for the synthesis carried out to obtain compound 1 is 21%.

m.p. 254–255° C. (EtOAc); IR (KBr) n 1664, 1628, 1573, 1518 cm$^{-1}$; $^1$H NMR (250 MHz, DMSO-d$_6$): d 3.78 (s, 3H, OCH$_3$), 3.81 (s, 3H, OCH$_3$), 3.89 (s, 3H, OCH$_3$), 6.35 (d, 1H, J=2.0 Hz, H$_{Ar}$), 6.45 (d, 1H, J=2.0 Hz, H$_{Ar}$), 6.95 (d, 2H, J=7.5 Hz, H$_{Ar}$), 7.66 (d, 2H, J=7.5 Hz, H$_{Ar}$), 7.96 (s, 1H, H$_{Ar}$), 11.76 (broad s, 1H, NH). $^{13}$C NMR (62.90 MHz, DMSO=d$_6$): d 55.1, 55.4, 55.9, 90.0, 93.0, 104.6, 113.3 (2), 126.5, 129.0, 129.6 (2), 130.2, 140.5, 156.6, 158.7, 161.5, 161.9. MS (ionspray): m/z 312 (M+1)$^+$; Anal. calculated for C$_{18}$H$_{17}$NO$_4$: C, 69.44; H, 5.50; N, 4.50. Found: C, 69.29; H, 5.40; N, 4.55.

EXAMPLE 2

5,7-Dimethoxy-3-(4-hydroxyphenyl)-1,2-dihydro-2-quinolinone (Compound 4)

(CRL8284)

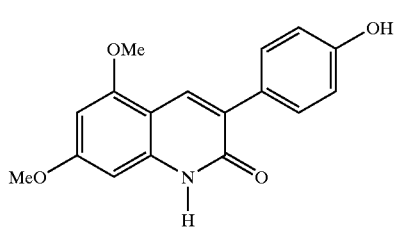

530 mg (1.70 mmol) of compound 1 are dissolved in 15 ml of acetic acid, under an inert atmosphere. A commercial solution of 48% HBr in water (2.65 ml) is added dropwise (exothermic reaction) to the reaction mixture. The final solution is refluxed with stirring for 5 h. After cooling, the reaction is diluted by addition of water and is then neutralized with 10% sodium hydroxide solution (pH=6–7). The product is extracted with dichloromethane (twice). The organic phase is dried over MgSO$_4$ and then evaporated under reduced pressure. The residue is purified by chromatography on a column of silica (eluent: 9/1 CH$_2$Cl$_2$/MeOH) to give 175 mg (35%) of compound 4.

m.p. 275–276° C. (EtOAc); IR (KBr) n 1628, 1604, 1558, 1518 cm$^{-1}$; $^1$H NMR (250 MHz, DMSO-d$_6$): d 3.80 (s, 3H, OCH$_3$), 3.89 (s, 3H, OCH$_3$), 6.35 (d, 1H, J=2.5 Hz, H$_{Ar}$), 6.43 (d, 1H, J=2.5 Hz, H$_{Ar}$), 6.78 (d, 2H, J=7.5 Hz, H$_{Ar}$), 7.55 (d, 2H, J=7.5 Hz, H$_{Ar}$), 7.92 (s, 1H, H$_{Ar}$), 9.48 (s, 1H, OH), 11.72 (broad s, 1H, NH); $^{13}$C NMR (62.90 MHz, DMSO-d$_6$): d 55.4, 55.9, 90.0, 93.0, 104.7, 114.8 (2), 126.9, 127.4, 129.6, 129.8 (2), 140.4, 156.6, 156.9, 161.6, 161.8; MS (ionspray): m/z 298 (M+1)$^+$; Anal. calculated for C$_{17}$H$_{15}$NO$_4$: C, 68.68; H, 5.09; N, 4.71. Found: C, 68.90; H, 5.09; N, 4.90.

EXAMPLE 3

5,7-Dihydroxy-3-(4-hydroxyphenyl)-1,2-dihydro-2-quinolinone (Compound 5)

(CRL8311)

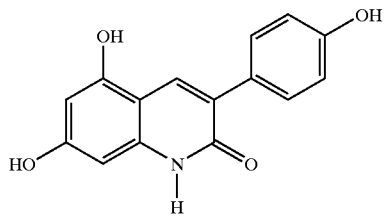

1.0 g (3.2 mmol) of compound 1 is dissolved in 15 ml of acetic acid, under an inert atmosphere. A commercial solution of 48% HBr in water (5 ml) is added dropwise (exothermic reaction) to the reaction mixture. The final solution is refluxed with stirring for 3 days. After cooling, the reaction is diluted by addition of water and is then neutralized with 10% sodium hydroxide solution (pH=6–7). The product is extracted with dichloromethane (twice). The organic phase is dried over $MgSO_4$ and then evaporated under reduced pressure. The residue obtained is purified by chromatography on a column of silica (eluent: 9/1 $CH_2Cl_2$/MeOH) to give 320 mg (37%) of compound 5.

m.p. >280° C. $^1$H NMR (250 MHz, DMSO-$d_6$): d 6.11 (d, 1H, J=2.0 Hz, $H_{Ar}$), 6.18 (d, 1H, J=2.0 Hz, $H_{Ar}$), 6.76 (d, 2H, J=8.6 Hz, $H_{Ar}$), 7.52 (d, 2H, J=8.6 Hz, $H_{Ar}$), 7.89 (s, 1H, $H_{Ar}$), 9.42 (s, 1H, OH), 9.84 (s, 1H, OH), 10.21 (s, 1H, OH), 11.46 (broad s, 1H, NH). $^{13}$C NMR (62.90 MHz, DMSO-$d_6$): d 91.3, 96.4, 103.5, 114.7 (2), 125.1, 127.8, 129.4 (2), 130.4, 140.7, 155.3, 156.6, 160.1, 161.8. MS (ionspray): m/z 270 (M+1)$^+$; Anal. calculated for $C_{15}H_{11}NO_4$: C, 66.91; H, 4.12; N, 5.20. Found: C, 66.80; H, 4.00; N, 5.40.

EXAMPLE 4

5,7-Dimethoxy-3-(4-methoxhphenyl)-1,2-dihydro-2-quinolinethione (Compound 6)

(CRL8271)

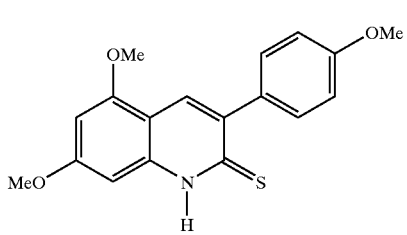

100 mg (0.32 mmol) of compound 1 are dissolved in 15 ml of toluene (hot dissolution), under an inert atmosphere. 260 mg (0.64 mmol, 2 eq) of Lawesson's reagent are added to the reaction mixture. The final solution is refluxed for 18 h. After cooling, the toluene is evaporated off. The residue obtained is purified by chromatography on a column of silica (eluent: 9/1 $CH_2Cl_2$/EtOAc) to give 81 mg (77%) of compound 6.

m.p. 229–230° C. (Et$_2$O); IR (KBr) 1636, 1610, 1524 cm$^{-1}$; $^1$H NMR (250 MHz, DMSO-$d_6$): d 3.78 (s, 3H, OCH$_3$), 3.83 (s, 3H, OCH$_3$), 3.89 (s, 3H, OCH$_3$), 6.49 (d, 1H, J=1.9 Hz, $H_{Ar}$), 6.79 (d, 1H, J=1.9 Hz, $H_{Ar}$), 6.92 (d, 2H, J=8.7 Hz, $H_{Ar}$), 7.49 (d, 2H, J=8.7 Hz, $H_{Ar}$), 7.78 (s, 1H, $H_{Ar}$), 13.50 (broad s, 1H, NH). $^{13}$C NMR (62.90 MHz, CDCl$_3$): d 55.1, 55.6, 56.1, 90.2, 95.2, 108.9, 112.9 (2), 128.2, 130.7 (2), 132.0, 136.3, 140.9, 156.4, 158.5, 162.5, 180.5. MS (ionspray): m/z 328 (M+1)$^+$; Anal. calculated for $C_{18}H_{17}NO_3S$: C, 66.03; H. 5.23; N, 4.28. Found: C, 66.30; H, 5.30; N, 4.35.

EXAMPLE 5

5,7-Dimethoxy-3-(4-methoxyphenyl)-1-methyl-1,2-dihydro-2-quinolinone (Compound 7)

(CRL8244)

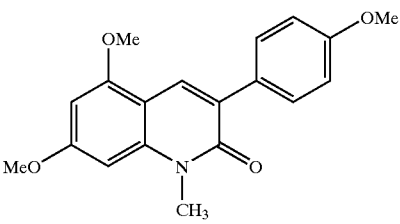

600 mg (1.93 mmol) of compound 1 are dissolved in 30 ml of anhydrous N,N-dimethylformamide (DMF), under a nitrogen atmosphere. At 0° C., 93 mg (3.86 mmol, 2 eq) of NaH, washed beforehand with petroleum ether, are added portionwise to the reaction solution (exothermic reaction). A solution of methyl iodide (0.48 ml, 7.72 mmol, 4 eq) diluted in 5 ml of DMF is added to the medium. The reaction is heated at 90° C. for 18 hours. After cooling, water is added to the reaction mixture and the solution is then stirred for 15 min. The solid obtained is collected by filtration through a sinter funnel and then rinsed with water. The solid is dissolved in $CH_2Cl_2$ and washed twice with water. The organic phase obtained is dried over $MgSO_4$ and then evaporated under reduced pressure. The residue obtained is purified by chromatography on a column of silica (8/2 $CH_2Cl_2$/EtOAc) to give 408 mg (68%) of compound 7 and 157 mg (25%) of derivative 7a.

Compound 7 m.p. 125° C. (EtOAc/PE); IR (KBr) n 1635, 1596, 1590, 1514 cm$^{-1}$; $^1$H NMR (250 MHz, CDCl$_3$): d 3.73 (s, 3H, NCH$_3$), 3.83 (s, 3H, OCH$_3$), 3.91 (s, 6H, OCH$_3$), 6.30 (d, 1H, J=2.0 Hz, $H_{Ar}$), 6.37 (d, 1H, J=2.0 Hz, $H_{Ar}$), 6.94 (d, 2H, J=7.5 Hz, $H_{Ar}$), 7.67 (d, 2H, J=7.5 Hz, $H_{Ar}$), 8.12 (s, 1H, $H_{Ar}$). $^{13}$C NMR (62.90 MHz, CDCl$_3$): d 30.3, 55.3, 55.5, 55.8, 90.2, 92.6, 106.1, 113.5 (2), 127.0, 130.0, 130.1 (2), 130.2, 141.7, 157.6, 159.1, 162.2 (2). MS (ionspray): m/z 326 (M+1)$^+$; Anal. calculated for $C_{19}H_{19}NO_4$: C, 70.14; H, 5.89; N, 4.30. Found: C, 70.00; H, 5.73; N, 4.24.

Compound 7a:

2,5,7-Trimethoxy-3-(4-methoxyphenyl)quinoline

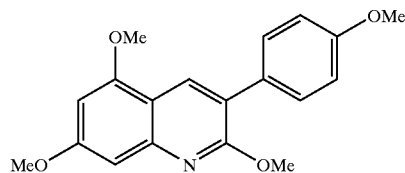

m.p. 106–107° C. (EtOAc/PE); IR (KBr) n 1621, 1515, 1265 cm$^{-1}$; $^1$H NMR (250 MHz, CDCl$_3$): d 3.86 (s, 3H, OCH$_3$), 3.94 (s, 6H, OCH$_3$), 4.08 (s, 3H, OCH$_3$), 6.40 (d, 1H, J=1.8 Hz, $H_{Ar}$), 6.85 (d, 1H, J=1.8 Hz, $H_{Ar}$) 6.97 (d, 2H, J=8.8 Hz, $H_{Ar}$), 7.57 (d, 2H, J=8.8 Hz, $H_{Ar}$), 8.26 (s, 1H, $H_{Ar}$). $^{13}$C NMR (62.90 MHz, CDCl$_3$): d 53.5, 55.3, 55.5, 55.6, 95.9, 98.5, 112.8, 113.6 (2), 122.1, 129.6, 130.5 (2), 132.3, 147.9, 156.3, 158.9, 160.6, 161.3. MS (ionspray): 326 m/z (M+1)⁺; Anal. calculated for $C_{19}H_{19}NO_4$: C, 70.14; H, 5.89; N, 4.30. Found: C, 69.89; H, 5.81; N, 4.10.

EXAMPLE 6

5,7-Dimethozy-3-(4-hydroxyphenyl)-1-methyl-1,2-dihydro-2-quinolinone (Compound 8)

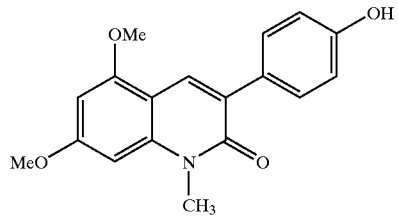

408 mg (1.3 mmol) of compound 7 are dissolved in 15 ml of acetic acid, under an inert atmosphere. A commercial solution of 48% HBr in water (2 ml) is added dropwise (exothermic reaction) to the reaction mixture. The final solution is refluxed with stirring for 5 h. After cooling, the reaction is diluted by addition of water and is then neutralized with 10% sodium hydroxide solution (pH=6–7). The product is extracted with dichloromethane (twice). The organic phase is dried over $MgSO_4$ and then evaporated under reduced pressure. The residue obtained is purified by chromatography on a column of silica (eluent: 7/3 $CH_2Cl_2$/EtOAc) to give 220 mg (56%) of compound 8.

m.p. 204–205° C. (EtOAc); ¹H NMR (250 MHz, DMSO-d₆): d 3.63 (s, 3H, NCH₃), 3.89 (s, 3H, OCH₃), 3.90 (s, 3H, OCH₃), 6.46 (d, 1H, J=1.9 Hz, $H_{Ar}$), 6.54 (d, 1H, J=1.9 Hz, $H_{Ar}$), 6.76 (d, 2H, J=8.5 Hz, $H_{Ar}$), 7.48 (d, 2H, J=8.5 Hz, $H_{Ar}$), 7.93 (s, 1H, $H_{Ar}$), 9.47 (s, 1H, OH). ¹³C NMR (62.90 MHz, DMSO-d₆): d 30.5, 56.1, 56.5, 91.3, 93.4, 105.3, 115.2 (2), 126.5, 128.4, 129.2, 130.2 (2), 141.7, 157.4 (2), 161.4, 162.5. MS: m/z 312 (M+1)⁺. Anal. calculated for $C_{18}H_{17}NO_4$: C, 69.44; H, 5.50; N, 4.50. Found: C, 69.65; H, 5.59; N, 4.60.

EXAMPLE 7

5,7-Dihydroxy-3-(4-hydroxyphenyl)-1-methyl-1,2-dihydro-2-quinolinone (Compound 9)

(CRL8321)

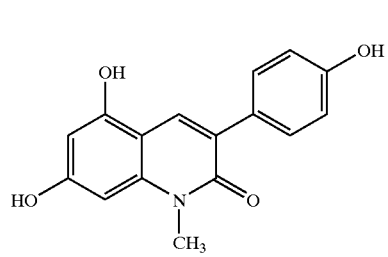

1. Method A: 200 mg (0.61 mmol) of compound 7 are dissolved in 15 ml of acetic acid, under an inert atmosphere. A commercial solution of 48% HBr in water (1 ml) is added dropwise (exothermic reaction) to the reaction mixture. The final solution is refluxed with stirring for 3 days. After cooling, the reaction is diluted by addition of water and is then neutralized with 10% sodium hydroxide solution (pH= 6–7). The product is extracted with dichloromethane (twice). The organic phase is dried over $MgSO_4$ and then evaporated under reduced pressure. The residue obtained is purified by chromatography on a column of silica (eluent: 9/1 $CH_2Cl_2$/MeOH) to give 61 mg (35%) of compound 9.

2. Method B: 1.0 g (3.1 mmol) of compound 7 is dissolved in 15 ml of dichloromethane, under an inert atmosphere. At 0° C., 1.81 ml (19.0 mmol, 6 eq) of boron tribromide are added dropwise (exothermic reaction) to the reaction mixture. The final solution is stirred at room temperature for 18 h. The reaction is hydrolyzed by addition (dropwise) of water and is then neutralized with 10% sodium hydroxide solution (pH=6–7). The product is extracted with dichloromethane (twice). The organic phase is dried over $MgSO_4$ and then evaporated under reduced pressure. The residue obtained is purified on a column of silica (eluent: 9/1 $CH_2Cl_2$/MeOH) to give 688 mg (76%) of compound 9.

m.p. >280° C. (EtOAc); ¹H NMR (250 MHz, DMSOd-₆): d 3.53 (s, 3H, CH₃), 6.25 (s, 2H, $H_{Ar}$), 6.76 (d, 2H, J=8.8 Hz, $H_{Ar}$), 7.47 (d, 2H, J=8.8 Hz, $H_{Ar}$), 7.92 (s, 1H, $H_{Ar}$), 9.42 (s, 1H, OH), 10.00 (s, 1H, OH), 10.35 (s, 1H, OH). ¹³C NMR (62.90 MHz, DMSOd-₆): d 29.7, 91.8, 96.5, 103.5, 114.7 (2), 124.3, 128.4, 129.7 (3), 141.7, 155.9, 156.7, 160.6, 161.1. MS (ionspray): m/z 284 (M+1)⁺; Anal. calculated for $C_{16}H_{13}NO_4$: C, 67.84; H, 4.63; N, 4.94. Found: C, 67.68; H, 4.46; N, 4.78.

EXAMPLE 8

5,7-Dimethoxy-3-(4-methoxyphenyl)-1-methyl-1,2-dihydro-2-quinolinethione (Compound 10)

(CRL8245)

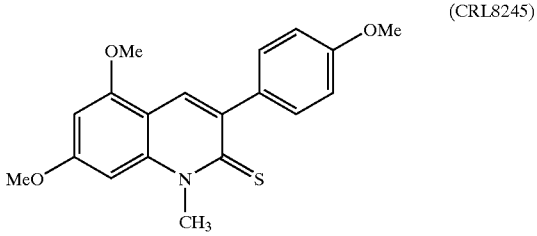

500 mg (1.5 mmol) of compound 7 are dissolved in 30 ml of toluene, under a nitrogen atmosphere. 870 mg (2.1 mmol, 1.4 eq) of Lawesson's reagent are added to this reaction mixture. The reaction is refluxed for 12 h. After cooling, the solvent is evaporated off. The residue obtained is purified by chromatography on a column of silica (3/7 EtOAc/PE) to give 376 mg (72%) of compound 10.

m.p. 176–177° C. (EtOAc/PE); IR (KBr) 1613, 1570, 1512 cm⁻¹; ¹H NMR (250 MHz, CDCl₃): d 3.84 (s, 3H, OCH₃), 3.91 (s, 3H, OCH₃), 3.95 (s, 3H, OCH₃), 4.39 (s, 3H, NCH₃), 6.39 (d, 1H, J=2.0 Hz, $H_{Ar}$), 6.56 (d, 1H, J=2.0 Hz, $H_{Ar}$), 6.93 (d, 2H, J=7.5 Hz, $H_{Ar}$), 7.43 (d, 2H, J=7.5 Hz, $H_{Ar}$) 7.97 (s, 1H, $H_{Ar}$). ¹³C NMR (62.90 MHz, CDCl₃): d 39.5, 55.2, 55.6, 55.9, 91.1, 94.6, 109.9, 113.1 (2), 126.6, 130.8 (2), 134.3, 138.6, 142.7, 157.6, 158.8, 162.7, 184.5. MS: m/z 342 (M+1)⁺; Anal. calculated for $C_{19}H_{19}NO_3S$: C, 66.84; H, 5.61; N, 4.10. Found: C, 66.70; H, 5.53; N, 4.03.

EXAMPLES 9

Ethyl 2-[5,7-Dimethoxy-3-(4-hydroxyphenyl)-2-oxo-1,2-dihydro-1-quinolinyl]acetate )
(Compound 11)

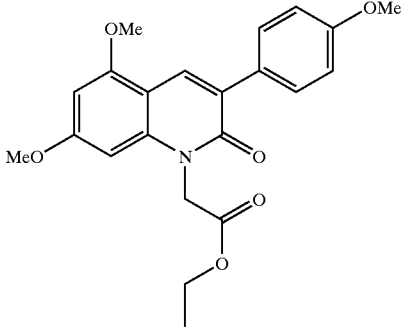
(CRL8314)

1.0 g (3.2 mmol) of compound 1 is dissolved in 30 ml of anhydrous N,N-dimethylformamide (DMF), under a nitrogen atmosphere. At 0° C., 115 mg (4.8 mmol, 1.5 eq) of NaH, washed beforehand in petroleum ether, are added portionwise to the reaction solution (exothermic reaction). A solution of ethyl bromoacetate (0.72 ml, 6.4 mmol, 2 eq) in 5 ml of DMF is added to the medium. The reaction is heated at 90° C. for 2–3 h. After cooling, water is added to the reaction mixture, which is then stirred for 15 min. The solution is extracted with ethyl acetate (twice). The organic phase is dried over $MgSO_4$ and then evaporated under reduced pressure. The residue obtained is purified by chromatography on a column of silica (7/3 $CH_2Cl_2$/EtOAc) to give 890 mg (70%) of compound 11 and 318 mg (25%) of derivative 11a.

Compound 11:
m.p. 160–161° C. (EtOAc/PE); IR (KBr) 1735, 1647, 1609 cm$^{-1}$; $^1$H NMR (250 MHz, CDCl$_3$): d 1.6 (t, 3H, J=7.1 Hz, COOCH$_2$CH$_3$), 3.83 (s, 3H, OCH$_3$), 3.87 (s, 3H, OCH$_3$), 3.92 (s, 3H, OCH$_3$), 4.22 (q, 2H, J=7.1 Hz, COOCH$_2$CH$_3$), 5.10 (s, 2H, CH$_2$CO), 6.14 (d, 1H, J=2.0 Hz, H$_{Ar}$), 6.30 (d, 1H, J=2.0 Hz, H$_{Ar}$), 6.94 (d, 2H, J=7.5 Hz, H$_{Ar}$), 7.69 (d, 2H, J=7.5 Hz, H$_{Ar}$), 8.18 (s, 1H, H$_{Ar}$). $^{13}$C NMR (62.90 MHz, CDCl$_3$): d 14.2, 44.8, 55.3, 55.5, 55.9, 61.6, 90.0, 92.8, 106.2, 113.5 (2), 126.6, 129.6, 130.1 (2), 131.0, 141.1, 157.8, 159.2, 161.9, 162.5, 168.4. MS (ionspray): m/z 398 (M+1)$^+$; Anal. calculated for C$_{22}$H$_{23}$NO$_6$: C, 66.49; H, 5.83; N, 3.52. Found: C, 66.60; H, 6.03; N, 3.75.

Compound 11a
Ethyl 2-([5,7-Dimethoxy-3-(4-methoxyphenyl)-2-quinolinyl]oxy)acetate

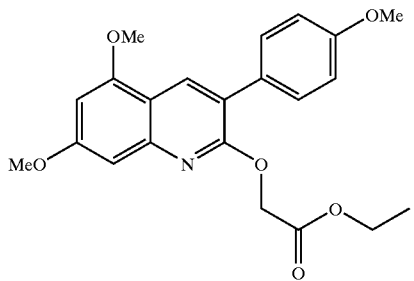

m.p. 95–96° C. (EtOAc/PE); IR (KBr) n 1754, 1622, 1516, 1265 cm$^{-1}$; $^1$H NMR (250 MHz, CDCl$_3$): d 1.27 (t, 3H, J=7.1 Hz, CH$_3$), 3.86 (s, 3H, OCH$_3$), 3.91 (s, 3H, OCH$_3$), 3.93 (s, 3H, OCH$_3$), 4.24 (q, 2H, J=7.1 Hz, OCH$_2$), 5.05 (s, 2H, NCH$_2$), 6.40 (d, 1H, J=2.0 Hz, H$_{Ar}$), 6.76 (d, 1H, J=2.0 Hz, H$_{Ar}$), 6.98 (d, 2H, J=9.0 Hz, H$_{Ar}$), 7.68 (d, 2H, J=9.0 Hz, H$_{Ar}$), 8.30 (s, 1H, H$_{Ar}$). $^{13}$C NMR (62.90 MHz, CDCl$_3$): d 14.2, 55.3, 55.5, 55.7, 60.9, 62.7, 96.2, 98.6, 113.4, 113.7 (2), 121.7, 129.2, 130.6 (2), 132.8, 147.3, 156.3, 158.8, 159.1, 161.4, 169.5. MS (ionspray): m/z 398(M+1)$^+$; Anal. calculated for C$_{22}$H$_{23}$NO$_6$: C, 66.49; H, 5.83; N, 3.52. Found: C, 66.63; H, 5.90; N, 3.60.

EXAMPLE 10

Methyl 3-[5,7-Dimethoxy-3-(4-hydroxyphenyl)-2-oxo-1,2-dihydro-1-quinolinyl]propanoate
(Compound 12)

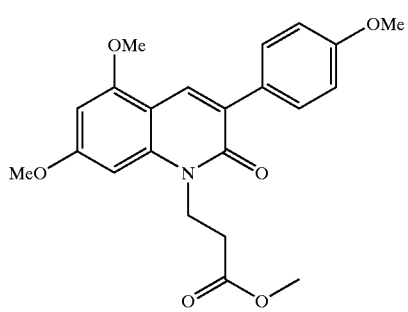
(CRL8318)

1.0 g (3.2 mmol) of compound 1 is dissolved in 20 ml of anhydrous N,N-dimethylformamide (DMF) in the presence of 2.9 ml of methyl acrylate (32.0 mmol, 10 eq), under a nitrogen atmosphere. At 0° C., 2–3 drops of Triton B are added to the reaction solution. The mixture is stirred for 4 h at room temperature. The DMF and methyl acrylate are evaporated off under reduced pressure. The residue obtained is taken up in ethyl acetate and washed twice with water. The organic phase obtained is dried over $MgSO_4$ and then evaporated under reduced pressure. The crude product is purified by chromatography on a column of silica (8/2 $CH_2Cl_2$/EtOAc) to give 1.06 g (83%) of compound 12.

m.p. 100–101° C. (EtOAc); IR (KBr) 1725, 1638 cm$^{-1}$; $^1$H NMR (250 MHz, CDCl$_3$): d 2.78 (t, 2H, J=8.0 Hz, CH$_2$), 3.68 (s, 3H, COOCH$_3$), 3.80 (s, 3H, OCH$_3$), 3.88 (s, 6H, OCH$_3$), 4.57 (t, 2H, J=8.0 Hz, CH$_2$), 6.26 (d, 1H, J=2.0 Hz, H$_{Ar}$), 6.46 (d, 1H, J=2.0 Hz, H$_{Ar}$), 6.92 (d, 2H, J=8.8 Hz, H$_{Ar}$), 7.66 (d, 2H, J=8.8 Hz, H$_{Ar}$), 8.11 (s, 1H, H$_{Ar}$). $^{13}$C NMR (62.90 MHz, CDCl$_3$): d 31.9, 39.1, 51.8, 55.2, 55.5, 55.7, 89.8, 92.6, 106.2, 113.4 (2), 126.5, 129.5, 129.9 (2), 130.3, 140.5, 157.6, 159.0, 161.7, 162.4, 172.0. MS (ionspray): m/z 398 (M+1)$^+$; Anal. calculated for C$_{22}$H$_{23}$NO$_6$: C, 66.49; H, 5.83; N, 3.52. Found: C, 66.55; H, 5.70; N, 3.50.

EXAMPLE 11

Benzyl 2-[5,7-Dimethoxy-3-(4-methoxyphenyl)-2-oxo-1,2-dihydro-1-quinolinyl]acetate
(Compound 13)

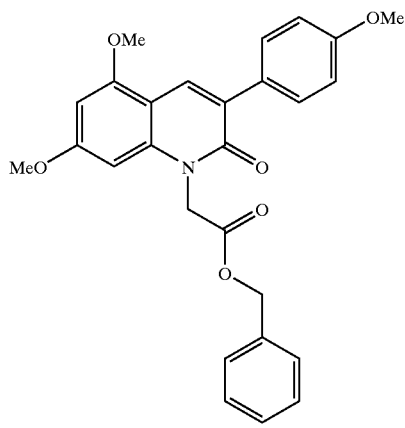

300 mg (0.96 mmol) of compound 1 are dissolved in 10 ml of anhydrous N,N-dimethylformamide (DMF), under a nitrogen atmosphere. At 0° C., 35 mg (1.40 mmol, 1.5 eq) of NaH, washed beforehand in petroleum ether, are added portionwise to the reaction solution (exothermic reaction). A solution of benzyl bromoacetate (0.31 ml, 1.90 mmol, 2 eq) diluted in 5 ml of DMF is added to the medium. The reaction is heated at 90° C. for 2 h. After cooling, water is added to the reaction mixture, which is then stirred for 15 min. The solution is extracted with dichloromethane (twice). The organic phase is dried over $MgSO_4$ and then evaporated under reduced pressure. The residue obtained is purified by chromatography on a column of silica (eluent: $CH_2Cl_2$) to give 317 mg (72%) of compound 13 and 88 mg (20%) of derivative 13a.

Compound 13:

m.p. 199–200° C. ($Et_2O$ wash); IR (KBr) 1748, 1642, 1617 $cm^{-1}$; $^1H$ NMR (250 MHz, $CDCl_3$): d 3.68 (s, 3H, $OCH_3$), 3.84 (s, 3H, $OCH_3$), 3.92 (s, 3H, $OCH_3$), 5.16 (s, 2H, $CH_2$), 5.21 (s, 2H, $CH_2$), 6.03 (d, 1H, J=2.0 Hz, $H_{Ar}$), 6.27 (d, 1H, J=2.0 Hz, $H_{Ar}$), 6.94 (d, 2H, J=7.5 Hz, $H_{Ar}$), 7.25–7.32 (m, 5H, $H_{Ar}$), 7.68 (d, 2H, J=7.5 Hz, $H_{Ar}$), 8.17 (s, 1H, $H_{Ar}$). $^{13}C$ NMR (62.90 MHz, $CDCl_3$): d 44.7, 55.3, 55.4, 55.8, 67.1, 89.8, 93.0, 106.2, 113.5 (2), 126.5, 128.3 (2), 128.4, 128.5 (2), 129.5, 130.1 (2), 131.1, 135.3, 141.0, 157.8, 159.2, 161.8, 162.4, 168.3. MS (ionspray): m/z 460 $(M+1)^+$;

Compound 13a:

Benzyl 2-([5,7-Dimethoxy-3-(4-methoxyphenyl)-2-quinolinyl]oxy)acetate

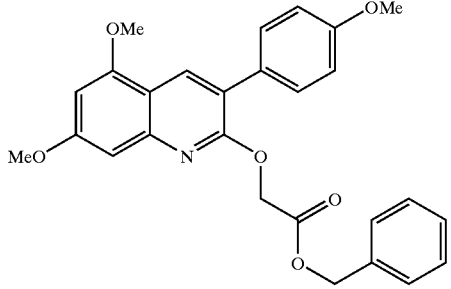

m.p. 114–115° C. (ether); IR (KBr) n 1761, 1621, 1517 $cm^{-1}$; $^1H$ NMR (250 MHz, $CDCl_3$) d 3.87 (s, 3H, $OCH_3$), 3.91 (s, 3H, $OCH_3$), 3.95 (s, 3H, $OCH_3$), 5.17 (s, 2H, $OCH_2$), 5.27 (s, 2H, $OCH_2$), 6.44 (d, 1H, J=2.0 Hz, $H_{Ar}$), 6.76 (d, 2H, J=2.0 Hz, $H_{Ar}$), 7.00 (d, 2H, J=8.0 Hz, $H_{Ar}$), 7.26–7.38 (m, 5H, $H_{Ar}$), 7.71 (d, 2H, J=8.0 Hz, $H_{Ar}$), 8.36 (s, 1H, $H_{Ar}$). $^{13}C$ NMR (62.90 MHz, $CDCl_3$) d 55.2, 55.4, 55.5, 62.6, 66.4, 96.2, 98.5, 113.4, 113.6 (2), 121.6, 128.0 (2), 128.4 (3), 129.0, 130.5 (2), 132.7, 135.6, 147.2, 156.1, 158.6, 159.0, 161.3, 169.3. MS (ionspray): m/z 460 $(M+1)^+$.

EXAMPLE 12

2-[5,7-Dimethoxy-3-(4-methoxyphenyl)-2-oxo-1,2-dihydro-1-quinolinyl]acetic Acid (Compound 14)

(CRL8317)

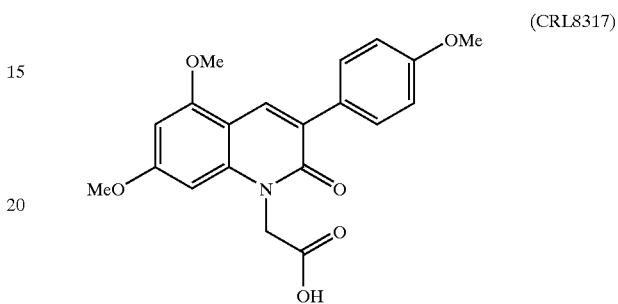

1.0 g (2.2 mmol) of benzyl ester 13 is dissolved in dioxane (30 ml) in a round-bottomed flask. 10% palladium-on-charcoal (100 mg) is added to the reaction solution. The debenzylation reaction is carried out using Parr apparatus under 40 psi of hydrogen at room temperature for 4 h. The reaction medium is filtered through Celite and the filtrate is evaporated under reduced pressure. The crystalline product obtained is washed with ether to give 764 mg (95%) of compound 14.

m.p. 179–180° C. ($Et_2O$ wash); IR (KBr) 1732, 1614, 1583 $cm^{-1}$; $^1H$ NMR (250 MHz, DMSO-$d_6$): d 3.77 (s, 3H, $OCH_3$), 3.85 (s, 3H, $OCH_3$), 3.91 (s, 3H, $OCH_3$), 5.02 (s, 2H, $CH_2$), 6.46 (s, 1H, $H_{Ar}$), 6.47 (s, 1H, $H_{Ar}$), 6.93 (d, 2H, J=9.0 Hz, $H_{Ar}$), 7.62 (d, 2H, J=9.0 Hz, $H_{Ar}$), 8.03 (s, 1H, $H_{Ar}$). $^{13}C$ NMR (62.90 MHz, DMSO-$d_6$): d: 44.9, 55.5, 56.1, 56.6, 91.3, 93.3, 105.3, 113.8 (2), 125.7, 129.4, 130.1 (2), 130.4, 141.3, 157.6, 159.1, 161.3, 162.8, 170.1. MS (ionspray): m/z 370 $(M+1)^+$. Anal. calculated for $C_{20}H_{19}NO_6$: C, 65.03; H, 5.18; N, 3.79. Found: C, 65.00; H, 5.25; N, 3.85.

EXAMPLE 13

Benzyl 3-[5,7-Dimethoxy-3-(4-methoxyphenyl)-2-oxo-1,2-dihydro-1-quinolinyl]propanoate
(Compound 15)

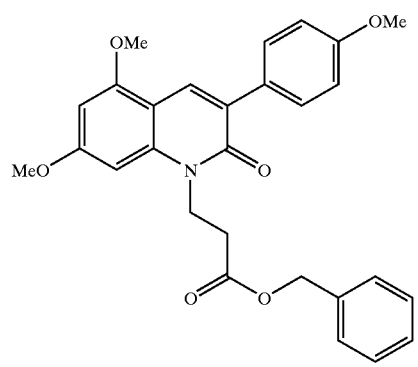

150 mg (0.48 mmol) of compound 1 are dissolved in 10 ml of anhydrous N,N-dimethylformamide (DMF) in the presence of 782 mg (4.8 mmol, 10 eq) of benzyl acrylate, under a nitrogen atmosphere. At 0° C., 2–3 drops of Triton B are added to the reaction solution. The solution is stirred for 18 h at room temperature. The solvents are evaporated off under reduced pressure. The residue obtained is taken up in ethyl acetate and washed twice with water. The organic phase obtained is dried over $MgSO_4$ and then evaporated under reduced pressure. The crude product is purified by chromatography on a column of silica (4/6 EtOAc/PE) to give 200 mg (88%) of compound 15.

m.p. 124–125° C. ($Et_2O$/PE); IR (KBr) 1731, 1635, 1600 $cm^{-1}$; $^1$H NMR (250 MHz, $CDCl_3$): d 2.86 (t, 2H, J=8.0 Hz, $COCH_2$), 3.84 (s, 3H, $OCH_3$), 3.85 (s, 3H, $OCH_3$), 3.92 (s, 3H, $OCH_3$), 4.63 (t, 2H, J=8.0 Hz, $NCH_2$), 5.14 (s, 2H, $CH_2$Ph), 6.29 (d, 1H, J=2.0 Hz, $H_{Ar}$), 6.49 (d, 1H, J=2.0 Hz, $H_{Ar}$), 6.94 (d, 2H, J=7.5 Hz, $H_{Ar}$), 7.30–7.35 (m, 5H, $H_{Ar}$), 7.68 (d, 2H, J=7.5 Hz, $H_{Ar}$), 8.13 (s, 1H, $H_{Ar}$). $^{13}$C NMR (62.90 MHz, $CDCl_3$) d 32.2, 39.1, 55.2, 55.4, 55.7, 66.5, 89.7, 92.6, 106.2, 113.4 (2), 126.5, 128.1 (2), 128.2, 128.4 (2), 129.5, 129.9 (2), 130.4, 135.5, 140.5, 157.6, 159.0, 161.7, 162.4, 171.3. MS (ionspray): m/z 474 (M+1)$^+$;

EXAMPLE 14

3-[5,7-Dimethoxy-3-(4-methoxyphenyl)-2-oxo-1,2-dihydro-1-quinolinyl]propanoic Acid (Compound 16)

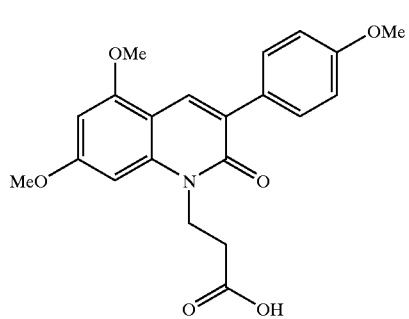

(CRL8319)

1.0 g (2.1 mmol) of benzyl ester 15 is dissolved in dioxane (30 ml) in a round-bottomed flask. 10% palladium-on-charcoal (100 mg) is added to the reaction solution. The debenzylation reaction is carried out using Parr apparatus under 40 psi of hydrogen for 48 h. The reaction medium is filtered through Celite and the filtrate is evaporated under reduced pressure to give, after washing with ether, 780 mg (97%) of compound 16.

m.p. 194–195° C. ($Et_2O$ wash); IR (KBr) 1724, 1637, 1612, 1604 $cm^{-1}$; $^1$H NMR (250 MHz, DMSO-$d_6$): d 2.60 (t, 2H, J=7.5 Hz, $COCH_2$), 3.78 (s, 3H, $OCH_3$), 3.90 (s, 3H, $OCH_3$), 3.92 (s, 3H, $OCH_3$), 4.48 (t, 2H, J=7.5 Hz, $NCH_2$), 6.48 (d, 1H, J=1.8 Hz, $H_{Ar}$), 6.62 (broad s, 1H, $H_{Ar}$), 6.95 (d, 2H, J=8.8 Hz, $H_{Ar}$), 7.62 (d, 2H, J=8.8 Hz, $H_{Ar}$), 8.00 (s, 1H, $H_{Ar}$). $^{13}$C NMR (62.90 MHz, DMSO-$d_6$): d: 32.0, 38.9, 55.1, 55.7, 56.1, 90.6, 93.0, 105.0, 113.3 (2), 125.6, 129.3, 129.5, 129.8 (2), 140.5, 157.2, 158.7, 160.6, 162.4, 172.5. MS: m/z 384 (M+1)$^+$. Anal. calculated for $C_{21}H_{21}NO_6$: C, 65.79; H, 5.52; N, 3.65. Found: C, 65.60; H, 5.51; N, 3.70.

EXAMPLE 15

N,N-Diethyl-3-[5,7-dimethoxy-3-(4-methoxyphenyl)-2-oxo-1,2-dihydro-1-quinolinyl] propanamide (Compound 17)

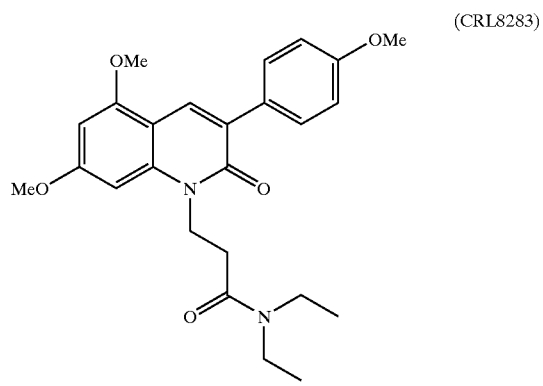

(CRL8283)

1.0 g (2.6 mmol) of compound 16 is dissolved in 25 ml of anhydrous N,N-dimethylformamide (DMF), under a nitrogen atmosphere. At 0° C., 353 mg (2.6 mmol) of hydroxybenzotriazole and 540 mg (2.6 mmol) of cyclohexylcarbodiimide are added to the reaction solution. The reaction is stirred for 10 minutes at 0° C., followed by addition of 0.26 ml (2.6 mmol) of diethylamine. The final solution is stirred for 2 h at 0° C. and then for 24 h at room temperature. The dicyclohexylurea is removed by filtration. The filtrate is extracted with ethyl acetate (twice). The organic phase collected is washed several times with water. The organic phase is dried over $MgSO_4$ and then evaporated under reduced pressure. The residue obtained is purified by chromatography on a column of silica (7/3 $CH_2Cl_2$/EtOAc) to give 680 mg (60%) of compound 17.

m.p. 137–138° C. (EtOAc wash); IR (KBr) 1636, 1617 $cm^{-1}$; $^1$H NMR (250 MHz, $CDCl_3$): d 1.07–1.21 (m, 6H, $CH_3$), 2.78 (t, 2H, J=8.0 Hz, $COCH_2$), 3.30 (q, 2H, J=7.0 Hz, $NCH_2$), 3.39 (q, 2H, J=7.0 Hz, $NCH_2$), 3.84 (s, 3H, $OCH_3$), 3.91 (s, 3H, $OCH_3$), 3.94 (s, 3H, $OCH_3$), 4.65 (t, 2H, J=8.0 Hz, $NCH_2$), 6.29 (d, 1H, J=2.0 Hz, $H_{Ar}$), 6.73 (d, 1H, J=2.0 Hz, $H_{Ar}$), 6.94 (d, 2H, J=7.5 Hz, $H_{Ar}$), 7.67 (d, 2H, J=7.5 Hz, $H_{Ar}$), 8.15 (s, 1H, $H_{Ar}$). $^{13}$C NMR (62.90 MHz, $CDCl_3$) d; 13.1, 14.4, 31.0, 40.1, 40.5, 42.2, 55.3, 55.8 (2), 89.9, 93.1, 106.3, 113.5 (2), 126.6, 129.7, 130.0 (2), 130.5, 140.9, 157.6, 159.1, 162.1, 162.6, 169.9. MS (ionspray): m/z 439 (M+1)$^+$. Anal. calculated for $C_{25}H_{30}N_2O_5$: C, 68.47; H, 6.90; N, 6.39. Found: C, 68.27; H, 6.80; N, 6.40.

EXAMPLE 16

N,N-Diethyl-2-[5,7-dimethoxy-3-(4-methoxy-phenyl)-2-oxo-1,2-dihydro-1-quinolinyl]acetamide (Compound 18)

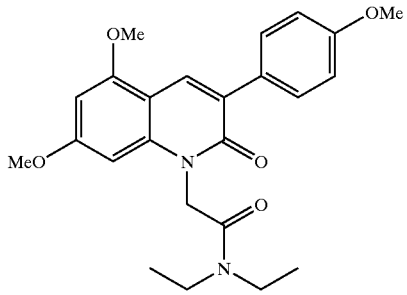
(CRL8315)

1.0 g (3.2 mmol) of compound 1 is dissolved in 30 ml of anhydrous N,N-dimethylformamide (DMF), under a nitrogen atmosphere. At 0° C., 115 mg (4.8 mmol, 1.5 eq) of NaH, washed beforehand in petroleum ether, are added portionwise to the reaction solution (exothermic reaction). A solution of 2-chloro-N,N-diethylacetamide (0.88 ml, 6.4 mmol, 2 eq) diluted in 5 ml of DMF is added to the medium. The reaction is heated at 90° C. for 3 h. After cooling, water is added to the reaction mixture. The reaction solution is extracted with ethyl acetate (twice). The organic phase obtained is dried over MgSO$_4$ and then evaporated under reduced pressure. The residue obtained is purified by chromatography on a column of silica (7/3 CH$_2$Cl$_2$/EtOAc) to give 820 mg (61%) of compound 18 and 408 mg (30%) of derivative 18a.

Compound 18:

m.p. 178–179° C. (EtOAc); IR (KBr) 1642, 1617, 1601 cm$^{-1}$; $^1$H NMR (250 MHz, CDCl$_3$): d 1.10–1.23 (m, 6H, CH$_3$), 3.38–3.49 (m, 4H, CH$_2$), 3.83 (s, 3H, OCH$_3$), 3.86 (s, 3H, OCH$_3$), 3.91 (s, 3H, OCH$_3$), 5.17 (s, 2H, NCH$_2$CO), 6.28 (d, 1H, J=2.0 Hz, H$_{Ar}$), 6.34 (d, 1H, J=2.0 Hz, H$_{Ar}$), 6.93 (d, 2H, J=7.0 Hz, H$_{Ar}$), 7.66 (d, 2H, J=7.0 Hz, H$_{Ar}$), 8.17 (s, 1H, H$_{Ar}$). $^{13}$C NMR (62.90 MHz, CDCl$_3$): d 13.0, 14.2, 40.9, 41.6, 45.3, 55.3, 55.5, 55.8, 90.8, 92.8, 106.3, 113.4 (2), 126.6, 129.9, 130.1 (2), 131.0, 141.7, 157.6, 159.0, 161.9, 162.3, 166.3. MS (ionspray): m/z 425 (M+1)$^+$. Anal. calculated for C$_{24}$H$_{28}$N$_2$O$_5$: C, 67.91, H, 6.65; N, 6.60. Found: C, 67.62; H, 6.44; N, 6.50.

Compound 18a:
N,N-Diethyl-2-([5,7-dimethoxy-3-(4-methoxyphenyl)-2-quinolinyl]oxy)acetamide (18a)

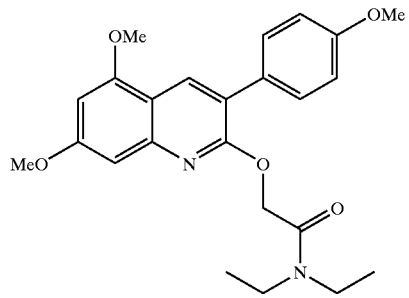

m.p. 146–147° C. (EtOAc/PE); IR (KBr) n 1654, 1624, 1517 cm$^{-1}$; $^1$H NMR (250 MHz, CDCl$_3$): d 1.14 (t, 3H, J=7.5 Hz, CH$_3$), 1.28 (t, 3H, J=7.5 Hz, CH$_3$), 3.36–3.47 (m, 4H, NCH$_2$), 3.85 (s, 3H, OCH$_3$), 3.91 (s, 3H, OCH$_3$), 3.93 (s, 3H, OCH$_3$), 5.17 (s, 2H, NCH$_2$), 6.38 (d, 1H, J=2.0 Hz, H$_{Ar}$), 6.73 (d, 1H, J=2.0 Hz, H$_{Ar}$), 6.97 (d, 2H, J=9.0 Hz, H$_{Ar}$), 7.75 (d, 2H, J=9.0 Hz, H$_{Ar}$), 8.28 (s, 1H, H$_{Ar}$). $^{13}$C NMR (62.90 MHz, CDCl$_3$): d 12.9, 14.2, 40.2, 55.2, 55.4, 55.6, 63.0, 95.8, 98.4, 113.3, 113.5 (2), 121.9, 129.2, 130.6 (2), 132.5, 147.3, 156.2, 158.9, 161.1, 167.3. MS (ionspray): m/z 425 (M+1)$^+$. Anal. calculated for C$_{24}$H$_{28}$N$_2$O$_5$: C, 67.91; H, 6.65; N, 6.60. Found: C, 67.85; H, 6.70; N, 6.51.

EXAMPLE 17

[5,7-Dimethoxy-3-(4-methoxyphenyl)-2-oxo-1,2-dihydro-1-quinolinyl]acetonitrile (Compound 19)

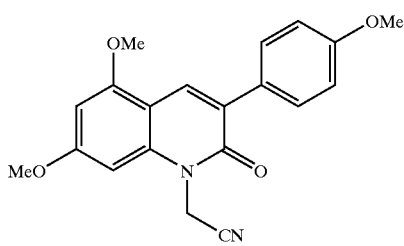
(CRL8255)

1.0 g (3.2 mmol) of compound 1 is dissolved in 30 ml of anhydrous N,N-dimethylformamide (DMF), under a nitrogen atmosphere. At 0° C., 115 mg (4.8 mmol, 1.5 eq) of NaH, washed beforehand in petroleum ether, are added portionwise to the reaction solution (exothermic reaction). A solution of bromoacetonitrile (0.45 ml, 6.4 mmol, 2 eq) diluted in 5 ml of DMF is added to the medium. The reaction is heated for 3 h at 90° C. After cooling, water is added to the reaction mixture. The reaction solution is extracted with ethyl acetate (twice). The organic phase is dried over MgSO$_4$ and then evaporated under reduced pressure. The residue obtained is purified by chromatography on a column of silica (7/3 CH$_2$Cl$_2$/EtOAc) to give 683 mg (61%) of compound 19 and 336 mg (30%) of derivative 19a.

Compound 19:

m.p. 208–209° C. (EtOAc); IR (KBr) 2216, 1660, 1607 cm$^{-1}$; $^1$H NMR (250 MHz, CDCl$_3$): d 3.84 (s, 3H, OCH$_3$), 3.94 (s, 3H, OCH$_3$), 3.95 (s, 3H, OCH$_3$), 5.29 (s, 2H, CH$_2$), 6.36 (s, 2H, H$_{Ar}$), 6.95 (d, 2H, J=8.8 Hz, H$_{Ar}$), 7.65 (d, 2H, J=8.8 Hz, H$_{Ar}$), 8.17 (s, 1H, H$_{Ar}$). $^{13}$C NMR (62.90 MHz, CDCl$_3$): d 30.4, 55.3, 55.8, 56.0, 90.0, 93.5, 106.2, 113.6 (2), 114.8, 126.3, 129.0, 130.0 (2), 131.7, 139.8, 158.1, 159.4, 161.1, 163.0. MS (ionspray): m/z 351 (M+1)$^+$. Anal. calculated for C$_{20}$H$_{18}$N$_2$O$_4$: C, 68.56; H, 5.18; N, 8.00. Found: C, 68.30; H, 5.00; N, 7.90.

Compound 19a:
2-([5,7-Dimethoxy-3-(4-methoxyphenyl)-2-quinolinyl]oxy)acetonitrile (Compound-19a)

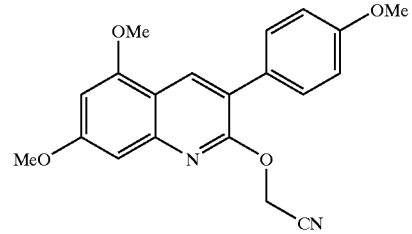

m.p. 149–150° C. (ether); IR (KBr) n 1623, 1586, 1516, 1265 cm$^{-1}$; $^1$H NMR (250 MHz, CDCl$_3$): d 3.87 (s, 3H, OCH$_3$), 3.95 (s, 6H, OCH$_3$), 5.17 (s, 2H, OCH$_2$), 6.45 (d, 1H, J=2.0 Hz, H$_{Ar}$), 6.87 (d, 1H, J=2.0 Hz, H$_{Ar}$), 7.99 (d, 2H, J=9.0 Hz, H$_{Ar}$), 7.54 (d, 2H, J=9.0 Hz, H$_{Ar}$) 8.34 (s, 1H, H$_{Ar}$). $^{13}$C NMR (62.90 MHz, CDCl$_3$): d 50.1, 55.3, 55.6, 55.7, 96.9, 98.6, 113.8 (2), 113.9, 116.1, 121.3, 128.4, 130.5 (2), 133.5, 147.1, 156.3, 157.2, 129.3, 161.8. MS (ionspray): m/z 351 (M+1)$^+$; Anal. calculated for C$_{20}$H$_{18}$N$_2$O$_4$: C, 68.56; H, 5.18; N, 8.00. Found: C, 68.42; H, 5.03; N, 7.88.

EXAMPLE 18

3-[5,7-Dimethoxy-3-(4-methoxyphenyl)-2-oxo-1,2-dihydro-1-quinolinyl]propanenitrile (Compound 20)

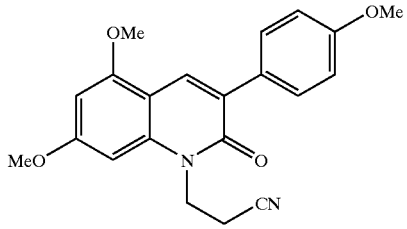

(CRL8247)

500 mg (1.6 mmol) of compound 1 and 0.8 ml (12 mmol) of acrylonitrile are dissolved in 10 ml of anhydrous N,N-dimethylformamide (DMF), under a nitrogen atmosphere. At 0° C., 2 drops of Triton B are added to the reaction solution. The reaction is monitored by TLC. At the end of the reaction, the solvents are evaporated off. The residue is taken up in ethyl acetate and washed several times with water. The organic phase is dried over MgSO$_4$ and then evaporated under reduced pressure. The residue obtained is purified by chromatography on a column of silica (7/3 CH$_2$Cl$_2$/EtOAc) to give 365 mg (63%) of compound 20.

m.p. 156–157° C. (EtOAc/PE); IR (KBr) 2241, 1639 cm$^{-1}$; $^1$H NMR (250 MHz, CDCl$_3$): d 2.88 (t, 2H, J=7.1 Hz, CH$_2$CN), 3.84 (s, 3H, OCH$_3$), 3.93 (s, 3H, OCH$_3$), 3.94 (s, 3H, OCH$_3$), 4.59 (t, 2H, J=7.1 Hz, NCH$_2$), 6.33 (d, 1H, J=1.8 Hz, H$_{Ar}$), 6.45 (d, 1H, J=1.8 Hz, H$_{Ar}$), 6.95 (d, 2H, J=9.0 Hz, H$_{Ar}$), 7.66 (d, 2H, J=9.0 Hz, H$_{Ar}$), 8.17 (s, 1H, H$_{Ar}$). $^{13}$C NMR (62.90 MHz, CDCl$_3$): d 15.9, 39.4, 55.3, 55.7, 55.9, 89.9, 93.0, 106.4, 113.6 (2), 117.7, 126.6, 129.2, 130.0 (2), 131.1, 140.5, 158.0, 159.3, 161.8, 162.7. MS (ionspray): m/z 365 (M+1)$^+$. Anal. calculated for C$_{21}$H$_{20}$N$_2$O$_4$: C, 69.22; H, 5.53; N, 7.69. Found: C, 69.40; H, 5.40; N, 7.80.

EXAMPLE 19

1-[2-(1H-1,2,3,4-Tetrazol-5-yl)ethyl]-5,7-dimethoxy-3-(4-methoxyphenyl)-1,2-dihydro-2-quinolinone (Compound 21)

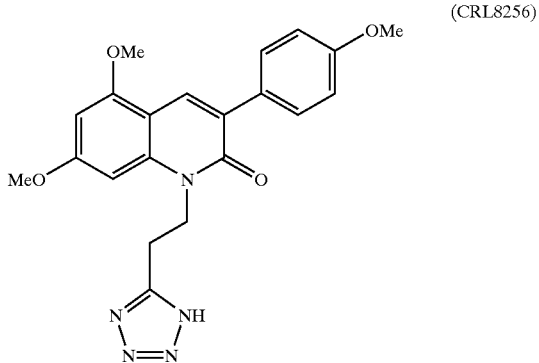

(CRL8256)

350 mg (0.90 mmol) of compound 20 and 0.42 ml (1.53 mmol) of tributyltin azide are dissolved in 20 ml of anhydrous toluene, under an argon atmosphere. The reaction solution is stirred at 105° C. for 65 h. After cooling, the solvent is evaporated off under reduced pressure. The residue obtained is purified by chromatography on a column of silica (9/1 CH$_2$Cl$_2$/MeOH) to give 333 mg (85%) of compound 21.

m.p. 234–235° C. (Et$_2$O wash); IR (KBr) 1618, 1594 cm$^{-1}$; $^1$H NMR (250 MHz, DMSO-d$_6$): d 3.33 (t, 2H, J=6.0 Hz, CH$_2$), 3.79 (s, 3H, OCH$_3$), 3.89 (s, 3H, OCH$_3$), 3.93 (s, 3H, OCH$_3$), 4.67 (t, 2H, J=6.0 Hz, CH$_2$), 6.48 (s, 1H, H$_{Ar}$), 6.52 (s, 1H, H$_{Ar}$), 6.96 (d, 2H, J=9.0 Hz, H$_{Ar}$), 7.59 (d, 2H, J=9.0 Hz, H$_{Ar}$), 8.01 (s, 1H, H$_{Ar}$). $^{13}$C NMR (62.90 MHz, DMSO-d$_6$): d 21.4, 40.8, 55.1, 55.6, 56.1, 90.4, 93.0, 105.0, 113.3 (2), 125.5, 129.3, 129.6, 129.7 (2), 140.4, 153.7, 157.2, 158.7, 160.7, 162.4. MS (ionspray): m/z 408 (M+1)$^+$. Anal. calculated for C$_{21}$H$_{20}$N$_5$O$_4$: C, 61.91; H, 5.20; N, 17.19. Found: C, 62.00; H, 5.19; N, 17.30.

EXAMPLE 20

1-[3-(Dimethylamino)propyl]-5,7-dimethoxy-3-(4-methoxyphenyl)-1,2-dihydro-2-quinolinone (Compound 22)

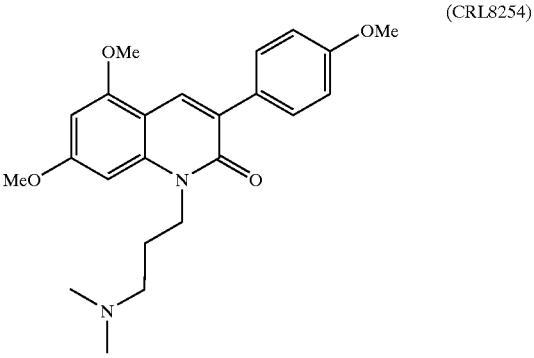

(CRL8254)

1.0 g (3.2 mmol) of compound 1 is dissolved in 20 ml of anhydrous N,N-dimethylformamide (DMF), under a nitrogen atmosphere. At 0° C., 115 mg of NaH (4.8 mmol, 1.5 eq), washed beforehand in petroleum ether, are added portionwise to the reaction solution (exothermic reaction). A solution of 3-dimethylaminopropyl chloride (777 mg, 7.3 mmol, 2.25 eq) in 5 ml of DMF is added to the medium. The reaction is heated for 2–3 h at 90° C. After cooling, water is added to the reaction mixture, followed by stirring for 15 min. The solution is extracted with ethyl acetate (twice). The organic phase is dried over MgSO$_4$ and then evaporated under reduced pressure. The residue obtained is purified by chromatography on a column of silica (8/2 Et$_2$O/MeOH and then 9/1 CH$_2$Cl$_2$/MeOH) to give 887 mg (70%) of compound 22 and 317 mg (25%) of derivative 22a.

Compound 22:

m.p. 94–95° C. (Et$_2$O wash); IR (KBr) 1635, 1598 cm$^{-1}$; $^1$H NMR (250 MHz, CDCl$_3$): d 1.91–2.04 (m, 2H, CH$_2$), 2.28 (s, 6H, CH$_3$), 2.46 (t, 2H, J=7.2 Hz, CH$_2$), 3.83 (s, 3H, OCH$_3$), 3.91 (s, 3H, OCH$_3$), 3.93 (s, 3H, OCH$_3$), 4.36 (t, 2H, J=7.2 Hz, CH$_2$), 6.29 (d, 1H, J=2.0 Hz, H$_{Ar}$), 6.54 (d, 1H, J=2.0 Hz, H$_{Ar}$), 6.94 (d, 2H, J=8.8 Hz, H$_{Ar}$), 7.68 (d, 2H, J=8.8 Hz, H$_{Ar}$), 8.13 (s, 1H, H$_{Ar}$). $^{13}$C NMR (62.90 MHz, CDCl$_3$): d 25.5, 41.8, 45.6 (2), 55.4, 55.5, 55.8, 57.1, 90.3, 92.6, 106.4, 113.5 (2), 126.9, 130.0, 130.1 (2), 130.3, 141.1, 157.6, 159.1, 162.0, 162.3. MS: m/z 397 (M+1)$^+$. Anal. calculated for C$_{23}$H$_{28}$N$_2$O$_4$: C, 69.68; H, 7.12; N, 7.07. Found: C, 69.40; H, 6.97; N, 7.15.

Compound 22a:
N,N-Dimethyl-2-[5,7-dimethoxy-3-(4-methoxyphenyl)-2-quinolyl]oxy-1-propanamide (Compound 22a)

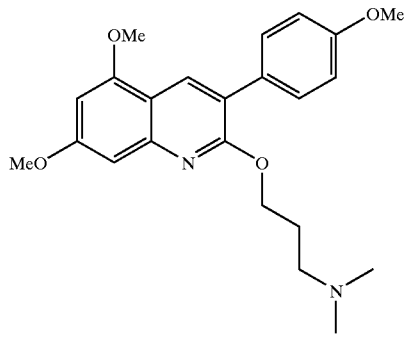

m.p. 54–55° C. (ether); IR (KBr) n 1621, 1584, 1515 cm$^{-1}$; $^1$H NMR (250 MHz, CDCl$_3$): d 1. 96–2.07 (m, 2H, CH$_2$), 2.26 (s, 6H, NCH$_3$), 2.47 (t, 2H, J=6.5 Hz, NCH$_2$), 3.84 (s, 3H, OCH$_3$), 3.92 (s, 6H, OCH$_3$), 4.53 (t, 2H, J=6.5 Hz, OCH$_2$), 6.39 (d, 1H, J=2.2 Hz, H$_{Ar}$), 6.82 (d, 1H, J=2.2 Hz, H$_{Ar}$), 6.96 (d, 2H, J=8.8 Hz, H$_{Ar}$), 7.57 (d, 2H, J=8.8 Hz, H$_{Ar}$), 8.26 (s, 1H, H$_{Ar}$). $^{13}$C NMR (62.90 MHz, CDCl$_3$): d 27.0, 45.4 (2), 55.2, 55.5 (2), 56.6, 64.2, 95.8, 98.5, 112.7, 113.4 (2), 121.9, 129.6, 130.5 (2), 132.1, 147.9, 156.2, 158.8, 160.2, 161.2. MS (ionspray): m/z 397 (M+1)$^+$; Anal. calculated for C$_{23}$H$_{28}$N$_2$O$_4$: C, 69.68; H, 7.12; N, 7.07. Found: C, 69.53; H, 6.92; N, 7.16.

EXAMPLE 21

1-[2-(Dimethylamino)ethyl]-5,7-dimethoxy-3-(4-methoxyphenyl)-1,2-dihydro-2-quinolinone (Compound 23)

(CRL8316)

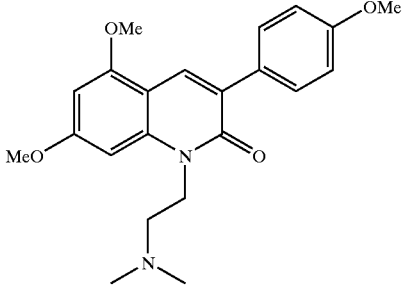

250 mg (0.8 mmol) of compound 1 are dissolved in 15 ml of anhydrous N,N-dimethylformamide (DMF), under a nitrogen atmosphere. At 0° C., 29 mg (1.2 mmol, 1.5 eq) of NaH, washed beforehand in petroleum ether, are added portionwise to the reaction solution (exothermic reaction). A solution of 2-dimethylaminoethyl chloride (230 mg, 2.5 mmol, 3 eq) in 5 ml of DMF is added to the medium. The reaction is heated for 2–3 h at 90° C. After cooling, water is added to the reaction mixture, followed by stirring for 15 min. The solution is extracted with ethyl acetate (twice). The organic phase is dried over MgSO$_4$ and then evaporated under reduced pressure. The residue obtained is purified by chromatography on a column of silica (3/7 Et$_2$O/EtOAc and then 9/1 CH$_2$Cl$_2$/MeOH) to give 205 mg (67%) of compound 23 and 92 mg (30%) of derivative 23a.

Compound 23:
m.p. 113–114° C. (Et$_2$O wash); IR (KBr) 1645, 1617, 1604 cm$^{-1}$; $^1$H NMR (250 MHz, CDCl$_3$): d 2.39 (s, 6H, CH$_3$), 2.65 (t, 2H, J=7.8 Hz, CH$_2$), 3.82 (s, 3H, OCH$_3$), 3.90 (s, 3H, OCH$_3$), 3.91 (s, 3H, OCH$_3$), 4.44 (t, 2H, J=7.8 Hz, CH$_2$), 6.28 (d, 1H, J=2.0 Hz, H$_{Ar}$), 6.49 (d, 1H, J=2.0 Hz, H$_{Ar}$), 6.94 (d, 2H, J=8.8 Hz, H$_{Ar}$), 7.67 (d, 2H, J=8.8 Hz, H$_{Ar}$), 8.12 (s, 1H, H$_{Ar}$). $^{13}$C NMR (62.90 MHz, CDCl$_3$): d 41.6, 45.8 (2), 55.3, 55.6, 55.8 (2), 90.1, 92.7, 106.4, 113.5 (2), 126.9, 129.8, 130.1 (2), 130.4, 141.1, 157.7, 159.1, 161.9, 162.4. MS (ionspray): m/z 383 (M+1)$^+$. Anal. calculated for C$_{22}$H$_{26}$N$_2$O$_4$: C, 69.09; H, 6.85; N, 7.32. Found: C, 69.37; H.,6.98; N, 7.51.

Compound 23a:
N,N-Dimethyl-2-[5,7-dimethoxy-3-(4-methoxyphenyl)-2-quinolyl]oxy-1-ethanamine

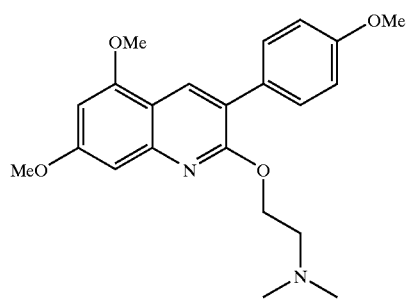

m.p. 49–50° C. (ether wash); IR (KBr) n 1621, 1584, 1515 cm$^{-1}$; $^1$H NMR (250 MHz, CDCl$_3$): d 2.31 (s, 6H, NCH$_3$), 2.77 (t, 2H, J=6.0 Hz, NCH$_2$), 3.85 (s, 3H, OCH$_3$), 3.93 (s, 6H, OCH$_3$), 4.62 (t, 2H, J=6.0 Hz, OCH$_2$), 6.39 (d, 1H, J=2.0 Hz, H$_{Ar}$), 6.81 (d, 1H, J=2.0 Hz, H$_{Ar}$), 6.94 (d, 2H, J=8.8 Hz, H$_{Ar}$), 7.58 (d, 2H, J=8.8 Hz, H$_{Ar}$), 8.25 (s, 1H, H$_{Ar}$). $^{13}$C NMR (62.90 MHz, CDCl$_3$): d 45.7 (2), 55.3, 55.5 (2), 57.8, 63.8, 95.9, 98.5, 112.9, 113.4 (2), 122.0, 129.5, 130.6 (2), 132.3, 147.8, 156.3, 158.9, 160.0, 161.3. MS (ionspray): m/z 383 (M+1)$^+$. Anal. calculated for C$_{22}$H$_{26}$NO$_4$: C, 69.09; H, 6.85; N, 7.32. Found: C, 69.30; H, 6.70; N, 7.29.

EXAMPLE 22

8,10-Dimethoxy-6-(4-methoxyphenyl)-2,3-dihydro-1H,5H-pyrido[3,2,1-ij]quinoline-1,5-dione (Compound 24)

(CRL8285)

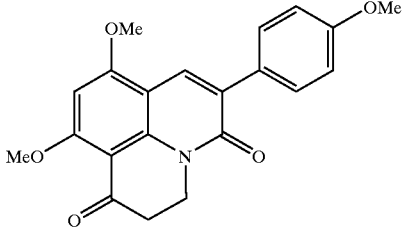

63 mg of P$_2$O$_5$ and 500 mg of PPA are introduced into a round-bottomed flask and the mixture is then stirred for 1 h at 120° C., under a nitrogen atmosphere. Compound 16 (100 mg, 0.26 mmol) is added and the reaction is then stirred for 45 min at 120° C. After cooling, 2N sodium hydroxide solution is added until a pH=6–7 is obtained. The crude product is extracted with CH$_2$Cl$_2$ (twice). The organic phase is dried over MgSO$_4$ and then evaporated under reduced pressure. The residue obtained is purified by chromatography on a column of silica (98/2 CH$_2$Cl$_2$/MeOH) to give 62 mg (65%) of compound 24.

m.p. 240–241° C. (CH$_2$Cl$_2$/PE); IR (KBr)1678, 1649, 1634 cm$^{-1}$; $^1$H NMR (250 MHz, CDCl$_3$): d 2.83 (t, 2H, J=7.0 Hz, COCH$_2$), 3.85 (s, 3H, OCH$_3$), 4.04 (s, 6H, OCH$_3$), 4.54 (d, 2H, J=7.0 Hz, NCH$_2$), 6.32 (s, 1H, H$_{Ar}$) 6.96 (d, 2H, J=7.5 Hz, H$_{Ar}$), 7.68 (d, 2H, J=7.5 Hz, H$_{Ar}$), 8.12 (s, 1H, H$_{Ar}$). $^{13}$C NMR (62.90 MHz, CDCl$_3$): d 37.6, 40.3, 55.3, 56.1, 56.5, 88.9, 103.5, 104.8, 113.6 (2), 127.6, 129.0, 129.8, 130.0 (2), 142.9, 159.4, 161.6, 161.7, 163.7, 190.3. MS (ionspray): m/z 366 (M+1)$^+$. Anal. calculated for C$_{21}$H$_{19}$NO$_5$: C, 69.03; H, 5.24; N, 3.83. Found: C, 68.80; H, 5.34; N, 4.00.

EXAMPLE 23 a) 5,7-Dimethoxy-3-(4-methoxyphenyl)-1-methyl-2-(methylsulfanyl)quinolium Iodide (Compound 25)

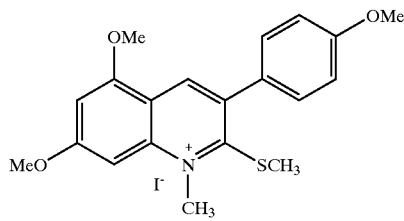

682 mg (2.0 mmol) of compound 10 are dissolved in 30 ml of anhydrous THF, under a nitrogen atmosphere. At room temperature, 3.5 ml of methyl iodide (56 mmol, 28 eq) diluted in 5 ml of THF are added and the reaction is then stirred for 18 h under inert atmosphere. The precipitate observed at the end of the reaction is filtered off on a sinter funnel (washing with THF) to give 761 mg (79%) of compound 25.

m.p. 156–157° C. (THF wash); $^1$H NMR (250 MHz, CDCl$_3$): d 2.44 (s, 3H, SCH$_3$), 3.88 (s, 3H, OCH$_3$), 4.02 (s, 3H, OCH$_3$), 4.28 (s, 3H, OCH$_3$), 5.03 (s, 3H, NCH$_3$), 6.70 (d, 1H, J=1.5 Hz, H$_{Ar}$), 7.03 (d, 2H, J=8.5 Hz, H$_{Ar}$), 7.37 (broad s, 1H, H$_{Ar}$), 7.37 (broad s, 1H, H$_{Ar}$), 7.45 (d, 2H, J=8.5 Hz, H$_{Ar}$), 8.71 (s, 1H, H$_{Ar}$). $^{13}$C NMR (62.90 MHz, CDCl$_3$) d 20.8, 46.5, 55.4, 56.7, 58.5, 92.9, 101.0, 114.4 (2), 117.6, 125.8, 128.9, 130.7 (2), 135.9, 138.8, 144.2, 157.4, 160.3, 167.7. This compound is rapidly used in the next step.

b) 5,7-Dimethoxy-3-(4-methoxyphenyl)-1-methyl-1,2-dihydro-2-quinolinone-2-phenylhydrazone (Compound 26)

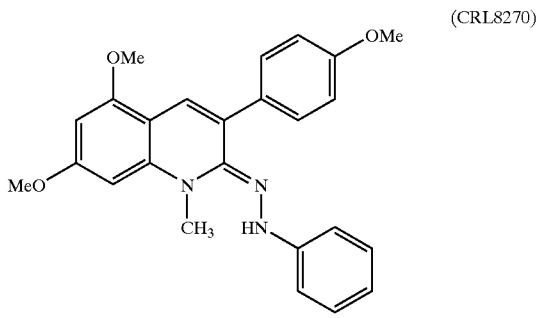
(CRL8270)

200 mg (0.4 mmol) of compound 25 and 0.28 ml (2.8 mmol, 7 eq) of phenylhydrazine are dissolved in 5 ml of anhydrous ethanol, in a sealed tube. The reaction mixture is heated for 18 h at 90° C. After cooling, the ethanol is evaporated off under reduced pressure. The residue is taken up in CH$_2$Cl$_2$ and then washed twice with sodium hydrogen carbonate solution. The organic phase is dried over MgSO$_4$ and then evaporated under reduced pressure. The residue is taken up in methanol, in which the final product precipitates. This product is isolated by filtration (MeOH wash) to give 102 mg (60%) of compound 26.

m.p. 148–149° C. (MeOH wash); IR (KBr) 3340, 1602, 1599 cm$^{-1}$; $^1$H NMR (250 MHz, CDCl$_3$): d 3.58 (s, 3H, CH$_3$), 3.85 (s, 3H, OCH$_3$), 3.86 (s, 3H, OCH$_3$), 3.88 (s, 3H, OCH$_3$), 6.04 (s, 1H, H$_{Ar}$), 6.14 (s, 1H, H$_{Ar}$), 6.48 (broad s, 1H, NH), 6.56–6.67 (m, 3H, H$_{Ar}$), 6.94 (d, 2H, J=8.8 Hz, H$_{Ar}$), 7.11 (t, 2H, J=7.7 Hz, H$_{Ar}$), 7.28 (s, 1H, H$_{Ar}$), 7.28–7.34 (m, 2H, H$_{Ar}$). $^{13}$C NMR (62.90 MHz, CDCl$_3$): d 33.3, 55.4 (2), 55.6, 89.6 (2), 111.6, 113.8 (2), 117.8, 125.9, 128.3, 128.9 (3), 129.5 (2), 130.5, 146.2, 157.2, 159.2 (2), 162.3. MS (ionspray): m/z 416 (M+1)$^+$. Anal. calculated for C$_{25}$H$_{25}$N$_3$O$_3$: C, 72.27; H, 6.06; N, 10.11. Found: C, 72.01; H, 5.86; N, 10.02.

EXAMPLE 24

5,7-Dimethoxy-3-(4-methoxyphenyl)-1-methyl-1,2-dihydro-2-quinolinone-2-(2-pyridyl)hydrazone (Compound 27)

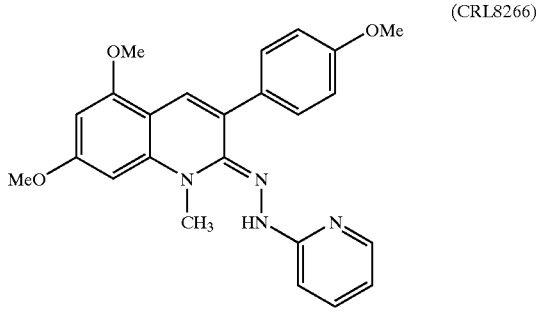
(CRL8266)

150 mg (0.31 mmol) of compound 25 and 237 mg (2.2 mmol, 7 eq) of 2-hydrazinopyridine are dissolved in 5 ml of anhydrous ethanol, in a sealed tube. The reaction mixture is heated for 18 h at 90° C. After cooling, the ethanol is evaporated off under reduced pressure. The residue is taken up in CH$_2$Cl$_2$ and then washed twice with sodium hydrogen carbonate solution. The organic phase is dried over MgSO$_4$ and then evaporated under reduced pressure. The residue is taken up in methanol, in which the final product precipitates. This product is filtered off (MeOH wash) to give 75 mg (58%) of the orange-colored compound 27.

m.p. 182–183° C. (MeOH wash); IR (KBr) 3353, 1628, 1593 cm$^{-1}$; $^1$H NMR (250 MHz, CDCl$_3$): d 3.61 (s, 3H, NCH$_3$), 3.87 (s, 6H, OCH$_3$), 3.90 (s, 3H, OCH$_3$), 6.07 (s, 1H, H$_{Ar}$), 6.17 (s, 1H, H$_{Ar}$), 6.51–6.55 (m, 1H, H$_{pyr}$), 6.94–7.01 (m, 3H, H$_{Ar}$+H$_{pyr}$) 7.14 (broad s, 1H, NH), 7.32–7.36 (m, 3H, H$_{Ar}$), 7.48 (t, 1H, J=7.3 Hz, H$_{pyr}$), 7.91 (d, 1H, J=4.3 Hz, H$_{pyr}$). $^{13}$C NMR (62.90 MHz, CDCl$_3$): d 33.2, 55.3, 55.4, 55.6, 89.7 (2), 104.7, 105.7, 113.4, 114.1 (2), 122.9, 129.0, 129.2 (2), 130.1, 137.5, 140.7, 143.7, 147.8, 157.3, 157.4, 159.2, 162.4. MS (ionspray): m/z 417 (M+1)$^+$. Anal. calculated for C$_{24}$H$_{24}$N$_4$O$_3$: C, 69.21; H, 5.81; N, 13.45. Found: C, 69.50; H, 6.04; N, 13.28.

EXAMPLE 25 a) N-(2-Methoxyphenyl)-2-(4-methoxyphenyl)acetamide (Compouund 30)

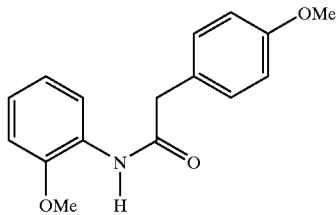

0.46 ml (4.1 mmol) of o-anisidine is diluted in toluene (7 ml) at 0° C., under a nitrogen atmosphere. A solution of 4-methoxyphenylacetyl chloride (0.63 ml, 4.1 mmol) in 5 ml of toluene is added dropwise to the medium. The reaction mixture is stirred at room temperature for 1 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over $MgSO_4$ and then evaporated under reduced pressure. The residue obtained is taken up in petroleum ether, which causes precipitation of the desired product. The crystals thus formed are collected by filtration to give 1.0 g (91%) of compound 30.

m.p. 47–48° C. (toluene); IR (KBr) n 3375, 1667, 1597 cm$^{-1}$; $^1$H NMR (250 MHz, CDCl$_3$): d 3.68 (s, 2H, CH$_2$), 3.72 (s, 3H, OCH$_3$), 3.82 (s, 3H, OCH$_3$), 6.79 (dd 1H, J=1.5, 8.0 Hz, H$_{Ar}$), 6.89–7.03 (m, 4H, H$_{Ar}$), 7.25 (d, 2H, J=8.8 Hz, H$_{Ar}$), 7.79 (broad s, 1H, NH), 8.33 (dd, 1H, J=1.5, 8.0 Hz, H$_{Ar}$). $^{13}$C NMR (62.90 MHz, CDCl$_3$): d 44.2, 55.3, 55.7, 109.9, 114.4 (2), 119.5, 121.0, 123.6, 126.6, 127.6, 130.7 (2), 147.8, 158.9, 169.3. MS (ionspray): m/z 272 (M+1)$^+$.

b) 8-Methoxy-3-(4-methoxyphenyl)-1,2-dihydro-2-quinolinone (Compound 31)

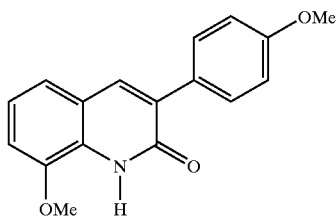

0.31 ml (4.0 mmol, 1.5 eq) of N,N-dimethylformamide is added dropwise to 1.75 ml (19 mmol, 7.5 eq) of POCl$_3$, under a nitrogen atmosphere and at -30° C. The medium is stirred for 15 min at -30° C. and then 723 mg of amide 30 (2.7 mmol) are added. The reaction mixture is warmed to room temperature with stirring and the reaction is then heated at 75° C. for 1.5 h. At the end of the reaction, this solution is poured onto crushed ice, neutralized with 30% aqueous ammonia solution and then extracted with dichloromethane. The organic phase is dried over MgSO$_4$ and then evaporated. The residue obtained is dissolved in 4.75 ml of glacial acetic acid and 0.15 ml of water and the final solution is then refluxed for 3 h. The acetic acid is evaporated off. The residue is dissolved in water, neutralized with 25% sodium hydroxide solution and then finally extracted with dichloromethane. The organic phase is dried over MgSO$_4$ and then evaporated under reduced pressure. The residue is taken up in ethyl acetate, which causes precipitation of the final product. The crystals thus obtained are filtered off to give 75 mg (10%) of compound 31.

The overall yield for the synthesis carried out to obtain compound 31 is 9%.

m.p. 148–149° C. (EtOAc); IR (KBr) n 1652, 1625, 1606, 1541 cm$^{-1}$; $^1$H NMR (250 MHz, DMSO-d$_6$): d 3.79 (s, 3H, OCH$_3$), 3.90 (s, 3H, OCH$_3$), 6.99 (d, 2H, J=8.8 Hz, H$_{Ar}$), 7.09–7.15 (m, 2H, H$_{Ar}$), 7.29 (dd, 1H, J=3.2, 6.0 Hz, H$_{Ar}$), 7.74 (d, 2H, J=8.8 Hz, H$_{Ar}$), 8.03 (s, 1H, H$_{Ar}$), 10.90 (broad s, 1H, NH). $^{13}$C NMR (62.90 MHz, DMSO-d$_6$): d 55.2, 56.0, 110.5, 113.4 (2), 119.6, 120.0, 121.8, 127.9, 128.5, 129.9 (2), 131.6, 136.4, 145.3, 159.1, 160.7. MS (ionspray): m/z 282 (M+1)$^+$; Anal. calculated for C$_{17}$H$_{15}$NO$_3$: C, 72.58; H, 5.37; N, 4.98. Found: C, 72.50; H, 5.50; N, 4.83.

EXAMPLE 26 a) N-(2,5-Dimethoxyphenyl)-2-(4-methoxyphenyl)acetamide (Compound 32)

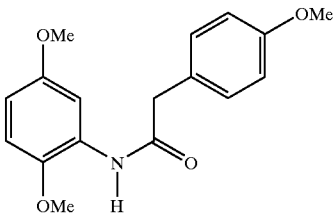

1.0 g (6.5 mmol) of 2,5-dimethoxyaniline is dissolved in toluene (7 ml) at 0° C., under a nitrogen atmosphere. A solution of 4-methoxyphenylacetyl chloride (1.0 ml, 6.5 mmol) diluted in 5 ml of toluene is added dropwise to the medium. The reaction mixture is stirred at room temperature for 1 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over MgSO$_4$ and then evaporated under reduced pressure. The residue obtained is taken up in a minimum amount of petroleum ether, which causes precipitation of the final product. The crystals formed are filtered off on a sinter funnel to give 1.83 g (93%) of compound 32.

m.p. 89–90° C. (toluene); $^1$H NMR (250 MHz, CDCl$_3$): d 3.67 (s, 3H, OCH$_3$), 3.68 (s, 2H, CH$_2$), 3.75 (s, 3H, OCH$_3$), 3.81 (s, 3H, OCH$_3$), 6.53 (dd, 1H, J=3.0, 9.0 Hz, H$_{Ar}$), 6.71 (d, 1H, J=9.0 Hz, H$_{Ar}$), 6.92 (d, 2H, J=8.8 Hz, H$_{Ar}$), 7.25 (d, 2H, J=8.8 Hz, H$_{Ar}$), 7.82 (broad s, 1H, NH), 8.80 (d, 1H, J=3.0 Hz, H$_{Ar}$). $^{13}$C NMR (62.90 MHz, CDCl$_3$): d 44.2, 55.3, 55.7, 56.3, 105.5, 108.6, 110.9, 114.4 (2), 126.4, 128.3, 130.6 (2), 142.0, 153.9, 158.9, 169.3. MS (ionspray): m/z 302 (M+1)$^+$.

b) 5,8-Dimethoxy-3-(4-methoxyphenyl)-1,2-dihydro-2-quinolinone (Compound 33)

(CRL8336)

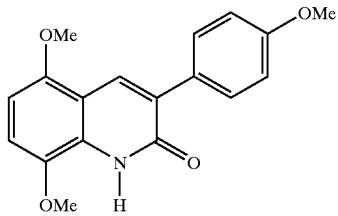

0.31 ml (4.0 mmol, 1.5 eq) of N,N-dimethylformamide is added dropwise to 1.75 ml (20 mmol, 7.5 eq) of POCl$_3$, under a nitrogen atmosphere and at −30° C. The medium is stirred for 15 min at −30° C. and 813 mg of amide 32 (2.7 mmol) are then added. The reaction mixture is warmed to room temperature with stirring and the reaction is then heated at 75° C. for 1.5 h. After this period, the solution is poured onto crushed ice, neutralized with aqueous 30% ammonia solution and then extracted with dichloromethane. The organic phase is dried over MgSO$_4$ and then evaporated. The residue obtained is taken up in 4.75 ml of glacial acetic acid and 0.15 ml of water and the final solution is then refluxed for 3 h. The acetic acid is evaporated off. The residue is dissolved in water, neutralized with 25% sodium hydroxide solution and then finally extracted with dichloromethane. The organic phase is dried over MgSO$_4$ and then evaporated under reduced pressure. The residue is taken up in ethyl acetate, which causes precipitation of the final compound. The crystals thus obtained are filtered off to give 378 mg (45%) of compound 33.

The overall yield for the chemical synthesis to obtain compound 33 is 42%.

m.p. 186–187° C. (EtOAc); IR (KBr) n 1639, 1571, 1515 cm$^{-1}$; $^1$H NMR (250 MHz, CDCl$_3$): d 3.85 (s, 3H, OCH$_3$), 3.90 (s, 3H, OCH$_3$), 3.92 (s, 3H, OCH$_3$), 6.49 (d, 1H, J=8.7 Hz, H$_{Ar}$), 6.84 (d, 1H, J=8.7 Hz, H$_{Ar}$), 6.97 (d, 2H, J=8.8 Hz, H$_{Ar}$), 7.74 (d, 2H, J=8.8 Hz, H$_{Ar}$), 8.19 (s, 1H, H$_{Ar}$), 9.25 (broad s, 1H, NH). $^{13}$C NMR (62.90 MHz, CDCl$_3$): d 55.2, 55.8, 56.2, 101.1, 109.7, 111.4, 113.6 (2), 128.7, 128.8, 130.0 (2), 131.4, 131.7, 139.4, 149.8, 159.5, 161.3. MS (ionspray): m/z 312 (M+1)$^+$. Anal. calculated for C$_{18}$H$_{17}$NO$_4$: C, 69.44; H, 5.50; N, 4.50. Found: C, 69.71; H, 5.59; N, 4.70.

EXAMPLE 27

5,7-Dimethyl-3-phenyl-1,2-dihydro-2-quinolinone (Compound 34)

a) N-(3,5-Dimethoxyphenyl)-2-phenylacetamide (Compound 35)

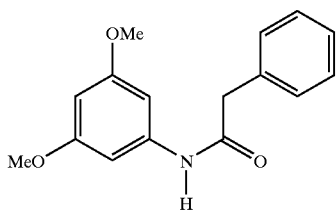

1.0 g (6.5 mmol) of 3,5-dimethoxyaniline is dissolved in toluene (14 ml) at 0° C., under a nitrogen atmosphere. A solution of phenylacetyl chloride (0.86 ml, 6.5 mmol) in 10 ml of toluene is added dropwise to the medium. The reaction mixture is stirred at room temperature for 1 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over MgSO$_4$ and then evaporated. The residue obtained is crystallized from toluene to give 1.55 g (87%) of compound 35.

m.p. 109–111° C. (toluene); IR (KBr) n 3286, 1657, 1616 cm$^{-1}$; $^1$H NMR (250 MHz, CDCl$_3$): d 3.70 (s, 2H, CH$_2$), 3.74 (s, 6H, OCH$_3$), 6.21 (t, 1H, J=2.2 Hz, H$_{Ar}$), 6.66 (d, 2H, J=2.2 Hz, H$_{Ar}$), 7.09 (broad s, 1H, NH), 7.30–7.40 (m, 5H, H$_{Ar}$). $^{13}$C NMR (62.90 MHz, CDCl$_3$) d 44.9, 55.4 (2), 96.8, 15 97.9 (2), 127.7, 129.2 (2), 129.5 (2), 134.3, 139.4, 161.0 (2), 169.1. MS (ionspray): 272 (M+1)$^+$.

b) 2-Chloro-5,7-dimethoxy-3-phenyl-1,2-dihydroquinoline Compound 36)

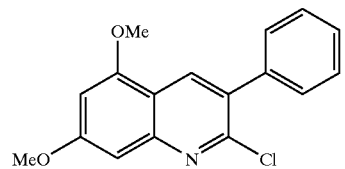

0.64 ml (8.3 mmol, 1.5 eq) of N,N-dimethylformamide is added dropwise to 3.8 ml (41.0 mmol, 7.5 eq) of POCl$_3$, under a nitrogen atmosphere and at −30° C. The medium is stirred for 15 min at −30° C. and 1.5 g of amide 35 (5.5 mmol) are then added. The reaction mixture is warmed to room temperature with stirring and the reaction is then heated at 75° C. for 2.5 h. At the end of the reaction, this solution is poured onto crushed ice, neutralized with aqueous 30% ammonia solution and then extracted with dichloromethane. The organic phase is dried over MgSO$_4$ and then evaporated. The residue obtained is purified by chromatography on a column of silica (eluent: 3/7 EtOAc/PE) to give 800 mg (49%) of compound 36.

m.p. 148–150° C. $^1$H NMR (250 MHz, CDCl$_3$): d 3.93 (s, 6H, OCH$_3$), 6.51 (d, 1H, J=2.2 Hz, H$_{Ar}$), 6.97 (d, 1H, J=2.2 Hz, H$_{Ar}$), 7.40–7.54 (m, 5H, H$_{Ar}$), 8.36 (s, 1H, H$_{Ar}$). $^{13}$C NMR (62.9 MHz, CDCl$_3$): d 55.6, 55.8, 98.6, 98.8, 115.6, 127.9, 128.1 (2), 129.7 (2), 131.2, 133.9, 138.1, 149.2, 150.2, 156.1, 162.3. MS (ionspray): m/z 301 (M+1)$^+$, 303 (M+3)$^+$.

c) 5,7-Dimethoxy-3-phenyl-1,2-dihydro-2-quinolinone (Compound 34)

(CRL8330)

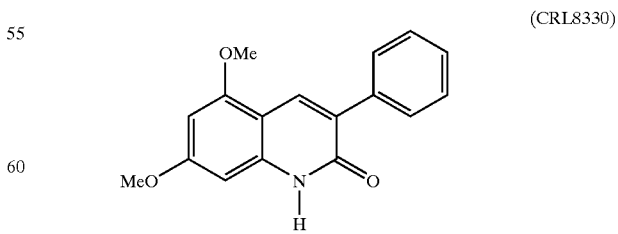

1.52 g (9.9 mmol) of 3,5-dimethoxyaniline and 2.30 g (12 mmol, 1.2 eq) of ethyl (α-formylphenylacetate are mixed together in a round-bottomed flask under a nitrogen atmosphere. The medium is stirred for 1 h at room temperature. A solution of trimethylsilyl polyphosphate (PPSE), freshly prepared from 4.56 g (0.03 mol) of $P_2O_5$, 10.9 ml (0.17 mol) of hexamethyldisiloxane and 50 ml of 1,2-dichloroethane, is added. The final mixture is maintained at 100° C. for 2 h. The heating is stopped and ice is then added to the reaction mixture. This mixture is then neutralized by addition of saturated sodium hydrogen carbonate solution (portionwise addition, exothermic reaction). The product is extracted with dichloromethane (large amount to be used). The organic phase is dried over $MgSO_4$ and then evaporated under reduced pressure. The residue is taken up in ethyl acetate, which causes precipitation of the desired compound. The final product is isolated by filtration through a sinter funnel. After partial concentration of the filtrate, the final product reprecipitates. The solid is reisolated by filtration, this operation being repeated several times. Compound 34 (444 mg) is obtained in a yield of 16%.

m.p. 257–258° C. (EtOAc); IR (KBr) n 1668, 1631, 1569, 1514 cm$^{-1}$; $^1$H NMR (250 MHz, DMSO-d$_6$): d 3.81 (s, 3H, OCH$_3$), 3.89 (s, 3H, OCH$_3$), 6.36 (d, 1H, J=1.8 Hz, H$_{Ar}$), 6.45 (d, 1H, J=1.8 Hz, H$_{Ar}$), 7.28–7.42 (m, 3H, H$_{Ar}$), 7.69 (d, 2H, J=7.0 Hz, H$_{Ar}$), 8.00 (s, 1H, H$_{Ar}$), 11.81 (broad s, 1H, NH). $^{13}$C NMR (62.90 MHz, DMSO-d$_6$): d 55.5, 56.0, 90.0, 93.1, 104.5, 126.9, 127.3, 127.9 (2), 128.4 (2), 131.4, 136.7, 140.8, 156.8, 161.4, 162.2. MS (ionspray): m/z 282 (M+1)$^+$. Anal. calculated for $C_{17}H_{15}NO_3$: C, 72.58; H, 5.37; N, 4.98. Found: C, 72.29; H, 5.20; N, 5.10.

EXAMPLE 28 a) N-(2-Methoxyphenyl)-2-phenylacetamide (Compound 37)

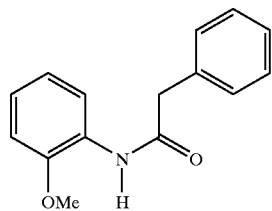

1.37 ml (0.01 mmol) of o-anisidine are dissolved in toluene (14 ml) at 0° C., under a nitrogen atmosphere. A solution of phenylacetyl chloride (1.62 ml, 0.01 mmol) in 5 ml of toluene is added dropwise to the medium. The reaction mixture is stirred at room temperature for 1 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over $MgSO_4$ and then evaporated under reduced pressure. The residue obtained is dissolved in a minimum amount of toluene, which causes precipitation of the final product. After filtration through a sinter funnel, 2.7 g (92%) of compound 37 are isolated.

m.p. 80–81° C. (toluene) [m.p. 85° C.; C. Yamagami et al., Chem. Pharm. Bull. 1984, 32, 5003–5009]; IR (KBr) n 3287, 1652, 1598 cm$^{-1}$; $^1$H NMR (250 MHz, CDCl$_3$): d 3.72 (s, 3H, CH$_3$), 3.76 (s, 2H, CH$_2$), 6.81 (dd, 1H, J=8.0, 1.8 Hz, H$_{Ar}$), 6.91–7.05 (m, 2H, H$_{Ar}$), 7.21–7.37 (m, 4H, H$_{Ar}$), 7.80 (broad s, 1H, NH), 8.35 (dd, 1H, J=8.0, 1.8 Hz, H$_{Ar}$). $^{13}$C NMR (62.90 MHz, CDCl$_3$): d 45.2, 55.7, 109.9, 119.5, 121.1, 123.7, 127.4, 127.6, 129.0 (2), 129.6 (2), 134.6, 147.8, 168.8. MS (ionspray): m/z 242 (M+1)$^+$.

b) 8-Methoxy-3-phenyl-1,2-dihydro-2-quinolinone (Compound 38)

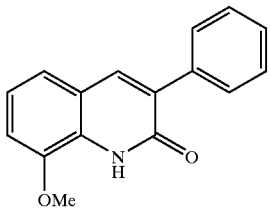

(CRL8339)

1.3 ml (1.68 mmol, 1.5 eq) of N,N-dimethylformamide are added dropwise to 7.3 ml (78 mmol, 7 eq) of POCl$_3$, under a nitrogen atmosphere and at −30° C. The medium is stirred for 15 min at −30° C. and 2.7 g of amide 37 (0.01 mmol) are then added. The reaction mixture is warmed to room temperature with stirring and the reaction is then heated at 75° C. for 1.5 h. At the end of the reaction, this solution is poured onto crushed ice, neutralized with aqueous 30% ammonia solution and then extracted with dichloromethane. The organic phase is dried over $MgSO_4$ and then evaporated. The residue is purified by chromatography on a column of silica (3/7 EtOAc/PE) to give 650 mg (21%) of chloro derivative. After dissolving this derivative in 3.8 ml of glacial acetic acid and 0.12 ml of water, the final solution is refluxed for 3 h. The acetic acid is evaporated off. The residue is dissolved in water, neutralized with 25% sodium hydroxide solution and then finally extracted with dichloromethane. The organic phase is dried over $MgSO_4$ and then evaporated under reduced pressure. The residue is taken up in ethyl acetate, which causes crystallization of the final product. The crystals thus obtained are filtered to give 237 mg (40%) of compound 38.

The overall yield for the synthesis carried out to obtain compound 38 is 8%.

m.p. 188–189° C. (EtOAc); IR (KBr) n 1646, 1607, 1569 cm$^{-1}$; $^1$H NMR (250 MHz, DMSO-d$_6$): d 3.92 (s, 3H, OCH$_3$), 7.13–7.16 (m, 2H, H$_{Ar}$), 7.30–7.46 (m, 4H, H$_{Ar}$), 7.74–7.77 (m, 2H, H$_{Ar}$), 8.09 (s, 1H, H$_{Ar}$), 10.98 (broad s, 1H, NH). $^{13}$C NMR (62.90 MHz, DMSO-d$_6$): d 56.5, 111.3, 120.3, 120.4, 122.4, 128.3 (2), 128.4, 128.7, 129.2 (2), 132.6, 136.7, 138.2, 145.9, 161.1. MS (ionspray): 252 m/z (M+1)$^+$; Anal. calculated for $C_{16}H_{13}NO_2$: C, 76.48; H, 5.21; N, 5.57. Found: C, 76.23; H, 5.14; N, 5.70.

EXAMPLE 29

5,7-Acetoxy-3-(4-acetoxyphenyl)-1,2-dihydro-2-quinolinone (Compound 39)

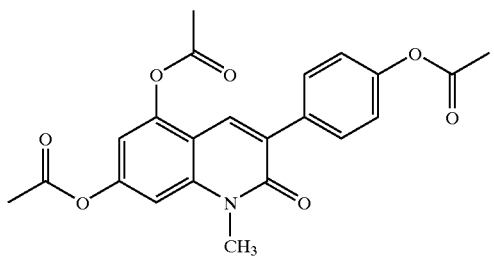

200 mg (0.71 mmol) of compound 9 (CRL8321) are dissolved in acetic anhydride and pyridine (8 ml, v/v) at 0° C., under a nitrogen atmosphere. The reaction mixture is stirred at room temperature for 18 h. The medium is hydrolyzed by addition of water (10 ml) and then extracted with dichloromethane (twice). The organic phase is dried over $MgSO_4$ and then evaporated. The residue obtained is purified by chromatography on a column of silica (1/9 EtOAc/ $CH_2Cl_2$) to give 220 mg (76%) of compound 39.

m.p. 206–207° C. (EtOAc); IR (KBr): n 1769, 1748, 1638, 1598, 1576, 1508 $cm^{-1}$; $^1H$ NMR (250 MHz, $CDCl_3$): d 2.31 (s, 3H, $CH_3$), 2.33 (s, 3H, $CH_3$), 2.40 (s, 3H, $CH_3$), 3.72 (s, 3H, $NCH_3$), 6.92 (d, 1H, J=2.0 Hz, $H_{Ar}$), 7.03 (d, 1H, J=2.0 Hz, $H_{Ar}$), 7.14 (d, 2H, J=8.5 Hz, $H_{Ar}$), 7.67 (d, 2H, J=8.5 Hz, $H_{Ar}$), 7.78 (s, 1H, $H_{Ar}$). $^{13}C$ NMR (62.90 MHz, $CDCl_3$): d 20.8, 21.0, 21.2, 30.5, 105.2, 110.2, 111.8, 121.4 (2), 129.7, 130.3 (2), 131.5, 134.2, 141.0, 148.8, 150.7, 151.9, 161.2, 168.6, 168.8, 169.6. MS (ionspray): m/z 410 ($M^+$+1); Anal. calculated for $C_{22}H_{19}NO_7$: C, 64.54; H, 4.68; N, 3.42. Found: C, 64.83; H, 4.85; N, 3.57.

EXAMPLE 30

3-[5,7-Dimethoxy-3-(4-methoxyphenyl)-2-oxo-1,2-dihydro-1-quinolinyl]butanenitrile (Compound 40)

(CRL8398)

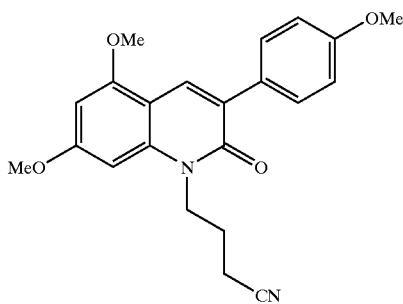

400 mg (1.28 mmol) of compound 1 (CRL8246) are dissolved in 10 ml of anhydrous N,N-dimethylformamide (DMF), under a nitrogen atmosphere. At 0° C., 47 mg (1.92 mmol, 1.5 eq) of sodium hydride, washed beforehand in petroleum ether, are added portionwise to the reaction solution (exothermic reaction). 4-Chlorobutyronitrile (0.23 ml, 2.57 mmol, 2 eq) and sodium iodide (20 mg) are added to the medium. The reaction is heated for 3 h at 90° C. After cooling and evaporation of the DMF, water is added to the residue. The aqueous solution is extracted with ethyl acetate (twice). The organic phase is dried over $MgSO_4$ and then evaporated under reduced pressure. The residue obtained is purified by chromatography on a column of silica (9/1 $CH_2Cl_2$/EtOAc) to give 151 mg (31%) of compound 40a and 161 mg (33%) of derivative 40.

Compound 40:

m.p. 157–158° C. (EtOAc); IR (KBr) n 1639, 1609, 1597, 1575, 1517 $cm^{-1}$; $^1H$ NMR (250 MHz, $CDCl_3$): d 2.10–2.21 (m, 2H, $CH_2$), 2.52 (t, 2H, J=7.2 Hz, $CH_2CN$), 3.83 (s, 3H, $OCH_3$), 3.92 (s, 3H, $OCH_3$), 3.93 (s, 3H, $OCH_3$), 4.43 (t, 2H, J=7.2 Hz, $NCH_2$), 6.31 (d, 1H, J=2.2 Hz, $H_{Ar}$), 6.42 (d, 1H, J=2.2 Hz, $H_{Ar}$), 6.94 (d, 2H, J=8.8 Hz, $H_{Ar}$), 7.66 (d, 2H, J=8.8 Hz, $H_{Ar}$), 8.15 (s, 1H, $H_{Ar}$). $^{13}C$ NMR (62.90 MHz, $CDCl_3$): d 15.3, 23.6, 41.8, 55.4, 55.9, 56.0, 89.6, 93.1, 106.4, 113.6 (2), 119.5, 126.7, 129.6, 130.1 (2), 130.8, 140.7, 157.9, 159.3, 161.2, 162.8. MS (ionspray): m/z 379 ($M^+$+1). Anal. calculated for $C_{22}H_{22}N_2O_4$: C, 69.83; H, 5.86; N, 7.40. Found: C, 69.61; H, 5.97; N, 7.32.

2-([5,7-Dimethoxy-3-(4-methoxyphenyl)-2-quinolinyl]oxy)-butanenitrile (Compound 40a)

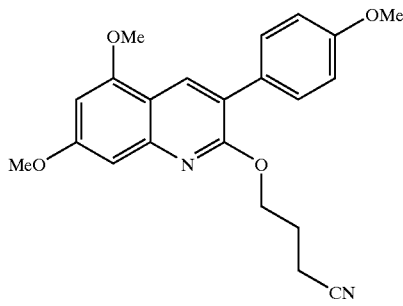

Compound 40a:

m.p. 89–90° C. (EtOAc); IR (KBr) n 1624, 1607, 1582, 1515 $cm^{-1}$; $^1H$ NMR (250 MHz, $CDCl_3$): d 2.12–2.22 (m, 2H, $CH_2$), 2.50 (t, 2H, J=7.5 Hz, $CH_2$), 3.87 (s, 3H, $OCH_3$), 3.94 (s, 6H, $OCH_3$), 4.61 (t, 2H, J=7.5 Hz, $CH_2$), 6.40 (d, 1H, J=2.2 Hz, $H_{Ar}$), 6.81 (d, 1H, J=2.2 Hz, $H_{Ar}$), 6.97 (d, 2H, J=8.8 Hz, $H_{Ar}$), 7.53 (d, 2H, J=8.8 Hz, $H_{Ar}$), 8.27 (s, 1H, $H_{Ar}$). $^{13}C$ NMR (62.9 MHz, $CDCl_3$): d 14.6, 25.4, 55.4, 55.7, 55.8, 63.6, 96.2, 98.6, 113.1, 113.7 (2), 119.5, 122.0, 129.5, 130.5 (2), 132.8, 147.9, 156.4, 159.1, 159.7, 161.6. MS (ionspray): m/z 379 ($M^+$+1); Anal. calculated for $C_{22}H_{22}N_2O_4$: C, 69.83; H, 5.86; N, 7.40. Found: C, 69.99; H, 5.72; N, 7.60.

EXAMPLE 31 a) N-(3,5-Dimethoxyphenyl)-2-(4-benzyloxyphenyl)acetamide (Compound 41)

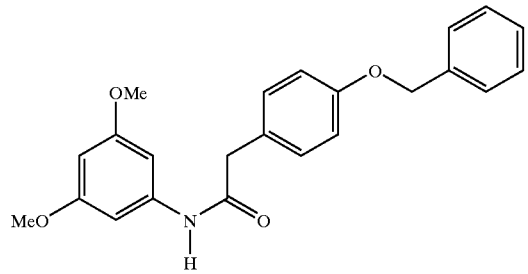

238 mg (1.6 mmol) of 3,5-dimethoxyaniline are dissolved in toluene (7 ml) at 0° C., under a nitrogen atmosphere. A solution of 4-benzylphenylacetyl chloride (0.5 ml, 1.7 mmol) in 5 ml of toluene is added dropwise to the medium. The reaction mixture is stirred at room temperature for 2 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over $MgSO_4$ and then evaporated. The residue obtained is purified by chromatography on a column of silica (4/6 EtOAc/PE) to give 300 mg (81%) of compound 41.

m.p. 122–123° C. (EtOAc/PE); IR (KBr) n 291, 1659, 1610, 1595, 1513 $cm^{-1}$; $^1H$ NMR (250 MHz, $CDCl_3$): d 3.66 (s, 2H, $CH_2$), 3.74 (s, 3H, $OCH_3$), 3.75 (s, 3H, $OCH_3$), 5.08 (s, 2H, $CH_2$), 6.21 (t, 1H, J=2.2 Hz, $H_{Ar}$), 6.65–6.66 (m, 2H, J=2.2 Hz, $H_{Ar}$), 7.00 (d, 2H, J=8.8 Hz, $H_{Ar}$), 7.08 (s, 1H, NH), 7.24 (d, 2H, J=8.8 Hz, $H_{Ar}$), 7.33–7.46 (m, 5H, $H_{Ar}$). $^{13}C$ NMR (62.90 MHz, $CDCl_3$): d 44.2, 55.5 (2), 70.2, 96.9, 98.0 (2), 115.7 (2), 126.6, 127.6 (2), 128.2,128.8 (2), 130.8 (2), 136.9, 139.6, 158.4, 161.1 (2), 169.7. MS (ionspray): 378 (M$^+$+1); Anal. calculated for $C_{23}H_{23}NO_4$: C, 73.19; H, 6.14; N, 3.71. Found: C, 72.87; H, 5.97; N, 3.85.

b) 5,7-Dimethoxy-3-(4-benzyloxyphenyl)-1,2-dihydro-2-quinolinone (Compound 42)

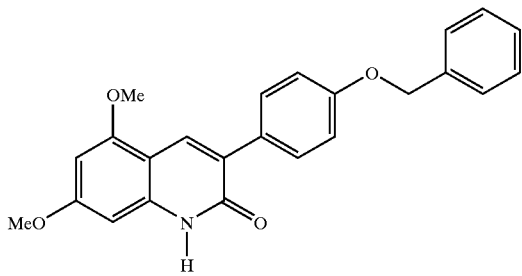

0.31 ml (4.0 mmol, 1.5 eq) of N,N-dimethylformamide is added dropwise to 1.75 ml (19 mmol, 7.5 eq) of POCl$_3$, under a nitrogen atmosphere and at −30° C. The medium is stirred for 15 min at −30° C. and 1.02 g of amide 41 (2.7 mmol) are then added. The reaction mixture is warmed to room temperature with stirring and the reaction is then heated at 75° C. for 1.5 h. At the end of the reaction, this solution is poured onto crushed ice, neutralized with aqueous 30% ammonia solution and then extracted with dichloromethane. The organic phase is dried over MgSO$_4$ and then evaporated. The residue obtained is dissolved in 4.75 ml of glacial acetic acid and 0.15 ml of water and the final solution is then refluxed for 3 h. The acetic acid is evaporated off. The residue is dissolved in water, neutralized with 25% sodium hydroxide solution and then finally extracted with dichloromethane. The organic phase is dried over MgSO$_4$ and then evaporated under reduced pressure. The residue is taken up in ethyl acetate, which causes precipitation of the final product. The crystals thus obtained are filtered off to give 200 mg (20%) of compound 42.

m.p. 234–235° C. (EtOAc); IR (KBr): n 1629, 1608, 1569, 1515 cm$^{-1}$; $^1$H NMR (250 MHz, DMSO-d$_6$): d 3.81 (s, 3H, OCH$_3$), 3.90 (s, 3H, OCH$_3$), 5.15 (s, 2H, CH$_2$), 6.37 (s, 1H, He), 6.45 (s, 1H, H$_{Ar}$), 7.04 (d, 2H, J=8.8 Hz, H$_{Ar}$), 7.31–7.49 (m, 5H, H$_{Ar}$), 7.69 (d, 2H, J=7.5 Hz, H$_{Ar}$), 7.97 (s, 1H, H$_{Ar}$), 11.76 (broad s, 1H, NH). $^{13}$C NMR (62.90 MHz, DMSO-d$_6$): d 55.4, 55.9, 69.2, 90.0, 93.0, 104.6, 114.3 (2), 126.4, 127.6 (2), 127.8, 128.4 (2), 129.2, 129.6 (2), 130.2, 137.1, 140.5, 156.6, 157.7, 161.5, 161.9. MS (ionspray): m/z 388 (M$^+$+1); Anal. calculated for $C_{24}H_{21}NO_4$: C, 74.40; H, 5.46; N, 3.62. Found: C, 74.26; H, 5.67; N, 3.52.

EXAMPLE 32 a) N-(4-Methoxyphenyl)-2-phenylacetamide (Compound 43)

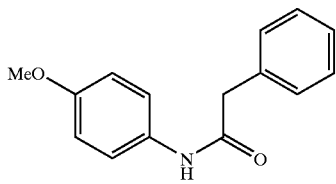

1.5 g (12.0 mmol) of p-anisidine are dissolved in toluene (7 ml) at 0° C., under a nitrogen atmosphere. A solution of phenylacetyl chloride (1.61 ml, 12.2 mmol) in 20 ml of toluene is added dropwise to the medium. The reaction mixture is stirred at room temperature for 2 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over MgSO$_4$ and then evaporated. The residue obtained is purified by chromatography on a column of silica (3/7 EtOAc/PE) to give 2.6 g (89%) of compound 43.

m.p. 118–119° C. (EtOAc/PE); IR (KBr): n 3290, 1650, 1603, 1545, 1513 cm$^{-1}$; $^1$H NMR (250 MHz, CDCl$_3$): d 3.72 (s, 2H, CH$_2$), 3.77 (s, 3H, OCH$_3$), 6.81 (d, 2H, J=9.0 Hz, H$_{Ar}$), 7.00 (broad s, 1H, NH), 7.28–7.43 (m, 7H, H$_{Ar}$). $^{13}$C NMR (62.90 MHz, CDCl$_3$): dδ. 44.8, 55.6, 114.2 (2), 121.9 (2), 127.7, 129.3 (2), 129.7 (2), 130.8, 134.7, 156.7, 169.1. MS (ionspray): 242 (M$^+$+1); Anal. calculated for $C_{15}H_{15}NO_2$: C, 74.67; H, 6.27; N, 5.80. Found: C, 74.79; H, 6.14; N, 5.95.

b) 6-Methoxy-3-phenyl-1,2-dihydro-2-quinolinone (Compound 44)

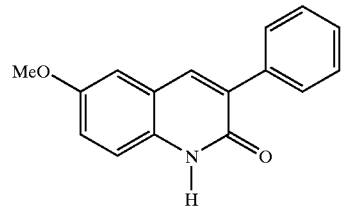

0.96 ml (12.4 mmol, 1.5 eq) of N,N-dimethylformamide is added dropwise to 5.4 ml (58 mmol, 7.5 eq) of POCl$_3$, under a nitrogen atmosphere and at −30° C. The medium is stirred for 15 min at −30° C. and 2.0 g of amide 43 (8.3 mmol) are then added. The reaction mixture is warmed to room temperature with stirring and the reaction is then heated at 75° C. for 1.5 h. At the end of the reaction, this solution is poured onto crushed ice, neutralized with aqueous 30% ammonia solution and then extracted with dichloromethane. The organic phase is dried over MgSO$_4$ and then evaporated. The residue obtained is dissolved in 12.2 ml of glacial acetic acid and 0.4 ml of water and the final solution is then refluxed for 3 h. The acetic acid is evaporated off. The residue is dissolved in water, neutralized with 25% sodium hydroxide solution and then finally extracted with dichloromethane. The organic phase is dried over MgSO$_4$ and then evaporated under reduced pressure. The residue is taken up in ethyl acetate, which causes precipitation of the final product. The crystals thus obtained are filtered off to give 585 mg (28%) of compound 44.

m.p. 243–244° C. (EtOAc); IR (KBr) n 1645, 1618, 1569, 1503 cm$^{-1}$; $^1$H NMR (250 MHz, DMSO-d$_6$): d 3.80 (s, 3H, OCH$_3$), 7.16 (dd, 1H, J=2.5, 8.9 Hz, H$_{Ar}$), 7.28 (d, 1H, J=8.9 Hz, H$_{Ar}$), 7.29 (d, 1H, J=2.5 Hz, H$_{Ar}$), 7.34–7.47 (m, 3H, H$_{Ar}$), 7.76 (d, 2H, J=6.8 Hz, H$_{Ar}$), 8.06 (s, 1H, H$_{Ar}$), 11.85 (broad s, 1H, NH). $^{13}$C NMR (62.90 MHz, DMSO-d$_6$): d 55.4, 109.4, 116.0, 119.5, 120.1, 127.8, 127.9 (2), 128.7 (2), 131.9, 132.9, 136.4, 137.2, 154.2, 160.6. MS (ionspray): m/z 252 (M$^+$+1); Anal. calculated for $C_{16}H_{13}NO_2$: C, 76.48; H, 5.21; N, 5.57. Found: C, 76.16; H, 5.11; N, 5.66.

EXAMPLE 33

5,7-Dimethoxy-3-(4-trifluoromethanesulfonylphenyl)-1,2-dihydro-2-quinolinone (Compound 45)

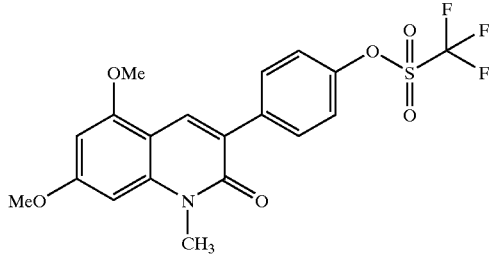

170 mg (0.55 mmol) of compound 8 are dissolved in triflic anhydride and pyridine (8 ml, v/v) at 0° C., under a nitrogen atmosphere. The reaction mixture is stirred at room temperature for 2 h. The medium is hydrolyzed by addition of water (10 ml) and is then extracted with dichloromethane (twice). The organic phase is dried over MgSO$_4$ and then evaporated. The residue obtained is purified by chromatography on a column of silica (1/9 EtOAc/CH$_2$Cl$_2$) to give 194 mg (80%) of compound 45.

m.p. 144–145° C. (EtOAc); IR (KBr): n 1646, 1618, 1602, 1504 cm$^{-1}$; $^1$H NMR (250 MHz, CDCl$_3$): d 3.75 (s, 3H, NCH$_3$), 3.94 (s, 6H, CH$_3$), 6.32 (d, 1H, J=2.0 Hz, H$_{Ar}$), 6.39 (d, 1H, J=2.0 Hz, H$_{Ar}$), 7.30 (d, 2H, J=8.8 Hz, H$_{Ar}$), 7.82 (d, 2H, J=8.8 Hz, H$_{Ar}$), 8.19 (s, 1H, H$_{Ar}$). $^{13}$C NMR (62.90 MHz, CDCl$_3$): d 30.5, 55.8, 56.0, 90.4, 93.0, 106.0, 121.0 (2), 125.3, 130.9 (3), 132.1, 138.1, 148.9, 158.0, 161.8, 163.2. MS (ionspray): m/z 444 (M$^+$+1).

EXAMPLE 34

5,7-Dimethoxy-3-(4-acetylphenyl)-1,2-dihydro-2-quinolinone (Compound 46)

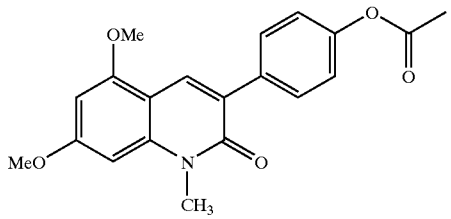

200 mg (0.64 mmol) of compound 8 are dissolved in acetic anhydride and pyridine (8 ml, v/v) at 0° C., under a nitrogen atmosphere. The reaction mixture is stirred at room temperature for 18 h. The medium is hydrolyzed by addition of water (10 ml) and is then extracted with dichloromethane (twice). The organic phase is dried over MgSO$_4$ and then evaporated. The residue obtained is purified by chromatography on a column of silica (1/9 EtOAc/CH$_2$Cl$_2$) to give 165 mg (73%) of compound 46.

m.p. 148–149° C. (EtOAc/PE); IR (KBr): n 1751, 1639, 1601, 1508 cm$^{-1}$; $^1$H NMR (250 MHz, CDCl$_3$): d 2.31 (s, 3H, CH$_3$), 3.72 (s, 3H, NCH$_3$), 3.90 (s, 6H, CH$_3$), 6.28 (d, 1H, J=2.0 Hz, H$_{Ar}$), 6.34 (d, 1H, J=2.0 Hz, H$_{Ar}$), 7.13 (d, 2H, J=8.8 Hz, H$_{Ar}$), 7.75 (d, 2H, J=8.8 Hz, H$_{Ar}$), 8.15 (s, 1H, H$_{Ar}$). $^{13}$C NMR (62.90 MHz, CDCl$_3$): d 21.3, 30.4, 55.7, 55.9, 90.3, 92.7, 106.0, 121.1 (2), 126.3, 130.1 (3), 131.4, 142.1, 150.1, 157.8, 162.0, 162.7, 169.6. MS (ionspray): m/z 354 (M$^+$+1); Anal. calculated for C$_{20}$H$_{19}$NO$_5$: C, 67.98; H, 5.42; N, 3.96. Found: C, 68.23; H, 5.56; N, 3.79.

EXAMPLE 35 a) N-(4-Methylphenyl)-2-phenylacetamide (47)

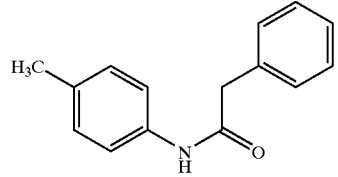

1.0 g (9.3 mmol) of 4-methylaniline is dissolved in toluene (10 ml) at 0° C., under a nitrogen atmosphere. A solution of phenylacetyl chloride (1.25 ml, 9.4 mmol) in 20 ml of toluene is added dropwise to the medium. The reaction mixture is stirred at room temperature for 2 h and the medium is then hydrolyzed with cold sodium hydrogen carbonate solution. The two-phase system is stirred vigorously for 30 min and the organic phase is then collected. The aqueous phase is extracted with ethyl acetate (twice). The organic phase is dried over MgSO$_4$ and then evaporated. The residue obtained is purified by chromatography on a column of silica (3/7 EtOAc/PE) to give 1.9 g (92%) of compound 47.

m.p. 119–120° C. (EtOAc); IR (KBr) n 3310, 1657, 1604, 1536, 1514 cm$^{-1}$; $^1$H NMR (250 MHz, CDCl$_3$): d 2.28 (s, 3H, CH$_3$), 3.70 (s, 2H, CH$_2$), 7.06 (d, 1H, J=8.5 Hz, H$_{Ar}$), 7.25–7.38 (m, 9H, H$_{Ar}$). $^{13}$C NMR (62.90 MHz, CDCl$_3$): d 21.0, 44.9, 120.1 (2), 127.7, 129.3 (2), 129.5 (2), 129.6 (2), 134.2, 134.7, 135.2, 169.2. MS (ionspray): 226 (M$^+$+1); Anal. calculated for C$_{15}$H$_{15}$NO: C, 79.97; H, 6.71; N, 6.22. Found: C, 80.23; H, 6.87; N, 6.11.

b) 6-Methyl-3-phenyl-1,2-dihydro-2-quinolinone (48)

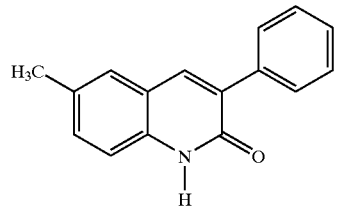

0.41 ml (5.3 mmol, 1.5 eq) of N,N-dimethylformamide is added dropwise to 3.3 ml (25 mmol, 7 eq) of POCl$_3$, under a nitrogen atmosphere and at −30° C. The medium is stirred for 15 min at −30° C. and 800 mg of amide 47 (3.5 mmol) are then added. The reaction mixture is warmed to room temperature with stirring and the reaction is then heated at 75° C. for 1.5 h. At the end of the reaction, this solution is poured onto crushed ice, neutralized with aqueous 30% ammonia solution and then extracted with dichloromethane. The organic phase is dried over MgSO$_4$ and then evaporated. The residue obtained is dissolved in 5.4 ml of glacial acetic acid and 0.2 ml of water and the final solution is then refluxed for 3 h. The acetic acid is evaporated off. The residue is dissolved in water, neutralized with 25% sodium hydroxide solution and then finally extracted with dichloromethane. The organic phase is dried over MgSO$_4$ and then evaporated under reduced pressure. The residue is taken up in ethyl acetate, which brings about precipitation of the final product. The crystals thus obtained are filtered off to give 80 mg (10%) of compound 48.

m.p. 212–213° C. (EtOAc); IR (KBr): n 1657, 1570 cm$^{-1}$; $^1$H NMR (250 MHz, DMSO-d$_6$): d 2.35 (s, 3H, CH$_3$), 7.25 (d, 1H, J=8.5 Hz, H$_{Ar}$), 7.33–7.48 (m, 5H, H$_{Ar}$), 7.51 (broad s, 1H, H$_{Ar}$), 7.76 (d, 2H, J=8.9 Hz, H$_{Ar}$), 8.02 (s, 1H, H$_{Ar}$), 11.87 (broad s, 1H, NH). $^{13}$C NMR (62.90 MHz, DMSO-d$_6$): d 20.5, 114.6, 119.5, 127.6, 127.8, 127.9 (2), 128.7 (2), 130.8, 131.5 (2), 136.4 (2), 137.4, 160.9. MS (ionspray): m/z 236 (M$^+$+1); Anal. calculated for C$_{16}$H$_{13}$NO: C, 81.68; H, 5.57; N, 5.95. Found: C, 81.78; H, 5.39; N, 6.11.

Results of pharmacological tests demonstrating the properties of the compounds of formula I and Ia, either alone or in combination with cytotoxic agents, will be given below.

1—Interaction (Stimulation or Inhibition of Proliferation) With the Generation of Clonogenic Cells (Clonogenic Test)

The test used is that described by Hamburger et al. (Science, 1977; 197, 461–463) and Salmon et al. (New England J. Med., 298, 1321–1327). A cell is considered clonogenic if it has the capacity to proliferate and to give rise to a cell colony. "Human tumor stem cells" are the cells which are the source of the neoplastic cells which constitute a given tumor. These tumor stem cells are responsible for the relapse processes which may be observed after surgical resection of primary tumors and are also responsible for the formation of metastases. In a tumor or a tumor cell line, these clonogenic stem cells differ from the other cells of the tumor or from the neoplastic cell line under consideration in that they conserve their capacity to proliferate in the absence of any solid support.

In this test, the tumor cells are cultured on a semi-solid support consisting of agar. Only the cells which do not require a solid support on which to grow (i.e. the highly tumorigenic cells know as "anchorage-independent cells" by M. I. Dawson et al., Cancer Res. 1995; 55: 4446–4451; also known as clonogenic cells with reference to "clonal growth") are capable of growing on such an agar-based support. Specifically, on such a medium, the normal cells—which grow in "adherent mode" ("anchorage-dependent cells" according to the terminology by M. I. Dawson)—such as, for example, the fibroblasts, do not survive. In a tumor cell population, cultured on such a support, it is these clonogenic cells (associated with an unlimited number of cell divisions and whose proliferation is referred to by M. I. Dawson as "anchorage-independent [clonal] growth") which are capable of growing. The percentage of these clonogenic cells in a tumor or a cell line ranges between 0.1% and 0.001%. The non-clonogenic cells (associated with a limited number of cell divisions) do not grow in this test since they require a solid support on which to grow, which must take place in "adherent mode" ("anchorage-dependent [adherent] growth" according to M. I. Dawson et al., Cancer Res. 1995; 55: 4446–51).

The influence of the compounds of formulae (I) and (Ia) on the growth of the cell colonies obtained by culturing, for example, the mammalian tumor lines MCF7 and MXT and the colorectal line HT-29 on the semi-liquid culture medium known as "soft agar" was measured. On such a medium, only the clonogenic cells referred to by M. I. Dawson as "anchorage-independent (clonal) cells" survive and grow. The growth of these cells in such a "non-adherent" mode bears witness to their degree of tumorigenicity. The inhibition of the growth of the size of a tumor in which a larger number of clonogenic cells has developed then becomes the evidence of reinforced cytotoxic activity.

Conversely, this test can also reveal that a compound is capable of inhibiting the generation/proliferation of clonogenic cells, thus making the tumor less able to grow and thus reducing the population of tumor cells.

The tumor cell lines studied are maintained in culture in 25 cm$^2$ falcon dishes. They are then trypsinized and the cells are fully dissociated from each other. The percentage of live cells is determined after staining with trypan blue. A cell suspension at a concentration of from 5·10$^4$ to 15·10$^4$ cells/ml (depending on the cell type under consideration) is prepared in a 0.3% agar solution. Next, 200 µl of this suspension are inoculated in Petri dishes 35 mm in diameter, in which are placed 3 ml of a base layer consisting of a 0.5% agar solution. The 200 µl of cell suspension are in turn covered with 1.8 ml of an upper layer consisting of a 0.3% agar solution. The dishes are then placed in an incubator at 37° C., 5% CO$_2$ and 70% humidity until the treatment. This treatment is carried out about 1 to 2 hours after the inoculation. The test compounds are prepared at a concentration 100 times greater than the desired concentration and 50 µl of these treating solutions are placed over the upper layer of agar in the corresponding dishes. In the present study, the final concentration of the test products is 10$^{-5}$, 10$^{-7}$ and 10$^{-9}$ M. The dishes are then kept in an incubator for 21 days. On the 21st day the dishes are treated by depositing on the upper layer 100 µl of a 1 mg/ml solution of MTT (3-(4,5-dimethylthiazol-2-yl)-2,5-diphenyltetrazolinium bromide prepared with RPMI 1640 medium) for 3 h at 37° C. After this period, the cell colonies are fixed by adding 2 ml of formalin per dish. After fixing for 24 hours, the formalin is evaporated off and the number of stained cell colonies, thus consisting of metabolically active cells, and whose surface area is greater than 100 µm$^2$, is determined using an inverted microscope.

The average number of clones of clonogenic cells determined for each experimental condition studied is expressed as a percentage relative to the average number of clones of clonogenic cells counted under the control condition set equal to 100%. These values, expressed as a percentage relative to the control condition for all of the test products, are given in Table I.

TABLE I

| | CLONOGENIC TESTS | | | | | |
|---|---|---|---|---|---|---|
| CELL LINES | 10$^{-5}$ | 10$^{-7}$ | 10$^{-9}$ | 10$^{-5}$ | 10$^{-7}$ | 10$^{-9}$ |
| | CRL8315 | | | CRL8316 | | |
| MCF7 | 119.6 ± 5.6 * | 127 ± 8.8 * | 157.1 ± 12.2 ** | 23.2 ± 1.8 *** | 84 ± 5 * | 83.4 ± 4.6 * |
| HT-29 | 103.5 ± 4.5 NS | 111.9 ± 5.4 NS | 112.9 ± 2.4 * | 50.6 ± 1.8 *** | 80.1 ± 2.9 ** | 101.6 ± 3.2 NS |
| MXT | 76 ± 2.3 ** | 103.9 ± 4.3 NS | 102.4 ± 3.9 NS | 10.8 ± 0.5 *** | 89.1 ± 3.7 NS | 95.3 ± 3.8 NS |

TABLE I-continued

CLONOGENIC TESTS

| CELL LINES | $10^{-5}$ | $10^{-7}$ | $10^{-9}$ | $10^{-5}$ | $10^{-7}$ | $10^{-9}$ |
|---|---|---|---|---|---|---|
| | CRL8246 | | | CRL8256 | | |
| MCF7 | 126.8 ± 9.9 * | 145.7 ± 8.9 ** | 139.1 ± 6.6 ** | 51.6 ± 3.7 *** | 83.8 ± 3.4 * | 97.9 ± 5.6 NS |
| HT-29 | 70.9 ± 2.8 ** | 103.3 ± 3.6 NS | 104 ± 2.7 NS | 97.1 ± 4.3 NS | 100.5 ± 4.1 NS | 107.5 ± 3.7 NS |
| MXT | 96.7 ± 7.2 NS | 97.7 ± 9.3 NS | 95.2 ± 6.8 NS | 53 ± 1.9 *** | 103.8 ± 3.9 NS | 104.5 ± 4.7 NS |
| | CRL8247 | | | CRL8283 | | |
| MCF7 | 51.5 ± 2.8 *** | 81.9 ± 1.2 ** | 98.3 ± 4.2 NS | 56.5 ± 4.9 *** | 106.2 ± 4.8 NS | 97.4 ± 5.8 NS |
| HT-29 | 72.7 ± 3.6 ** | 98.3 ± 4.9 NS | 104.5 ± 2.7 NS | 88.9 ± 0.2 ** | 90.9 ± 3.1 NS | 106.1 ± 1.4 NS |
| MXT | 65.7 ± 1.7 *** | 89.6 ± 4.9 NS | 98.4 ± 2.6 NS | 23.7 ± 1.4 *** | 81.2 ± 3 ** | 91.4 ± 4 NS |

Concentrations expressed in mol.l$^{-1}$
The results summarized in this table represent the average values ± standard error of mean (SEM) established on at least 6 cupules
Control condition = 100%
(NS: $p > 0.05$; *: $p < 0.05$; : $p < 0.01$; *: $p < 0.001$).

Thus, since they act on the clonogenic behavior of the tumor, the compounds of formulae (I) and (Ia):
- either increase (e.g.: CRL 8315)—relative to the reference situation [culture media not supplemented with the compounds of formula (I) or (Ia)]—the average number of clones of clonogenic cells, consequently making a larger number of the tumor cells sensitive to the cytotoxic agent (since the clonogenic cells are more sensitive to cytotoxic agents during their proliferation phase),
- or reduce (e.g.: CRL 8283) the number of clonogenic cells by direct toxicity (resulting, here also, in regression of the tumor).

2—Cytotoxic Activity on Non-clonogenic Cells: "MTT Test"

The influence of the compounds of formulae (I) and (Ia) on non-clonogenic cells was evaluated with the aid of the MTT calorimetric test.

The principle of the MTT test is based on the mitochondrial reduction, by the metabolically active live cells, of the yellow-colored product MTT (3-(4,5-dimethylthiazol-2-yl)-2,5-diphenyltetrazolium bromide) to a blue-colored product, formazan. The amount of formazan thus obtained is directly proportional to the amount of live cells present in the culture well(s). This amount of formazan is measured by spectrophotometry.

The cell lines are maintained as a monolayer culture at 37° C. in stoppered culture dishes containing MEM 25 MM HEPES (Minimum Essential Medium) base medium. This medium is suited to the growth of a range of various mammalian diploid or primary cells. This medium is then supplemented with:
- an amount of 5% of FCS (Foetal Calf Serum) decomplemented at 56° C. for 1 hour,
- 0.6 mg/ml of L-glutamine,
- 200 UI/ml of penicillin,
- 200 μg/ml of streptomycin,
- 0.1 mg/ml of gentamicin.

The 12 human cancer cell lines which were used were obtained from the American Type Culture Collection (ATCC, Rockville, Md., USA). These 12 cell lines are:
- U-373MG (code ATCC: HTB-17) and U-87MG (code ATCC: HTB-14) which are two glioblastomas,
- SW1088 (code ATCC: HTB-12) which is an astrocytoma,
- A549 (code ATCC: CCL-185) and A-427 (code ATCC: HTB-53) which are two non-small-cell lung cancers,
- HTC-15 (code ATCC: CCL-225) and LoVo (code ATCC: CCL-229) which are two colorectal cancers,
- T-47D (code ATCC: HTB-133) and MCF7 (code ATCC: HTB-22) which are two breast cancers,
- J82 (code ATCC: HTB-1) and T24 (code ATCC: HTB-4) which are two bladder cancers,
- PC-3 (code ATCC: CRL-1435) which is a prostate cancer.

Experimentally: 100 μl of a cell suspension containing 20 000 to 50 000 (depending on the cell type used) cells/ml of culture medium are inoculated in 96-well flat-bottomed multi-well plates and are incubated at 37° C., under an atmosphere comprising 5% $CO_2$ and 70% humidity. After incubation for 24 hours, the culture medium is replaced with 100 μl of fresh medium containing either the various test compounds at concentrations ranging from $10^{-5}$ to $10^{-10}$ M or the solvent used to dissolve the test products (control condition). After incubation for 72 hours under the above conditions, the culture medium is replaced with 100 μl of a yellowish solution of MTT dissolved at a rate of 1 mg/ml in RPMI 1640. The microplates are reincubated for 3 hours at 37° C. and are then centrifuged for 10 minutes at 400×g. The yellowish solution of MTT is removed and the blue formazan crystals formed in the cell are dissolved in 100 μl of DMSO. The microplates are then shaken for 5 minutes. The intensity of the resulting blue coloration, and thus of the conversion of the yellow product MTT into blue formazan by the cells that are still alive at the end of the experiment, is quantified by spectrophotometry using a Dynatech Immunoassay System machine at wavelengths of 570 nm and 630 nm corresponding, respectively, to the maximum absorption wavelengths of formazan and to the background noise. Software incorporated in the spectrophotometer calculates the average optical density values and the standard deviation (SD) and standard error of mean (SEM) values.

By way of example, the results of the average optical density, expressed as a percentage relative to the average optical density measured under the control condition (set equal to 100%), obtained at a concentration of $10^{-5}$ M on the 12 abovementioned tumor cell lines are given in Table II.

TABLE IIa

| 2-QUINOLONES | CELL LINES | | | | | | |
|---|---|---|---|---|---|---|---|
| | U-87MG | U-373MG | SW1088 | T24 | J82 | HCT-15 | LoVo |
| CRL8246 | 92.1 ± 1.5 * | 96.6 ± 1.2 NS | 107.6 ± 1.1 ** | 109.4 ± 3.5 NS | 87.6 ± 2.2 ** | 97.2 ± 5.1 NS | 108.8 ± 7 NS |
| CRL8284 | 88.1 ± 2.2 * | 87.7 ± 1.4 *** | 78.3 ± 1.6 *** | 68.5 ± 0.9 *** | 48.8 ± 0.7 *** | 77.3 ± 1.8 *** | 101.7 ± 1.3 NS |
| CRL8311 | 91.8 ± 1.3 NS | 113.3 ± 2.5 ** | 80.7 ± 1.7 *** | 90 ± 1.9 ** | 127 ± 1.9 *** | 101.2 ± 3.6 NS | 77.9 ± 1.7 *** |
| CRL8271 | 78.5 ± 1.7 *** | 96.2 ± 1.6 NS | 102.2 ± 0.5 NS | 107.4 ± 2.3 * | 75.9 ± 1.3 *** | 87.2 ± 2.8 ** | 94.2 ± 2.8 NS |
| CRL8244 | 97 ± 1 NS | 69 ± 0.9 *** | 81.3 ± 1.1 *** | 88.7 ± 2.9 *** | 88.5 ± 2.1 ** | 76.8 ± 3.0 *** | 78.2 ± 1.8 *** |
| CRL8321 | 96.5 ± 1.2 NS | 97.1 ± 2.4 NS | 97.2 ± 1.8 NS | 103.1 ± 1.7 NS | 88.6 ± 0.9 *** | 118.3 ± 1.6 *** | 107.8 ± 1.1 ** |
| CRL8245 | 58.6 ± 1.7 *** | 63.7 ± 2.7 *** | 75.1 ± 2 *** | 51.1 ± 1.9 *** | 31.1 ± 0.6 *** | 35.8 ± 1.2 *** | 65.5 ± 1.1 *** |
| CRL8314 | 74.5 ± 3.4 *** | 89.2 ± 2 ** | 85.4 ± 2.5 *** | 61.9 ± 2.5 *** | 33.2 ± 1.2 *** | 116.5 ± 4.4 * | 82.9 ± 2.5 ** |
| CRL8318 | 78.1 ± 2.4 *** | 89.9 ± 1.3 ** | 75.2 ± 3 *** | 81.8 ± 1.4 *** | 72.8 ± 1.2 *** | 113 ± 1.7 *** | 75.2 ± 2.3 *** |
| CRL8317 | 91 ± 4.1 NS | 91.2 ± 1.9 ** | 103.4 ± 2.3 NS | 91.4 ± 4.3 NS | 83.6 ± 1.8 *** | 103.6 ± 2.6 NS | 86.8 ± 2.8 ** |
| CRL8319 | 115 ± 2.9 * | 101.7 ± 1.5 NS | 89.8 ± 2.7 NS | 89.6 ± 2.1 ** | 80.9 ± 1 *** | 96.7 ± 1.6 NS | 79.7 ± 2.7 ** |
| CRL8283 | 69.9 ± 3.4 *** | 93.4 ± 1.5 NS | 84.7 ± 3.1 ** | 72.9 ± 0.9 *** | 71.6 ± 2.2 *** | 58.2 ± 4.3 *** | 97.3 ± 3.6 NS |

| 2-QUINOLONES | CELL LINES | | | | |
|---|---|---|---|---|---|
| | MCF7 | T-47D | A549 | A-427 | PC-3 |
| CRL8246 | 98.1 ± 1.4 NS | 96 ± 2.6 NS | 113 ± 2.1 *** | 101 ± 0.9 NS | 121.7 ± 1.7 *** |
| CRL8284 | 66.6 ± 2.7 *** | 89.9 ± 1.9 * | 91.7 ± 1.6 ** | 96 ± 2.0 NS | 83.8 ± 1 *** |
| CRL8311 | 98.8 ± 2.3 NS | 107.6 ± 6.6 NS | 106.1 ± 2.4 NS | 89.7 ± 2.0 ** | 122.1 ± 3.5 ** |
| CRL8271 | 105.5 ± 2.3 NS | 90.9 ± 1.7 ** | 94.2 ± 4.7 NS | 84.1 ± 1.9 ** | 107 ± 2.7 NS |
| CRL8244 | 75.9 ± 3.8 *** | 105 ± 3 * | 98 ± 0.9 NS | 93.6 ± 2.3 NS | 83.2 ± 3.6 ** |
| CRL8321 | 96.6 ± 0.9 * | 91.5 ± 1.2 ** | 99.4 ± 1.3 NS | 107 ± 1.4 ** | 102.2 ± 3.1 NS |
| CRL8245 | 46.9 ± 1 *** | 59.6 ± 2.9 *** | 74.1 ± 2.1 *** | 69 ± 1.9 *** | 74.4 ± 1.9 *** |
| CRL8314 | 72.2 ± 2 *** | 113.5 ± 2.3 * | 85.2 ± 1.4 *** | 104.4 ± 3.1 NS | 88.6 ± 1.4 *** |
| CRL8318 | 105 ± 2.4 NS | 100.3 ± 3.9 NS | 86.6 ± 2.5 ** | 74 ± 3 *** | 79.2 ± 2.8 *** |
| CRL8317 | 96 ± 2.1 NS | 95 ± 2.5 NS | 94.7 ± 2.2 NS | 91.3 ± 2 ** | 97.9 ± 1.1 NS |
| CRL8319 | 101.5 ± 2 NS | 104.5 ± 2.5 NS | 97.3 ± 1.2 NS | 79.1 ± 2.5 *** | 90.7 ± 3.6 NS |
| CRL8283 | 76.2 ± 0.9 * | 81 ± 3.1 * | 63.6 ± 4.2 * | 73.1 ± 1.7 * | 92.4 ± 1.7 * | x ± y = average value ± standard error of mean

Control condition = 100%

(NS: $p > 0.05$; *: $p < 0.05$; : $p < 0.01$; *: $p < 0.001$)

TABLE IIb

| 2-QUINOLONES | U-87MG | U-373MG | SW1088 | T24 | J82 | HCT-15 | LoVo |
|---|---|---|---|---|---|---|---|
| CRL8315 | 87.6 ± 4.5 * | 68.9 ± 2.2 *** | 89.1 ± 0.6 *** | 89.6 ± 2.1 ** | 65.9 ± 1.3 *** | 87.9 ± 3.3 * | 78.9 ± 2.1 *** |
| CRL8254 | 105.1 ± 3.6 NS | 7.6 ± 1.3 *** | 128.3 ± 2.2 *** | 102.6 ± 2.9 NS | 87.8 ± 1 *** | 94.4 ± 3.5 NS | 91.8 ± 2.7 * |
| CRL8255 | 72.5 ± 1.1 *** | 68.5 ± 2.7 *** | 67.5 ± 1.5 *** | 79.5 ± 2.2 *** | 36.2 ± 0.5 *** | 58.7 ± 3 *** | 56.9 ± 1.1 *** |
| CRL8247 | 59 ± 2.3 *** | 68.7 ± 2.8 *** | 85.8 ± 3.6 ** | 77.8 ± 2.7 *** | 55 ± 2.3 *** | 87.4 ± 2.5 * | 66.4 ± 2.5 *** |
| CRL8256 | 84.7 ± 1.7 *** | 76.1 ± 2.6 *** | 72.1 ± 3.3 *** | 78.2 ± 2.6 *** | 77.8 ± 0.8 *** | 73.9 ± 3.6 *** | 93 ± 2.3 NS |
| CRL8316 | 74.3 ± 1.4 *** | 89.8 ± 2.9 * | 106.6 ± 2 * | 94 ± 3.2 NS | 26.9 ± 0.9 *** | 79.8 ± 2.9 ** | 73.9 ± 2.1 *** |
| CRL8285 | 85.1 ± 2 ** | 96.9 ± 1.6 NS | 89.8 ± 2.7 * | 72.7 ± 1.8 *** | 68.7 ± 2.9 *** | 90.6 ± 1.6 * | 102.8 ± 3.1 NS |
| CRL8270 | 75.6 ± 0.9 *** | 52.2 ± 3.2 *** | 50.7 ± 1.8 *** | 51.1 ± 3.8 *** | 42.5 ± 0.8 *** | 58.8 ± 1.8 *** | 80 ± 3.2 *** |
| CRL8366 | 64.4 ± 1.2 *** | 66.3 ± 1.6 *** | 68.4 ± 1.6 *** | 84.6 ± 3 * | 31.2 ± 0.7 *** | 76.1 ± 1.5 *** | 71.3 ± 4.5 *** |
| CRL8336 | 82.3 ± 1.8 *** | 82.3 ± 1.6 *** | 101.1 ± 4.3 NS | 88.2 ± 1.4 *** | 90.9 ± 0.9 ** | 93.1 ± 3.2 NS | 92.6 ± 3.4 NS |
| CRL8330 | 86.6 ± 0.7 *** | 75.5 ± 3.7 *** | 73.3 ± 1.8 *** | 57.4 ± 2.3 *** | 70.5 ± 2.4 *** | 94.7 ± 2.1 NS | 59.9 ± 4.2 *** |
| CRL8339 | 69.1 ± 2.1 *** | 73.6 ± 1.8 *** | 87.1 ± 2.6 ** | 87.4 ± 2 ** | 83.7 ± 0.6 *** | 65.5 ± 2.2 *** | 74.4 ± 1.8 *** |

| 2-QUINOLONES | MCF7 | T-47D | A549 | A-427 | PC-3 |
|---|---|---|---|---|---|
| CRL8315 | 96.2 ± 1.7 NS | 101.3 ± 2.5 NS | 76.1 ± 2.4 *** | 92.6 ± 2.1 * | 93.6 ± 3 NS |
| CRL8254 | 81.9 ± 0.6 *** | 55.2 ± 4.1 *** | 96.9 ± 1.5 NS | 20.2 ± 2.3 *** | 97.9 ± 1.2 NS |
| CRL8255 | 71.5 ± 1.4 *** | 73.7 ± 3.3 *** | 79.1 ± 2.1 *** | 76.3 ± 1.5 ** | 77.7 ± 1.2 *** |
| CRL8247 | 78.9 ± 1.1 *** | 58.3 ± 1.4 *** | 81.3 ± 1.9 *** | 57 ± 1.5 *** | 70.5 ± 4.6 *** |
| CRL8256 | 81.8 ± 1.6 *** | 77.5 ± 3.6 ** | 56.5 ± 3.7 *** | 81.1 ± 2.9 *** | 86 ± 2.3 *** |
| CRL8316 | 78.9 ± 4.0 *** | 68.8 ± 2.4 *** | 84.2 ± 1.9 *** | 79.1 ± 4.8 ** | 84.8 ± 2.3 ** |
| CRL8285 | 83.7 ± 2.3 *** | 89.3 ± 1.7 ** | 92.5 ± 3.5 NS | 78.4 ± 1.6 *** | 93.4 ± 1.8 * |
| CRL8270 | 51.5 ± 2.4 *** | 22.9 ± 4.3 *** | 52.2 ± 2.4 *** | 30.8 ± 2.1 *** | 49.4 ± 1.1 *** |
| CRL8366 | 46.3 ± 2.6 *** | 25 ± 4 *** | 61.6 ± 3.5 *** | 45.2 ± 2.2 *** | 67.2 ± 0.9 *** |
| CRL8336 | 73.9 ± 0.7 *** | 96.2 ± 2.9 NS | 114.2 ± 1.9 *** | 87.9 ± 3.1 ** | 91.7 ± 1.5 *** |
| CRL8330 | 87.2 ± 3 ** | 77.6 ± 3 *** | 76.3 ± 2.4 *** | 59.8 ± 1 *** | 48.5 ± 2.1 *** |
| CRL8339 | 82.7 ± 3.5  | 81 ± 2.8  | 49.6 ± 2.2 * | 52.3 ± 2.3 * | 84.3 ± 1.8 *** | x ± y = average value ± standard error of mean
Control condition = 100%
(NS: $p > 0.05$; *: $p < 0.05$; : $p < 0.01$; *: $p < 0.001$)

It appears that several of the compounds induce a weak inhibition which can be up to 20–30% of the overall cell proliferation of the tumor lines under consideration and that these compounds do not appear to have any tissue specificity.

3.—Determination of the Maximum Tolerated Dose (MTD):

The evaluation of the maximum tolerated dose was carried out on 4- to 6-week-old B6D2F1/Jico mice. The compounds were administered intraperitoneally at increasing doses graduating from 2.5 to 160 mg/kg. The value of the MTD (expressed in mg/kg) is determined from the observation of the survival rate of the animals over a 14-day period after a single administration of the product under consideration. The weight change of the animals is also monitored during this period. When the value of the MTD is greater than 160 mg/kg, the MTD value is likened to 160 mg/kg by default.

The results of the estimation of the maximum tolerated dose (MTD) are collated in the following table:

TABLE III

| Maximum tolerated doses | |
|---|---|
| CRL compounds | MTD (mg/kg) |
| CRL8246 (Example 1) | >160 |
| CRL8284 (Example 2) | >160 |

TABLE III-continued

Maximum tolerated doses

| CRL compounds | MTD (mg/kg) |
|---|---|
| CRL8311 (Example 3) | >160 |
| CRL8271 (Example 4) | >160 |
| CRL8244 (Example 5) | >160 |
| CRL8321 (Example 7) | >160 |
| CRL8245 (Example 8) | >160 |
| CRL8314 (Example 9) | >160 |
| CRL8318 (Example 10) | >160 |
| CRL8317 (Example 12) | >160 |
| CRL8319 (Example 14) | >160 |
| CRL8283 (Example 15) | >160 |
| CRL8315 (Example 16) | >160 |
| CRL8255 (Example 17) | >160 |
| CRL8247 (Example 18) | >160 |
| CRL8256 (Example 19) | >160 |
| CRL8254 (Example 20) | >160 |
| CRL8316 (Example 21) | >160 |
| CRL8285 (Example 22) | >160 |
| CRL8270 (Example 23) | >160 |
| CRL8266 (Example 24) | >160 |
| CRL8336 (Example 26) | >160 |
| CRL8330 (Example 27) | >160 |
| CRL8339 (Example 28) | >160 |

The products of this family show no direct toxicity and can thus be used in vivo at high tissue concentrations, and thus at high doses.

4.—In Vivo Antitumor Activity in Combination With a Cytotoxic Agent

The tests were carried out on models of:
hormone-sensitive mouse mammary adenocarcinoma MXT (HS-MXT),
lymphoma P 388,
in the presence or absence of cytotoxic agents such as cyclophosphamide, etoposide, doxorubicin or vincristine.

When the MTD value of a product was determined, its in vivo antitumor activity was characterized at doses of MTD/2, MTD/4 and MTD/8 on the model of mouse mammary adenocarcinoma HS-MXT and on the model of lymphoma P 388. The dose which showed the best antitumor activity on these various models was selected and used in the context of combined treatments with the cytotoxic agents.

In all the examples presented below, irrespective of the model (mammary adenocarcinoma HS-MXT or lymphoma P 388), the control condition is represented by a batch of 9 mice to which is administered for 5 consecutive weeks and at a rate of 5 administrations (Monday, Tuesday, Wednesday, Thursday and Friday) per week a volume of 0.2 ml of physiological saline containing the solvent used to dissolve the various compounds of formulae (I) and (Ia) used.

The following parameters were determined in these tests:
i)—The survival rate of the mice
This survival rate was calculated in the form of a ratio T/C:

$$T = \frac{\text{(Number of days of survival of the median mouse in the batch of mice tested)} + \text{(Number of mice which died in the days preceding that of the median mouse treated)}}{\text{(Number of mice which died on the same day as the median mouse treated)}}$$

$$C = \frac{\text{(Number of days of survival of the median mouse in the batch of control mice)} + \text{(Number of mice which died in the days preceding that of the median mouse treated)}}{\text{(Number of mice which died on the same day as the median control mouse)}}$$

This ratio represents the average survival time of the median mouse from the batch of treated mice relative to the average survival time of the median mouse from the batch of control mice. Thus, a molecule induces a significant (P<0.05) increase in the survival of the animals when the index T/C exceeds 130%. Conversely, it has a toxic effect when this value of T/C is less than 70%.

ii)—The tumor growth [lacuna] by measuring the area of the grafted HS-MXT or P 388 tumors twice a week (Monday and Friday). This area is calculated by multiplying the values of the largest two perpendicular axes of the tumor. The value of these axes is measured using a sliding caliper.

4.1. Mouse Mammary Adenocarcinoma (HS-MXT)

The model of hormone-sensitive MXT (HS-MXT) mouse mammary adenocarcinoma grafted onto 4- to 6-week-old B6D2F1/JIco mice is derived from the milk ducts of the mammary gland (Watson C. et al. Cancer Res. 1977; 37: 3344–48).

The results obtained using compounds 1 and 20, either alone or in combination with the cytotoxic agents, will be given by way of example.

A—Compound 1 or CRL 8246:

Treatments 1 and 1a

Compound 1 is administered alone. The first injection of the product is carried out on the seventh day post-grafting (D7) for four consecutive weeks at a rate of 5 injections per week (Monday, Tuesday, Wednesday, Thursday and Friday) and at a dose of 20 mg/kg.

Treatment 2

Cyclophosphamide (CPA) is administered alone. The first injection of the product is carried out on the fourteenth day post-grafting (D14) for three consecutive weeks at a rate of 3 injections per week (Monday, Wednesday and Friday) and at a dose of 10 mg/kg.

Treatment 3

Compound 1 is co-administered with cyclophosphamide. In this case, the first injection of compound 1 is carried out on the seventh day post-grafting (D7) for four consecutive weeks at a rate of 5 injections per week (Monday, Tuesday, Wednesday, Thursday and Friday) at a dose of 20 mg/kg, and the first injection of cyclophosphamide is carried out on the fourteenth day post-grafting (D14) for three consecutive weeks at a rate of 3 injections per week (Monday, Wednesday and Friday) at a dose of 10 mg/kg.

Treatment 4

Etoposide (ETO) is administered alone. The first injection of the product is carried out on the fourteenth day post-grafting (D14) for three consecutive weeks at a rate of 3 injections per week (Monday, Wednesday and Friday) and at a dose of 10 mg/kg.

Treatment 5

Doxorubicin (DOX) is administered alone. The first injection of the product is carried out on the fourteenth day post-grafting (D14) for three consecutive weeks at a rate of 3 injections per week (Monday, Wednesday and Friday) and at a dose of 5 mg/kg.

Treatment 6

Compound 1 is co-administered with etoposide. In this case, the first injection of compound 1 is carried out on the seventh day post-grafting (D7) for four consecutive weeks at a rate of 5 injections per week (Monday, Tuesday, Wednesday, Thursday and Friday) at a dose of 20 mg/kg and the first injection of etoposide is carried out on the fourteenth day post-grafting (D14) for three consecutive weeks at a rate of 3 injections per week (Monday, Wednesday and Friday) at a dose of 10 mg/kg.

Treatment 7

Compound 1 is co-administered with doxorubicin.

In this case, the first injection of compound 1 is carried out on the seventh day post-grafting (D7) for four consecutive weeks at a rate of 5 injections per week (Monday, Tuesday, Wednesday, Thursday and Friday) at a dose of 20 mg/kg, and the first injection of adriamycin is carried out on the fourteenth day post-grafting (D14) for three consecutive weeks at a rate of 3 injections per week (Monday, Wednesday and Friday) at a dose of 5 mg/kg.

The results obtained regarding the survival time for compound 1 are given in Tables IV and V:

TABLE IV

| Treatments | T/C (expressed as %) |
| --- | --- |
| 1 (Compound 1) | 100 |
| 2 (CPA) | 122 |
| 3 (Compound 1 + CPA) | 135 |

TABLE V

| Treatments | T/C (expressed as %) |
| --- | --- |
| 1a (Compound 1) | 95 |
| 4 (ETO) | 130 |
| 5 (DOX) | 92.5 |
| 6 (Compound 1 + ETO) | 150 |
| 7 (Compound 1 + DOX) | 145 |

These results show that the co-administration of compound 1 with the cytotoxic agents: cyclophosphamide, etoposide or doxorubicin, significantly increases the average survival time of the median mouse from the various batches of mice thus treated, relative to the average survival time of the median mouse from the batch of control mice. Furthermore, this increase in the average survival time of the median mouse from the various batches of mice treated with these co-administrations is significantly longer than that obtained with the treatments involving these cytotoxic agents used alone.

The study of the tumor growth moreover revealed the following results for compound 1. Table VI below indicates, in percentages, the reductions (−) or increases (+) of the area of the HS-MXT tumors induced with the various treatments 1, 2 and 3 of Example 1, compared with the control condition on the 31st day after the tumor graft, i.e. after 19 administrations of compound 1 and 8 administrations of cyclophosphamide, used in co-administration or otherwise. On the 31st day post-grafting, 89% of the control animals are still alive (i.e. 8 out of the 9 animals).

TABLE VI

| Treatments | Tumor area (expressed as %) |
| --- | --- |
| 1 (Compound 1) | −19.5 |
| 2 (CPA) | −23.6 |
| 3 (Compound 1 + CPA) | −49.6 |

The results show that the co-administration of compound 1 with cyclophosphamide induces a highly significant reduction in the growth of the HS-MXT tumors, which is greater than the reduction induced by the treatments involving compound 1 or cyclophosphamide used alone.

B—Compound 21 or CRL 8256:

Another example, relating to compound 21 used alone or in combination with etoposide.

Treatment 10

Compound 21 is administered alone. The first injection of the product is carried out on the 7th day post-grafting (D7) at a rate of 5 injections per week (Monday, Tuesday, Wednesday, Thursday and Friday) for five consecutive weeks and at a dose of 40 mg/kg.

Treatment 20

Etoposide (ETO) is administered alone. The first injection of the product is carried out on the 7th day post-grafting (D7) at a rate of 3 injections per week (Monday, Wednesday and Friday) for three consecutive weeks and at a dose of 10 mg/kg.

Treatment 30

Compound 21 is co-administered with etoposide. In this case, the first injection of compound 21 is carried out on the 7th day post-grafting (D7) at a rate of 5 injections per week (Monday, Tuesday, Wednesday, Thursday and Friday) for five consecutive weeks at a dose of 40 mg/kg, and the first injection of etoposide is carried out on the 7th day post-grafting (D7) at a rate of 3 injections per week (Monday, Wednesday and Friday) for three consecutive weeks at a dose of 10 mg/kg.

Table VII gives the survival time results obtained with compound 21.

TABLE VII

| Treatments | T/C (expressed as %) |
| --- | --- |
| 10 (Compound 21) | 110 |
| 20 (ETO) | 124 |
| 30 (Compound 21 + ETO) | 138 |

These results show that the co-administration of compound 21 with etoposide induces a significant increase in the average survival time of the median mouse from the batch of mice thus treated, compared with the average survival time of the median mouse from the batch of control mice. Furthermore, this increase in the average survival time of the median mouse from the batch of mice treated with this co-administration is significantly longer than that obtained with the treatments involving this 2-quinolone or this cytotoxic agent used alone.

4.2. Lymphoma P 388

4- to 6-week-old CDF1 mice are grafted with a piece of P 388 tumor (from a tumor bank maintained in the laboratory) subcutaneously into the right flank on day D0. In order to be under conditions close to clinical reality, we waited until the 5th day post-grafting (D5) before starting the treatment. The reason for this was that, after this period of time, the subcutaneous P 388 tumors are palpable.

By way of example, the results obtained with compounds 1 (CRL 8246) and 20 (CRL 8247), alone or in combination with vincristine, are given below.

Treatment 1

Compound 1 is administered alone. The first injection of the product is carried out on the 5th day post-grafting (D5) at a rate of 5 injections per week (Monday, Tuesday, Wednesday, Thursday and Friday) for five consecutive weeks-and at a dose of 40 mg/kg.

Treatment 2

Compound 20 is administered alone. The first injection of the product is carried out on the fifth day post-grafting (D5) at a rate of 5 injections per week (Monday, Tuesday, Wednesday, Thursday and Friday) for five consecutive weeks and at a dose of 40 mg/kg.

Treatment 3

Vincristine (VCR) is administered alone. The first injection of the product is carried out on the fifth day post-grafting (D5) at a rate of 3 injections per week (Monday, Wednesday and Friday) for three consecutive weeks and at a dose of 0.63 mg/kg.

Treatment 4

Compound 1 is co-administered with vincristine. In this case, the first injection of compound CRL8246 is carried out on the fifth day post-grafting (D5) at a rate of 5 injections per week (Monday, Tuesday, Wednesday, Thursday and Friday) for five consecutive weeks at a dose of 40 mg/kg, and the first injection of vincristine is carried out on the fifth day post-grafting (D5) at a rate of 3 injections per week (Monday, Wednesday and Friday) for three consecutive weeks at a dose of 0.63 mg/kg.

Treatment 5

Compound 20 is co-administered with vincristine. In this case, the first injection of compound CRL8247 is carried out on the fifth day post-grafting (D5) at a rate of 5 injections per week (Monday, Tuesday, Wednesday, Thursday and Friday) for five consecutive weeks at a dose of 40 mg/kg, and the first injection of vincristine is carried out on the fifth day post-grafting (D5) at a rate of 3 injections per week (Monday, Wednesday and Friday) for three consecutive weeks at a dose of 0.63 mg/kg.

Table IX shows the results obtained with treatments 1 to 5 mentioned above, on the survival time of the mice.

TABLE IX

| Treatments | T/C (expressed as %) |
| --- | --- |
| 1 (Compound 1) | 120 |
| 2 (Compound 20) | 125 |
| 3 (VCR) | 122 |
| 4 (Compound 1 + VCR) | 144 |
| 5 (Compound 20 + VCR) | 164 |

These results show that the co-administration of compounds 1 and 20 with vincristine produces a highly significant increase in the average survival time of the median mouse from the various batches of mice thus treated, compared with the average survival time of the median mouse from the batch of control mice. Furthermore, this increase in the average survival time of the median mouse from the various batches of mice treated with these co-administrations is significantly longer than that obtained with the treatments involving these two compounds 1 and 20 or vincristine used alone.

Examples of the method for using the compounds of formulae (I) and (Ia) in mono- or polychemotherapy protocols with cytotoxic agents will be given below. In these protocols, the compounds of formulae (I) and (Ia) 5 will be referred to for simplicity as "2-quinolone".

A. Solid Tumors

1/ Lung Cancers 1.1. To Non-small Cells (Advanced Stage)

to the recommended protocol (T. Le Chevalier et al., J. Clin. Oncol. 1994; 12: 360–367) are added intravenous infusions of a 2-quinolone:

| | Dose | Route | Days |
| --- | --- | --- | --- |
| 2-quinolone | 200–2000 mg/m$^2$/day or 5–50 mg/kg/day infusion for 1 h | i.v. | $D_1$, $D_8$, $D_{15}$, $D_{22}$, $D_{29}$ and $D_{36}$ |
| navelbine | 30 mg/m$^2$/day | i.v. | $D_1$, $D_8$, $D_{15}$, $D_{22}$, $D_{29}$ and $D_{36}$ |
| cisplatin | 120 mg/m$^2$ | i.v. | $D_1$ and $D_{29}$ |

This cure is to be repeated 8 times.

1.2. To Small Cells (Advanced Stage)

to the recommended protocol CAV or VAC (B. J. Roth et al., J. Clin. Oncol. 1992; 10: 282–291) are added infusions of 2-quinolone:

| | Dose | Route | Days |
| --- | --- | --- | --- |
| 2-quinolone | 200–2000 mg/m$^2$/day or 5–50 mg/kg/day infusion for 1 h | i.v. | $D_1$ |
| cyclophosphamide | 1000 mg/m$^2$ bolus | i.v. | $D_1$ |
| doxorubicin | 40 to 50 mg/m$^2$ bolus | i.v. | $D_1$ |
| vincristine | 1 to 1.4 mg/m$^2$ bolus (max 2 mg) | i.v. | $D_1$ |

This cure is to be repeated 6 times every 21 days.

To the recommended Pt-E protocol (B. J. Roth et al., J. Clin. Oncol. 1992; 10: 282–291) are added infusions of 2-quinolone.

| | Dose | Route | Days |
| --- | --- | --- | --- |
| 2-quinolone | 200–2000 mg/m$^2$/day or 5–50 mg/kg/day infusion for 1 h | i.v. | $D_1$–$D_5$ |
| cisplatin | 20 mg mg/m$^2$/day infusion for 20 to 60 minutes | i.v. | $D_1$–$D_5$ |
| etoposide | 80 mg/m$^2$/day infusion for 60 minutes | i.v | $D_1$–$D_5$ |

Each cycle is repeated every 21 days and the cure comprises 6 cycles.

1.3. Non-small-cell Bronchial Cancer, Locally Advanced or Metastatic monochemotherapy:

| | Dose | Route | Days |
|---|---|---|---|
| 2-quinolone | 200–2000 mg/m$^2$/day or 5–50 mg/kg/day infusion for 1 h | i.v. | $D_1$, $D_8$, $D_{15}$ and then 1 week/rest |
| gemcitabine | 1000 mg/m$^2$/day infusion for 0.5 hour | i.v. | $D_1$, $D_8$, $D_{15}$ and then 1 week/rest | the cure being able to comprise repetition of this 4-week cycle.

gemcitabine/cisplatin combination:

| | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{15}$ |
| gemcitabine | 1000 mg/m$^2$/day infusion for 0.5 hour | i.v. | $D_1$, $D_8$, $D_{15}$ |
| cisplatin | 20 mg/m$^2$/day infusion for 20–60 minutes | i.v. | $D_1$ | the cure comprising the repetition of this cycle every 21 days.

2/ Breast Cancers

CMF protocol as auxiliary treatment for operable breast cancer (G. Bonnadonna et al., N. Engl. J. Med.; 1976; 294: 405–410):

| | Dose | Route | Days |
|---|---|---|---|
| 2-quinolone | 200–2000 mg/m$^2$/day or 5–50 mg/kg/day infusion for 1 h | i.v. | $D_1$ to $D_{14}$ |
| cyclophosphamide | 100 mg/m$^2$/day | oral | $D_1$ to $D_{14}$ |
| methotrexate | 40 mg/m$^2$ bolus | i.v. | $D_1$ and $D_8$ |
| 5-FU | 600 mg/m$^2$ | i.v. | $D_1$ and $D_8$ | each cycle is repeated every 28 days and the cure comprises 6 cycles.

AC protocol (B. Fisher et al., J. Clin. Oncol.; 1990; 8: 1483–1496) as an auxiliary treatment:

| | Dose | Route | Days |
|---|---|---|---|
| 2-quinolone | 200–2000 mg/m$^2$/day or 5–50 mg/kg/day infusion for 1 h | i.v. | $D_1$ |
| doxorubicin | 60 mg/m$^2$ bolus | i.v. | $D_1$ |
| cyclophosphamide | 600 mg/m$^2$ bolus | i.v. | $D_1$ | each cycle is repeated every 21 days and the cure comprises 4 cycles.

Breast Cancers With Metastasis:

in the FAC protocol (A. U. Buzdar et al., Cancer 1981; 47: 2537–2542) and its various adaptations, the infusions of 2-quinolone are added according to the following (non-limiting) scheme:

| | Dose | Route | Days |
|---|---|---|---|
| 2-quinolone | 200–2000 mg/m$^2$/day or 5–50 mg/kg/day infusion for 1 h | i.v | $D_1$–$D_5$ and $D_8$–$D_{12}$ or $D_1$–$D_5$ |
| 5-FU | 500 mg/m$^2$/day | oral | $D_1$ and $D_8$ or $D_1$–$D_2$ |
| doxorubicin | 50 mg/m$^2$ bolus | i.v. | $D_1$ or $D_1$ and $D_2$ |
| cyclophosphamide | 500 mg/m$^2$ | bolus i.v. or oral | $D_1$ $D_1$ | each cycle is repeated every 3 weeks until a new progression of the disease is diagnosed.

in the CAF protocol (G. Falkson et al., Cancer 1985; 56: 219–224):

| | Dose | Route | Days |
|---|---|---|---|
| 2-quinolone | 200–2000 mg/m$^2$/day or 5–50 mg/kg/day infusion for 1 h | i.v. | $D_1$–$D_{14}$ |
| cyclophosphamide | 100 mg/m$^2$/day | oral | $D_1$–$D_{14}$ |
| doxorubicin | 30 mg/m$^2$ bolus | i.v. | $D_1$ and $D_8$ |
| 5-FU | 500 mg/m$^2$ bolus | i.v. | $D_1$ and $D_8$ | each cycle is repeated every 21 days until new progression of the disease is diagnosed.

in the CMF protocol:

| | Dose | Route | Days |
|---|---|---|---|
| 2-quinolone | 200–2000 mg/m$^2$/day or 5–50 mg/kg/day infusion for 1 h | i.v. | $D_1$–$D_5$ and $D_8$–$D_{12}$ |
| cyclophosphamide | 600 mg/m$^2$/day bolus | i.v. | $D_1$ and $D_8$ |
| methotrexate | 40 mg/m$^2$/day bolus | i.v. | $D_1$ and $D_8$ |
| 5-FU | 600 mg/m$^2$/day bolus | i.v. | $D_1$ and $D_8$ | this cycle is to be repeated every 3 to 5 weeks and the cure comprises 6 cycles.

In the CMF-VP protocol:

| | Dose | Route | Days |
|---|---|---|---|
| 2-quinolone | 200–2000 mg/m$^2$/day or 5–50 mg/kg/day infusion for 1 h | i.v. | $D_1$–$D_5$ $D_8$–$D_{12}$ $D_{15}$–$D_{19}$ $D_{22}$–$D_{26}$ |
| cyclo-phosphamide | 2 to 2.5 mg/kg/day | oral | daily |
| methotrexate | 25 to 50 mg/m$^2$/day | i.v. | $D_1$, $D_8$, $D_{15}$, $D_{22}$ |
| 5-FU | 300 to 500 mg/m$^2$/day | i.v. | $D_1$, $D_8$, $D_{15}$, $D_{22}$ |
| vincristine | 0.6 to 1.2 mg/m$^2$/day | i.v. | $D_1$, $D_8$, $D_{15}$, $D_{22}$ |
| prednisone | 30 mg/m$^2$/day | oral | from $D_1$ to $D_{10}$ | this cure is to be repeated every 4 weeks.

In the FEC protocol:

| | Dose | Route | Days |
|---|---|---|---|
| 2-quinolone | 200–2000 mg/m²/day or 5–50 mg/kg/day infusion for 1 h | i.v. | $D_1$–$D_5$ and $D_8$–$D_{12}$ |
| 5-FU | 600 mg/m²/day | i.v. | $D_1$ and $D_8$ |
| epirubicin | 50 mg/m² | i.v. | $D_1$ |
| cyclophosphamide | 600 mg/m² | i.v. | $D_1$ | this cure is to be repeated every 3 weeks.

in the MMC-VBC protocol (C. Brambilla et al., Tumori, 1989; 75: 141–144):

| | Dose | Route | Days |
|---|---|---|---|
| 2-quinolone | 200–2000 mg/m²/day or 5–50 mg/kg/day infusion for 1 h | i.v | $D_1$–$D_5$ and $D_{15}$–$D_{19}$ |
| mitomycin C | 10 mg/m² bolus | i.v. | $D_1$ |
| vinblastine | 50 mg/m²/day bolus | i.v. | $D_1$ and $D_{15}$ | this cure is to be repeated every 28 days until a progression of the disease is diagnosed.

in the NFL protocol (S. E. Jones et al., J. Clin. Oncol. 1991; 9: 1736–1739):

| | Dose | Route | Days |
|---|---|---|---|
| 2-quinolone | 200–2000 mg/m²/day or 5–50 mg/kg/day infusion for 1 h | i.v. | $D_1$–$D_5$ |
| mitoxantrone | 10 mg/m² bolus | i.v. | $D_1$ |
| 5-FU | 1000 mg/m² infusion for 24 hours | i.v | $D_1$–$D_3$ |
| leucovorin | 100 mg/m² bolus | i.v. | $D_1$ | the cure comprises two cycles with an interval of 21 days and then requires an evaluation.

The infusions of 2-quinolone can also be combined with the treatment of breast cancers with metastases when a taxoid is used, for example:

with paclitaxel (F. A. Holmes et al., J. Natl Cancer Inst. 1991; 83: 1797–1805) in the treatment of the forms with metastases which may be resistant to anthracyclins:

| | Dose | Route | Days |
|---|---|---|---|
| 2-quinolone | 200–2000 mg/m²/day or 5–50 mg/kg/day infusion for 1 h | i.v. | $D_1$–$D_5$ |
| paclitaxel | 175 mg/m² infusion for 3 to 24 hours | i.v. | $D_1$ | this cycle is repeated every 21 days until a new progression of the disease is diagnosed.

with docetaxel (C. A. Hudis et al., J. Clin. Oncol. 1996; 14: 58–65), in locally advanced or metastatic breast cancer, resistant or in relapse after cytotoxic chemotherapy (having comprised an anthracyclin) or in relapse during an auxiliary treatment:

| | Dose | Route | Days |
|---|---|---|---|
| 2-quinolone | 200–2000 mg/m²/day or 5–50 mg/kg/day infusion for 1 h | i.v. | $D_1$–$D_5$ |
| docetaxel | 100 mg/m² or 60–100 mg/m² infusion for 1 hour (or 24 hours) | i.v. | $D_1$ | this cycle is repeated every 21 days for a cure of two cycles or until a progression of the disease appears.

in dose intensification protocols, combining a transplantation of autologous medullary cells and of peripheral blood stem cells, in consolidation of the primary treatment, for example:

CPB protocol (W. P. Peters et al., J. Clin. Oncol. 1993; 11: 132–1143), in which the i.v. infusion of stem cells takes place on days $D_{-1}$, $D_0$ and $D_1$:

| | Dose | Route | Days |
|---|---|---|---|
| 2-quinolone | 200–2000 mg/m²/day or 5–50 mg/kg/day infusion for 1 h | i.v. | $D_{-6}$–$D_{-1}$ |
| cyclophosphamide | 1875 mg/m² infusion for 1 hour | i.v. | $D_{-6}$ to $D_{-4}$ |
| cisplatin | 55 mg/m²/day continuous infusion for 24 hours | i.v. | $D_{-6}$ to $D_{-4}$ |
| carmustin (BCNU) | 600 mg/m²/day infusion for 2 hours | i.v. | $D_{-3}$ |

CTCb protocol (K. Antman et al., J. Clin. Oncol. 1992; 10: 102–110), in which the i.v. infusion of stem cells takes place on $D_0$:

| | Dose | Route | Days |
|---|---|---|---|
| 2-quinolone | 200–2000 mg/m²/day or 5–50 mg/kg/day infusion for 1 h | i.v. | $D_{-7}$–$D_{-1}$ |
| cyclophosphamide | 1500 mg/m² continuous infusion for 24 hours (4 doses) | i.v. | $D_{-7}$ to $D_{-3}$ |
| thiotepa | 125 mg/m² continuous infusion for 24 hours (4 doses) | i.v. | $D_{-7}$ to $D_{-3}$ |
| carboplatin | 200 mg/m² continuous infusion for 24 hours (4 doses) | i.v. | $D_{-7}$ to $D_{-3}$ |

CTM protocol (L. E. Damon et al., J. Clin. Oncol. 1989; 7: 560–571 and I. C. Henderson et al., J. Cellular Biochem. 1994 (Suppl 18B): 95) in which the i.v. infusion of hematopoietic stem cells takes place on $D_0$

| | Dose | Route | Days |
|---|---|---|---|
| 2-quinolone | 200–2000 mg/m²/day or 5–50 mg/kg/day infusion for 1 h | i.v | $D_{-6}$–$D_{-1}$ |

-continued

| | Dose | Route | Days |
|---|---|---|---|
| cyclophosphamide | 1500 mg/m²/day infusion for 1 hour | i.v. | $D_{-6}$ to $D_{-3}$ |
| thiotepa | 150 mg/m²/day infusion for 2 hours | i.v. | $D_{-6}$ to $D_{-3}$ |
| mitoxantrone | 10–15 mg/m² infusion for 1 hour | i.v. | $D_{-6}$ to $D_{-3}$ |

3/ Gynecological Cancers 3.1 Ovarian Cancer for the treatment of ovarian carcinomas, in particular metastatic ones:
i) PAC protocol (G. A. Omura et al. J. Clin. Oncol. 1989; 7: 457–465): the infusions of 2-quinolones are administered according to the following scheme:

| | Dose | Route | Days |
|---|---|---|---|
| 2-quinolone | 200–2000 mg/m²/day or 5–50 mg/kg/day infusion for 1 h | i.v. | $D_1$–$D_5$ |
| cisplatin | 50 mg/m² (or 40–90 mg/m²) infusion for 1 to 2 hours | i.v. | $D_1$ |
| doxorubicin | 50 mg/m² bolus (or 30 to 50 mg/m²) | i.v. | $D_1$ |
| cyclophosphamide | 1000 mg/m² infusion for 1 to 2 hours (or 200 to 600 mg/m²) | i.v. | $D_1$ | this cycle is repeated every 21 to 28 days and the cure comprises 8 cycles.
ii) Altretamine protocol, according to A. Marietta et al. (Gynecol. Oncol. 1990; 36: 93–96):

| | Dose | Route | Days |
|---|---|---|---|
| 2-quinolone | 200–2000 mg/m²/day or 5–50 mg/kg/day infusion for 1 h | i.v. | $D_1$–$D_5$ $D_8$–$D_{12}$ |
| altretamine | 200 mg/m²/day divided into 4 doses | oral | $D_1$–$D_{15}$ | the cure comprising two cycles, with an interval of 28 days.
ii) Paclitaxel protocol: the 2-quinolones can be added to the paclitaxel protocol as described by W. P. McGuire et al. (Ann. Intern. Med. 1989; 111: 273–279):

| | Dose | Route | Days |
|---|---|---|---|
| 2-quinolone | 200–2000 mg/m²/day or 5–50 mg/kg/day infusion for 1 h | i.v. | $D_1$–$D_3$ |
| paclitaxel | 135 mg/m² infusion for 3 hours or 24 hours | i.v. | $D_1$ | the cure comprising two of these cycles, with an interval of 28 days (with evaluation at the end).

for the treatment of metastatic and refractory ovarian carcinomas, the 2-quinolones may be added to the secondary protocol, based on topotecan:

| | Dose | Route | Days |
|---|---|---|---|
| 2-quinolone | 200–2000 mg/m²/day or 5–50 mg/kg/day infusion for 1 h | i.v. | $D_1$–$D_5$ |
| topotecan | 1.5 mg/m²/day infusion for 0.5 hours | i.v. | $D_1$–$D_5$ | the cure comprising two cycles, with an interval of 21 days (with evaluation at the end) according to A. P. Kudelka et al. (J. Clin. Oncol. 1996; 14: 1552–1557).

3.2 Trophoblastic Tumors in patients at low risk, the 2-quinolones may be combined with the protocol described by H. Takamizawa et al. (Semin. Surg. Oncol. 1987; 3: 36–44):

| | Dose | Route | Days |
|---|---|---|---|
| 2-quinolone | 200–2000 mg/m²/day or 5–50 mg/kg/day infusion for 1 h | i.v | $D_1$–$D_5$ |
| methotrexate (MTX) | 20 mg/day | i.m. | $D_1$–$D_5$ |
| dactinomycin (DACT) | 0.5 mg/day as bolus | i.v. | $D_1$–$D_5$ |

(MTX-DATC protocol).

3.3 Uterine Cancers the 2-quinolones may also be combined with the CAV (or VAC) protocol according to the scheme below:

| | Dose | Route | Days |
|---|---|---|---|
| 2-quinolone | 200–2000 mg/m²/day or 5–50 mg/kg/day infusion for 1 h | i.v. | $D_1$–$D_3$ |
| cyclophosphamide | 750–1200 mg/m² infusion | i.v. | $D_1$ |
| doxorubicin | 45–50 mg/m² infusion | i.v. | $D_1$ |
| vincristine | 1.4 mg/m² | i.v. | $D_1$ | the cure comprising the repetition of this cycle every 21 days.
in the FAP protocol:

| | Dose | Route | Days |
|---|---|---|---|
| 2-quinolone | 200–2000 mg/m²/day or 5–50 mg/kg/day infusion for 1 h | i.v. | $D_1$–$D_5$ |
| fluorouracil (5-FU) | 600 mg/m²/day | i.v. | $D_1$, $D_8$ |
| doxorubicin | 30 mg/m² | i.v. | $D_1$ |
| cisplatin | 75 mg/m² | i.v. | $D_1$ | the cure comprising the repetition of this cycle every 21 or 28 days.

4/ Testicular Cancers

The 2-quinolones may also be combined with testicular cancer protocols:

BEP Protocol:

| | Dose | Route | Days |
|---|---|---|---|
| 2-quinolone | 200–2000 mg/m²/day or 5–50 mg/kg/day infusion for 1 h | i.v. | $D_1$–$D_5$ |
| bleomycin | 30 mg/m² infusion | i.v. | $D_1$ |
| etoposide | 100 mg/m²/day infusion | i.v. | $D_1$–$D_5$ |
| cisplatin | 20 mg/m²/day | i.v. | $D_1$–$D_5$ | the cure comprising 3 cycles, at a rate of 1 cycle every 21 days.

5/ Bladder Cancers

The 2-quinolones may be combined with the CISCA2 (also known as PAC) protocol:

| | Dose | Route | Days |
|---|---|---|---|
| 2-quinolone | 200–2000 mg/m²/day or 5–50 mg/kg/day infusion for 1 h | i.v. | $D_1$–$D_5$ |
| cisplatin | 50 mg/m² | i.v. | $D_1$ |
| cyclophosphamide | 600 mg/m² infusion | i.v. | $D_1$ |
| doxorubicin | 75 mg/m² infusion | i.v. | $D_1$ | the cycle being repeated every 3 weeks.

In the MVAC protocol (according to C. N. Sternberg et al., J. Urol. 1988; 139: 461–469):

| | Dose | Route | Days |
|---|---|---|---|
| 2-quinolone | 200–2000 mg/m²/day or 5–50 mg/kg/day infusion for 1 h | i.v. | $D_1$–$D_3$ $D_{15}$–$D_{18}$ $D_{22}$–$D_{25}$ |
| methotrexate | 30 mg/m² bolus | i.v. | $D_1$, $D_{15}$, $D_{22}$ |
| vinblastine | 3 mg/m² | i.v. | $D_2$ or $D_2$, $D_{15}$, $D_{22}$ |
| doxorubicin | 30 mg/m² bolus | i.v. | $D_2$ |
| cisplatin | 70–100 mg/m² infusion for 1 h | i.v. | $D_1$ or $D_2$ | this cycle being repeated every 4 to 5 weeks, for a minimum of 2 cycles.

6/ Nasopharyngeal Carcinomas/head and Neck Cancers

The 2-quinolones may be viably combined with polychemotherapy protocols used in the treatment of these cancers:

6.1 Nasopharyngeal Cancers

ABVD protocol:

| | Dose | Route | Days |
|---|---|---|---|
| 2-quinolone | 200–2000 mg/m²/day or 5–50 mg/kg/day infusion for 1 h | i.v. | $D_1$–$D_3$ $D_8$–$D_{10}$ or $D_{15}$–$D_{17}$ |
| doxorubicin | 30 mg/m²/day | i.v. | $D_1$ and $D_8$ or $D_{15}$ |
| bleomycin | 10 mg/m²/day | i.v. | $D_1$ and $D_8$ or $D_{15}$ |
| vinblastine | 6 mg/m²/day | i.v. | $D_1$ and $D_8$ or $D_{15}$ |
| dacarbazine | 200 mg/m²/day | i.v. | $D_1$ and $D_8$ or $D_{15}$ | the cure comprising 1 to 6 cycles repeated at a rate of 1 cycle every 4 weeks.

6.2 Head and Neck Cancers With Metastases in the Pt-FU protocol (e.g.: for pharyngeal cancers): according to the DVAL Study Group (New Engl. J. M. 1991; 324: 1685–1690):

| | Dose | Route | Days |
|---|---|---|---|
| 2-quinolone | 200–2000 mg/m²/day or 5–50 mg/kg/day infusion for 1 h | i.v. | $D_1$–$D_5$ |
| cisplatin | 100 mg/m² infusion for 1 hour | i.v. | $D_1$ |
| fluorouracil (5-FU) | 1000 mg/m²/day continuous infusion | i.v. | $D_1$–$D_5$ | the cure comprising two cycles, at a rate of 1 cycle every 3 weeks.

7/ Soft-tissue Sarcomas

The 2-quinolones may be introduced into a protocol such as the CYVADIC protocol:

according to H. M. Pinedo et al. (Cancer 1984; 53: 1825):

| | Dose | Route | Days |
|---|---|---|---|
| 2-quinolone | 200–2000 mg/m²/day or 5–50 mg/kg/day infusion for 1 h | i.v. | $D_1$–$D_5$ $D_8$–$D_{10}$ $D_{15}$–$D_{17}$ |
| cyclophosphamide (Cy) | 500 mg/m² bolus | i.v. | $D_2$ |
| vincristine (V) | 1.5 mg/m²/day bolus | i.v. | $D_1$, $D_8$, $D_{15}$ |
| doxorubicin (A) | 50 mg/m² bolus | i.v. | $D_2$ |
| dacarbazine (DIC) | 250 mg/m²/day infusion for 15 minutes | i.v. | $D_1$–$D_5$ | the cure comprising the repetition of this cycle every 4 weeks, first for 2 cycles.

8/ Hormono-refractory Prostate Cancer, With Metastases

In the VBL-estramustine protocol, according to G. R. Hudis et al. (J. Clin. Oncol. 1992; 10: 1754–1761):

| | Dose | Route | Days |
|---|---|---|---|
| 2-quinolone | 200–2000 mg/m²/day or 5–50 mg/kg/day infusion for 1 h | i.v. | $D_1$–$D_3$, $D_8$–$D_{10}$ $D_{15}$–$D_{17}$, $D_{22}$–$D_{24}$ $D_{29}$–$D_{31}$, $D_{36}$–$D_{38}$ |

-continued

| | Dose | Route | Days |
|---|---|---|---|
| vinblastine | 4 mg/m$^2$/day bolus | i.v. | $D_1$, $D_8$, $D_{15}$, $D_{22}$, $D_{29}$, $D_{36}$ |
| estramustine | 200 mg/m$^2$ tid (600 mg/m$^2$/day) | oral | every day for 6 weeks | a treatment cycle lasting 6 weeks and being followed by a 2-week free interval.

9/ Germinal Cell Cancers i) For tumors of favorable prognosis:
Pt-E protocol, according to G. J. Bosl et al. (J. Clin. Oncol. 1988; 6: 1231–1238)

| | Dose | Route | Days |
|---|---|---|---|
| 2-quinolone | 200–2000 mg/m$^2$/day or 5–50 mg/kg/day infusion for 1 h | i.v. | $D_1$–$D_5$ |
| cisplatin (Pt) | 20 mg/m$^2$/day infusion for 20 to 60 minutes | i.v. | $D_1$–$D_5$ |
| etoposide (E) | 100 mg/m$^2$/day infusion for 1 hour | i.v. | $D_1$–$D_5$ | the cure comprising 4 cycles, at a rate of 1 cycle 15 every 21 or 28 days.

ii) For tumors with metastases:
PEB protocol, according to S. D. Williams et al. (N. Eng. J. Med. 1987; 316: 1435–1440):

| | Dose | Route | Days |
|---|---|---|---|
| 2-quinolone | 200–2000 mg/m$^2$/day or 5–50 mg/kg/day infusion for 1 h | i.v. | $D_1$–$D_5$ $D_9$–$D_{11}$ $D_{16}$–$D_{18}$ |
| cisplatin (P) | 20 mg/m$^2$/day infusion for 20 to 60 minutes | i.v. | $D_1$–$D_5$ |
| etoposide (E) | 100 mg/m$^2$/day infusion for 1 hour | i.v. | $D_2$, $D_9$, $D_{16}$ |
| bleomycin (B) | 30U (or mg) day bolus | i.v. | $D_1$–$D_5$ | the cure comprising 4 cycles, at a rate of 1 cycle every 21 days.

10/ Kidney Cancers

Metastatic renal carcinoma: the 2-quinolones may be introduced into the protocol described by M. J. Wilkinson et al. (Cancer 1993; 71: 3601–3604):

| | Dose | Route | Days |
|---|---|---|---|
| 2-quinolone | 200–2000 mg/m$^2$/day or 5–50 mg/kg/day infusion for 1 h | i.v. | $D_1$–$D_5$ $D_8$–$D_{18}$ |
| floxuridine | 0.075 mg/kg/day continuous infusion | i.v. | $D_1$–$D_{14}$ | the cure comprising 2 cycles with an interval of 28 days.

Nephroblastoma: the 2-quinolones may be introduced into the DAVE protocol:

| | Dose | Route | Days |
|---|---|---|---|
| 2-quinolone | 200–2000 mg/m$^2$/day or 5–50 mg/kg/day infusion for 1 h | i.v. | $D_1$–$D_3$ $D_8$–$D_{10}$ |
| dactinomycin | 0.6 mg/m$^2$/day | i.v. | $D_1$, $D_8$ |
| doxorubicin | 30 mg/m$^2$/day | i.v. | $D_1$, $D_8$ |
| cyclophosphamide | 200 mg/m$^2$/day infusion for 1 hour | i.v. | $D_1$, $D_8$ | at a rate of one cycle every 3 to 4 weeks.

11/ Cancers of the Digestive Tract 11.1 Esophageal Cancers the 2-quinolones may be introduced into the FAP protocol according to:

| | Dose | Route | Days |
|---|---|---|---|
| 2-quinolone | 200–2000 mg/m$^2$/day or 5–50 mg/kg/day infusion for 1 h | i.v. | $D_1$–$D_3$ $D_8$–$D_{10}$ |
| 5-fluorouracil (5-FU) | 600 mg/m$^2$ | i.v. | $D_1$, $D_8$ |
| doxorubicin | 30 mg/m$^2$ | i.v. | $D_1$ |
| cisplatin | 75 mg/m$^2$ | i.v. | $D_1$ | this cycle being repeated every 3 to 4 weeks.

11.2 Stomach Cancers in gastric carcinomas that are advanced and/or with metastases:
EAP protocol (according to P. Preusser et al., J. Clin. Oncol. 1989; 7: 1310):

| | Dose | Route | Days |
|---|---|---|---|
| 2-quinolone | 200–2000 mg/m$^2$/day or 5–50 mg/kg/day infusion for 1 h | i.v. | $D_2$–$D_5$, $D_8$–$D_{10}$ |
| etoposide | 120 mg/m$^2$/day infusion for 1 hour | i.v. | $D_3$, $D_4$, $D_5$ or $D_4$–$D_6$ |
| doxorubicin | 20 mg/m$^2$/day bolus | i.v. | $D_1$, $D_7$ |
| cisplatin | 40 mg/m$^2$/day infusion for 1 hour | i.v. | $D_2$, $D_8$ | at a rate of 1 cycle every 28 days.

FAMtx protocol: according to J. A. Wils et al. (J. Clin. Oncol. 1991; 89: 827):

| | Dose | Route | Days |
|---|---|---|---|
| 2-quinolone | 200–2000 mg/m$^2$/day or 5–50 mg/kg/day infusion for 1 h | i.v. | $D_1$–$D_3$ |
| fluorouracil (5-FU) (F) | 1500 mg/m$^2$ bolus 1 hour after methotrexate | i.v. | $D_1$ |

-continued

| | Dose | Route | Days |
|---|---|---|---|
| doxorubicin (A) | 30 mg/m² bolus | i.v. | $D_{15}$ |
| methotrexate (Mtx) | 1500 mg/m² infusion for 30 minutes | i.v. | $D_1$ | the cure first comprising two cycles, with an interval of 28 days.

in certain patients, this protocol or its variant (epirubicin replacing doxorubicin) may be used according to the following scheme:

| | Dose | Route | Days |
|---|---|---|---|
| 2-quinolone | 200–2000 mg/m²/day or 5–50 mg/kg/day infusion for 1 h | i.v. | $D_1$–$D_3$ |
| fluorouracil (5-FU) | 1500 mg/m² | i.v. | $D_1$ |
| doxorubicin (A) or | 30 mg/m² bolus | i.v. | $D_1$ = FAMTx |
| epirubicin | 60 mg/m² bolus | i.v. | $D_1$ = FEMTx |
| methotrexate (to be infused before 5-FU) | 1500 mg/m² | i.v. | $D_1$ |
| leucovorine | 15 mg/m²/day | oral | $D_2$–$D_4$ |

12/ Colorectal Cancers the 2-quinolones may be introduced into the FU-Levamizole auxiliary treatment protocol for colorectal cancer (according to C. G. Moertel et al., N. Eng. J. Med. 1990; 322: 352):

| | Dose | Route | Days |
|---|---|---|---|
| 2-quinolone | 200–2000 mg/m²/day or 5–50 mg/kg/day infusion for 1 h | i.v. | $D_1$–$D_5$ $D_{29}$–$D_{31}$ |
| 5-fluorouracil | 450 mg/m²/day bolus | i.v. | $D_1$–$D_5$ |
| 5-fluorouracil | 450 mg/m² bolus | i.v. | $D_{29}$ |
| levamisole | 50 mg tid | oral | 3 days/week one week in two | the treatment in bolus with 5-FU being repeated every week after the induction phase $D_1$–$D_5$, for 52 weeks; the treatment with a 2-quinolone being repeated at the same rhythm, on the day of the bolus of 5-FU and then on the following 2 days.

for the treatment of colorectal cancer, which is resistant to treatment with 5-fluorouracil (5-FU) and with metastases:

according to M. L. Rothenberg et al. (J. Clin. Oncol. 1996; 14: 1128–1135):

| | Dose | Route | Days |
|---|---|---|---|
| 2-quinolone | 200–2000 mg/m²/day or 5–50 mg/kg/day infusion for 1 h | i.v. | $D_1$–$D_3$, $D_8$–$D_{10}$, $D_{15}$–$D_{17}$, $D_{22}$–$D_{24}$ |

-continued

| | Dose | Route | Days |
|---|---|---|---|
| irinotecan | 125 mg/m²/day | i.v. | $D_1$, $D_8$, $D_{15}$, $D_{22}$ | the cure comprising two cycles with an interval of 42 days.

13/ Kaposi's Sarcomas the 2-quinolones may be combined with the two protocols using antracyclines formulated as liposomes:

i) protocol described by P. S. Gill et al. (J. Clin. Oncol. 1995; 13: 996–1003) and C. A. Presant et al. (Lancet 1993; 341: 1242–1243):

| | Dose | Route | Days |
|---|---|---|---|
| 2-quinolone | 200–2000 mg/m²/day or 5–50 mg/kg/day infusion for 1 h | i.v. | $D_1$–$D_3$ and $D_{15}$–$D_{17}$ |
| liposomal daunorubicin | 20 mg/m²/day infusion for 1 h | i.v. | $D_1$, $D_{15}$ | the cure comprising two cycles repeated with an interval of 28 days before evaluating the effects.

ii) protocol of M. Harrison et al. (J. Clin. Oncol. 1995; 13: 914–920):

| | Dose | Route | Days |
|---|---|---|---|
| 2-quinolone | 200–2000 mg/m²/day or 5–50 mg/kg/day infusion for 1 h | i.v. | $D_1$–$D_3$ |
| liposomal doxorubicin | 20 mg/m² infusion for 30 minutes | i.v. | $D_1$ | the cure comprising two cycles repeated with an interval of 28 days before evaluating the effects.

14/ Metastatic Melanomas the 2-quinolones may also be incorporated into combination protocols for treating metastatic malignant melanomas:

DTIC/TAM protocol: according to G. Cocconi et al. (N. Eng. J. Med. 1992; 327: 516), the cure comprising the repetition of 4 cycles, at a rate of 1 cycle every 21 days, according to the scheme below:

| | Dose | Route | Days |
|---|---|---|---|
| 2-quinolone | 200–2000 mg/m²/day or 5–50 mg/kg/day infusion for 1 h | i.v. | $D_1$–$D_5$ |
| dacarbazine (DTIC) | 250 mg/m²/day infusion [15 to 30 min if central catheter] or [30 min if peripheral infusion in 250 ml] | i.v. | $D_1$–$D_5$ |
| tamoxifen (TAM) | 20 mg/m²/day | oral | $D_1$–$D_5$ | the cure comprising 4 cycles at a rate of 1 cycle every 21 days.

15/ Neuroendocrine Carcinoma

2-Quinolones may be combined with the protocol described by C. G Moertel et al. (Cancer 1991; 68: 227):

Pt-E protocol:

| | Dose | Route | Days |
|---|---|---|---|
| 2-quinolone | 200–2000 mg/m$^2$/day or 5–50 mg/kg/day infusion for 1 h | i.v. | $D_1$–$D_3$ |
| etoposide | 130 mg/m$^2$/day infusion for 1 hour | i.v. | $D_1$–$D_3$ |
| cisplatin | 45 mg/m$^2$/day infusion for 1 hour | i.v. | $D_2$, $D_3$ | the cure comprising two cycles repeated every 28 days.

16/ Pancreatic Cancer

Advanced pancreatic adenocarcinoma: the 2-quinolones may be combined with the treatment with gemcitabine, according to the protocol of M. Moore et al. (Proc. Am. Soc. Clin. Oncol. 1995; 14: 473):

| | Dose | Route | Days |
|---|---|---|---|
| 2-quinolone | 200–2000 mg/m$^2$/day or 5–50 mg/kg/day infusion for 1 h | i.v. | $D_1$–$D_3$, $D_8$–$D_{10}$, $D_{15}$, $D_{22}$, $D_{29}$, $D_{36}$, $D_{43}$, $D_{57}$ |
| gemcitabine | 1000 mg/m$^2$ infusion for 0.5 hour | i.v. | $D_1$, $D_8$, $D_{15}$, $D_{22}$, $D_{29}$, $D_{36}$, $D_{43}$, and then $D_{57}$ and then once/week for 3 weeks followed by 1 week of rest and evaluation |

B. Onco-hematology

1/ Acute Adult Leukemias

1.1. Acute Lymphoblastic Leukemia
1.1.1. Linker Protocol

The 2-quinolones may be added to the linker protocols-induction chemotherapy and consolidation chemotherapy (see C. A. Linker et al. Blood 1987; 69: 1242–1248 and C. A. Linker et al. Blood 1991; 78: 2814–2822) according to the following schemes:

i) Induction chemotherapy:

| | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$, $D_{15}$–$D_{19}$ |
| daunorubicin | 50 mg/m$^2$ bolus every 24 hours (30 mg/m$^2$ in the patients >50 years old) | i.v. | $D_1$, $D_2$, $D_3$ |
| vincristine | 2 mg bolus | i.v. | $D_1$, $D_8$, $D_{15}$, $D_{22}$ |
| prednisone | 60 mg/m$^2$/day | oral | $D_1$–$D_{28}$ |
| L-asparaginase | 6000 U/m$^2$ | i.m. | $D_{17}$–$D_{28}$ | ii) Consolidation chemotherapy (regimen A):

| | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$ |
| daunorubicin | 50 mg/m$^2$ bolus every 24 hours | i.v. | $D_1$, $D_2$ |
| vincristine | 2 mg bolus | i.v. | $D_1$, $D_9$ |
| prednisone | 60 mg/m$^2$/day divided into 3 doses | oral | $D_1$–$D_{14}$ |
| L-asparaginase | 12 000 U/m$^2$ | i.m. | $D_2$, $D_4$, $D_7$, $D_9$ and $D_{14}$ | the consolidation cure A comprises 4 consecutive cycles such as that described above=cycles 1, 3, 5 and 7.

iii) Consolidation chemotherapy (regimens B and C): the regimens described below correspond to the consolidation cycles 2, 4, 6 and 8 (regimen B) and 9 (regimen C), described by C. A. Linker et al.:

| Regimen B: | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$ |
| Ara-C | 300 mg/m$^2$ infusion for 2 hours | i.v. | $D_1$, $D_4$, $D_8$, $D_{11}$ |
| teniposide | 165 mg/m$^2$ infusion for 2 hours (4 cycles) | i.v. | $D_1$, $D_4$, $D_8$, $D_{11}$ |

| Regimen C: | Dose | Route | Days |
|---|---|---|---|
| 2-quinolone | 200–2000 mg/m$^2$/day or 5–50 mg/kg/day infusion for 1 h | i.v. | $D_1$–$D_5$, |
| methotrexate | 690 mg/m$^2$ continuous infusion for 42 hours | i.v. | $D_1$–$D_2$ |
| leucovorin | 15 mg/m$^2$ every 6 hours | oral | $D_2$–$D_5$ |

1.1.2. Hoelzer Protocol

The products claimed may be added to the cytotoxic agents of this polychemotherapy protocol (D. Hoelzer et al., Blood 1984; 64: 38–47, D. Hoelzer et al., Blood 1988; 71: 123–131) according to the following scheme:

i) Induction chemotherapy/Phase 1:

| | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$, $D_{15}$–$D_{19}$ |
| daunorubicin | 25 mg/m$^2$ | i.v. | $D_1$, $D_8$, $D_{15}$, $D_{22}$ |
| vincristine | 1.5 mg/m$^2$ (maximum 2 mg) | i.v. | $D_1$, $D_8$, $D_{15}$, $D_{22}$ |
| prednisone | 60 mg/m$^2$ | oral | $D_1$–$D_{28}$ |
| L-asparaginase | 5000 U/m$^2$ (maximum 2 mg) | i.m. | $D_1$–$D_{14}$ | ii) Induction chemotherapy/Phase 2:
Phase 2 of the induction may be carried out as follows:

|  | Dose | Route | Days |
|---|---|---|---|
| 2-quinolone | 200–2000 mg/m$^2$/day or 5–50 mg/kg/day infusion for 1 h | i.v. | $D_{29}$–$D_{33}$, $D_{36}$–$D_{40}$, $D_{43}$–$D_{47}$ |
| cyclophosphamide | 650 mg/m$^2$ (maximum 1000 mg) | i.v. | $D_{29}$, $D_{43}$, $D_{87}$ |
| cytarabine | 75 mg/m$^2$/day infusion for 1 hour | i.v. | $D_{31}$–$D_{34}$, $D_{38}$–$D_{41}$, $D_{45}$–$D_{48}$, $D_{52}$–$D_{55}$ |
| mercaptopurine | 60 mg/m$^2$ | oral | $D_{29}$–$D_{57}$ |
| methotrexate | 10 mg/m$^2$/day (maximum 15 mg) | i.v. | $D_{31}$, $D_{38}$, $D_{45}$, $D_{52}$ | iii) Re-induction chemotherapy/Phase 1:

|  | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$, $D_{15}$–$D_{19}$, $D_{22}$–$D_{26}$ |
| doxorubicin | 25 mg/m$^2$/day | i.v. | $D_1$, $D_8$, $D_{15}$, $D_{22}$ |
| dexamethasone | 10 mg/m$^2$/day | i.v. | $D_1$–$D_{28}$ |
| vincristine | 1.5 mg/m$^2$/day (maximum 2 mg) | oral | $D_1$, $D_8$, $D_{15}$ and $D_{22}$ | iv) Re-induction chemotherapy/Phase 2:

|  | Dose | Route | Days |
|---|---|---|---|
| 2-quinolone | 200–2000 mg/m$^2$/day or 5–50 mg/kg/day infusion for 1 h | i.v. | $D_{31}$–$D_{35}$, $D_{38}$–$D_{42}$ |
| cyclophosphamide | 650 mg/m$^2$ (maximum: 1000 mg) | i.v. | $D_{29}$ |
| cytarabine | 75 mg/m$^2$ | i.v. | $D_{31}$–$D_{34}$, $D_{38}$–$D_{41}$ |
| thioguanine | 60 mg/m$^2$ | oral | $D_{29}$–$D_{42}$ |

1.2. Acute Myeloid Leukemias
1.2.1. Treatment of Adults of Any Age

The 2-quinolones may be added, according to the scheme below, to the treatment incorporating the standard dose of cytarabine described previously by R. O. Dilleman et al. (Blood, 1991; 78: 2520–2526), Z. A. Arlin et al. (Leukemia 1990; 4: 177–183) and P. H. Wiernik et al. (Blood 1992; 79: 313–319):

|  | Dose | Route | Days |
|---|---|---|---|
| 2-quinolone | 200–2000 mg/m$^2$/day or 5–50 mg/kg/day infusion for 1 h | i.v. | $D_1$–$D_{12}$ |
| cytarabine | 100–200 mg/m$^2$/day in continuous infusion | i.v. | $D_1$–$D_7$ |
| daunorubicin | 45 mg/m$^2$/day in bolus (30 mg/m$^2$/day if ≥60 years old) | i.v. | $D_1$–$D_3$ or $D_8$–$D_{10}$ |
| or mitoxantrone | 12 mg/m$^2$ as daily bolus | i.v. | $D_1$–$D_3$ |
| or idarubicin | 13 mg/m$^2$ as daily bolus | i.v. | $D_1$–$D_3$ |

1.2.2. Treatment of Adults Less Than 60 Years Old
i) Induction chemotherapy:
This induction cycle incorporates the administration of cytarabine at high dose according to the following scheme:

|  | Dose | Route | Days |
|---|---|---|---|
| 2-quinolone | 200–2000 mg/m$^2$/day or 5–50 mg/kg/day infusion for 1 h | i.v. | $D_1$–$D_{10}$ |
| Ara-C (cytarabine) | 2000 mg/m$^2$/day infusion for 2 hours, every 12 hours | i.v. | $D_1$–$D_6$ |
| daunorubicin | 60 mg/m$^2$/day in continuous infusion for 24 hours | i.v. | $D_4$–$D_6$ |
| or cytarabine | 3000 mg/m$^2$/day infusion for 1 hour, every 12 hours | i.v. | $D_1$–$D_6$ |
| daunorubicin | 45 mg/m$^2$ bolus every 24 hours | i.v. | $D_7$–$D_9$ |

(in order to reduce the risk of C.N.S. toxicity, in the event of renal insufficiency, adjust the dosage of cytarabine to the creatinine clearance) according to L. E. Damon et al. (Leukemia 1994; 8: 535–541), G. L. Phillips et al. (Blood 1991; 77: 1429–1435) and G. Smith et al. (J. Clin. Oncol. 1997; 15: 833–839).

ii) Consolidation Chemotherapy:
The cycle described below will be repeated 8 times, at a rate of 1 cycle every 4 to 6 weeks (according to R. J. Mayer et al., N. Engl J. Med. 1994; 331: 896–903):

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| cytarabine | 3000 mg/m$^2$ infusion for 3 hours, every 12 hours (4 cycles) | i.v. | $D_1$, $D_3$, $D_5$ |
| and then cytarabine | 100 mg/m$^2$/day every 12 hours | s.c. | $D_1$–$D_5$ |
| daunorubicin | 45 mg/m$^2$ bolus (4 cycles) | i.v. | $D_1$ | iii) Consolidation chemotherapy (with strong dose of cytarabine):
The cycle described below will have to be repeated twice and is suitable according to G. L. Phillips et al. (Blood 1991; 77: 1429–1435); S. N. Wolff et al. (J. Clin. Oncol. 1989; 7: 1260–1267); R. J. Mayer et al. (N. Engl J. Med. 1994; 331: 896–903):

|  | Dose | Route | Days |
|---|---|---|---|
| 2-quinolone | 200–2000 mg/m$^2$/day or 5–50 mg/kg/day infusion for 1 h | i.v. | $D_1$–$D_{10}$ |
| cytarabine | 3000 mg/m$^2$ 1 hour every 12 hours | i.v. | $D_1$–$D_6$ |
| daunorubicin | 30–45 mg/m$^2$/day bolus once/day | i.v. | $D_7$–$D_9$ |

1.2.3. Treatment of Adults 60 Years Old or More

The substances claimed may be added to the consolidation chemotherapy protocols below:

i) according to R. O. Dilman et al. (Blood 1991; 78; 2520–2526), Z. A. Arlin et al. (Leukemia 1990; 4: 177–183), P. H. Wiernik et al. (1992; 79: 313–319):

|  | Dose | Route | Days |
|---|---|---|---|
| 2-quinolone | 200–2000 mg/m$^2$/day or 5–50 mg/kg/day infusion for 1 h | i.v. | $D_1$–$D_6$ |
| cytarabine (Ara-C) | 100–200 mg/m$^2$ continuous infusion for 24 hours | i.v. | $D_1$–$D_5$ |
| daunorubicin or | 30–45 mg/m$^2$/day bolus | i.v. | $D_1$, $D_2$ |
| mitoxantrone or | 12 mg/m$^2$/day bolus | i.v. | $D_1$, $D_2$ |
| idarubicin | 13 mg/m$^2$/day bolus | i.v. | $D_1$, $D_2$ | ii) According to R. J. Mayer et al. (N. Engl. J. Med. 194; 331: 896–903):

|  | Dose | Route | Days |
|---|---|---|---|
| 2-quinolone | 200–2000 mg/m$^2$/day or 5–50 mg/kg/day infusion for 1 h | i.v. | $D_1$–$D_6$ |
| cytarabine | 100 mg/m$^2$ continuous infusion for 24 hours (4 cycles) | i.v. | $D_1$–$D_2$ |
| and then cytarabine | 100 mg/m$^2$ every 12 hours | s.c. | $D_1$, $D_5$ |
| daunorubicin | 45 mg/m$^2$/day bolus (4 cycles) | i.v. | $J_1$ | iii) According to C. A. Linker et al. (Blood 1993; 81: 311–318), N. Chao et al. (Blood 1993; 81: 319–323) and A. M. Yeager et al. (N. Eng. J. Med. 1986; 315: 145–147):

This protocol comprises an autologous bone marrow transplantation (performed on day $D_0$):

|  | Dose | Route | Days |
|---|---|---|---|
| 2-quinolone | 200–2000 mg/m$^2$/day or 5–50 mg/kg/day infusion for 1 h | i.v. | $D_{-7}$–$D_{-2}$ |
| busulfan | 1 mg/kg qid (16 doses in total) | oral | $D_{-7}$ to $D_{-4}$ |
| etoposide or | 60 mg/kg/day infusion for 10 hours | i.v. | $D_{-3}$ |
| 2-quinolone | 200–2000 mg/m$^2$/day or 5–50 mg/kg/day infusion for 1 h | i.v. | $D_{-9}$–$D_{-1}$ |
| busulfan | 1 mg/kg qid | oral | $D_{-9}$ to $D_{-6}$ |
| cyclophosphamide | 50 mg/kg/day infusion for 1 hour | i.v. | $D_{-5}$ to $D_{-2}$ | iv) In the case of HLA-compatible allogenic bone marrow transplantation, according to: P. J. Tutscha et at. Blood 1987; 70: 1382–1388, F. R. Applebaum et al., Ann. Int. Med. 1984; 101: 581–588:

|  | Dose | Route | Days |
|---|---|---|---|
| 2-quinolone | 200–2000 mg/m$^2$/day or 5–50 mg/kg/day infusion for 1 h | i.v. | $D_{-7}$–$D_{-1}$ |
| busulfan | 1 mg/kg qid (16 doses in total) | oral | $D_{-7}$ to $D_{-4}$ |
| cyclophosphamide | 60 mg/kg/day infusion for 1 hour | i.v. | $D_{-3}$ to $D_{-2}$ |

2/ Chronic Adult Leukemias

2.1 Chronic Myeloid Leukemia

In the myeloblast phase, the 2-quinolones may be added to the HU-Mith treatment described by C. A. Koller et al. (N. Engl. J. Med. 1986; 315: 1433–1438):

|  | Dose | Route | Days |
|---|---|---|---|
| 2-quinolone | 200–2000 mg/m$^2$/day or 5–50 mg/kg/day infusion for 1 h | i.v. | $D_1$–$D_6$ $D_8$–$D_{12}$ $D_{15}$–$D_{19}$ $D_{22}$–$D_{26}$ |
| hydroxyurea | 500 mg/day | oral | every day |
| mithramycin | 25 µg/kg/day infusion for 2–4 hours | i.v. | daily for 3 weeks and then 3 times/week |

2.2. Chronic Lymphocytic Leukemia

2.2.1 FCG-CLL Protocol

The 2-quinolones may be added to the "pulsed chlorambucil" combinations as described by E. Kimby et al. (Leuk. Lymphoma 1991; 5 (Suppl.) 93–96) and by FCGCLL (Blood 1990; 75: 1422–1425):

|  | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$, $D_{15}$–$D_{22}$ |
| chlorambucil or | 0.1 mg/kg/day | oral | once/day |
| chlorambucil and | 0.4 mg/kg/day every 14 days | oral | $D_1$ |
| prednisone | 75 mg/day | oral | $D_1$–$D_3$ |

2.2.2 Fludarabine-CdA Protocol

According to H. G. Chun et al. (J. Clin. Oncol. 1991; 9: 175–188), M. J. Keating et al. (Blood 1989; 74: 19–25/J. Clin. Oncol. 1991; 9: 44–49) and A. Saven et al. (J. Clin. Oncol. 1995; 13: 570–574):

|  | Dose | Route | Days |
|---|---|---|---|
| 2-quinolone | 200–2000 mg/m$^2$/day or 5–50 mg/kg/day infusion for 1 h | i.v. | $D_1$–$D_8$ (once/month for 6 to 12 cycles) |

-continued

| | Dose | Route | Days |
|---|---|---|---|
| fludarabine | 25–30 mg/m²/day infusion for 30 minutes [every 4 weeks for 6 to 12 cycles] | i.v. | $D_1$–$D_5$ |
| or | | | |
| cladibrine | 0.09 mg/kg/day in continuous infusion [1 cycle every 28 to 35 days for 1 to 9 cycles (median: 4 cycles)] | i.v. | $D_1$–$D_7$ |

3/ Lymphoproliferative Diseases

3.1 Hodgkin's Disease

The 2-quinolones may be incorporated into the polychemotherapy protocols used conventionally for treating Hodgkin lymphoma:

3.1.1 AVDB Protocol

According to G. Bonnadonna et al. (Cancer Clin. Trials 1979; 2: 217–226) and G. P. Canellos et al. (N. Engl. J. Med. 1993; 327: 1478–1484):

| | Dose | Route | Days |
|---|---|---|---|
| 2-quinolone | 200–2000 mg/m²/day or 5–50 mg/kg/day infusion for 1 h | i.v. | $D_1$–$D_3$, $D_{15}$–$D_{18}$ |
| doxorubicin (A) | 25 mg/m² bolus | i.v. | $D_1$, $D_{15}$ |
| bleomycin (B) | 10 U/m² bolus | i.v. | $D_1$, $D_{15}$ |
| vinblastine (V) | 6 mg/m² bolus | i.v. | $D_1$, $D_{15}$ |
| dacarbazine (D) | 375 mg/m² bolus | i.v. | $D_1$, $D_{15}$ | the cure comprising 6 to 8 cycles, at a rate of 1 cycle every 28 days.

3.1.2 MOPP/ABVD Protocol

According to G. Bonnadonna et al. (Ann. Intern. Med. 1986; 104: 739–746) and G. P. Canellos et al. (N. Engl. J. Med. 1993; 327: 1478–1484):

the MOPP protocol should be alternated with the ABVD protocol (cf. § 3.1.1) every 28 days, and the cure comprises 6 cycles:

| MOPP protocol: | Dose | Route | Days |
|---|---|---|---|
| 2-quinolone | 200–2000 mg/m²/day or 5–50 mg/kg/day infusion for 1 h | i.v. | $D_1$–$D_3$, $D_8$–$D_{11}$ and $D_{14}$–$D_{17}$ |
| mechlorethamine (M) | 6 mg/m² bolus | i.v. | $D_1$, $D_8$ |
| vincristine (O) | 1.4 mg/m² bolus (no maximum) | i.v. | $D_1$, $D_8$ |
| procarbazine (P) | 100 mg/m²/day | oral | $D_1$–$D_{14}$ |
| prednisone (P) | 40 mg/m²/day | oral | $D_1$–$D_{14}$ |

3.1.3 Stanford V Protocol

According to N. L. Bartlett et al. (J. Clin. Oncol. 1995; 13: 1080–1088):

| MOPP protocol: | Dose | Route | Days |
|---|---|---|---|
| 2-quinolone | 200–2000 mg/m²/day or 5–50 mg/kg/day infusion for 1 h | i.v. | $D_1$–$D_5$, $D_8$–$D_{12}$, $D_{15}$–$D_{19}$, $D_{22}$–$D_{26}$ |
| doxorubicin | 25 mg/m² | i.v | $D_1$, $D_{15}$ |
| vinblastine | 6 mg/m² bolus (4 mg/m² during cycle 3 if $\geq$50 years old) | i.v. | $D_1$, $D_{15}$ |
| mechlorethamine (M) | 6 mg/m² bolus | i.v. | $D_1$ |
| vincristine | 1.4 mg/m² bolus (max. dose: 2 mg) [1 mg/m² during cycle 3 if $\geq$50 years old] | i.v. | $D_1$, $D_{22}$ |
| bleomycin | 5 U/m² | i.v. | $D_8$, $D_{22}$ |
| etoposide | 60 mg/m² | oral | $D_{15}$, $D_{16}$ |
| prednisone | 40 mg/m²/day | oral | once/week (weeks 1–9) | the cure comprising 3 cycles at a rate of 1 cycle every 28 days.

3.1.4 EVA Protocol

According to G. P. Canellos et al. (Proc. Am. Soc. Clin. Oncol. 1991; 10: 273):

| | Dose | Route | Days |
|---|---|---|---|
| 2-quinolone | 200–2000 mg/m²/day or 5–50 mg/kg/day infusion for 1 h | i.v. | $D_1$–$D_5$ |
| etoposide (E) | 100 mg/m² infusion for 2 hours | oral | $D_1$, $D_2$, $D_3$ |
| vinblastine (V) | 6 mg/m² bolus | i.v. | $D_1$ |
| doxorubicin (A) | 50 mg/m² bolus | i.v. | $D_1$ | the cure comprising 6 cycles at a rate of 1 cycle every 28 days.

3.1.5 B-CAVe Protocol

According to W. G. Harker et al. (Ann. Intern. Med. 1984; 101: 440–446):

| | Dose | Route | Days |
|---|---|---|---|
| 2-quinolone | 200–2000 mg/m²/day or 5–50 mg/kg/day infusion for 1 h | i.v. | $D_1$–$D_3$ |
| bleomycin (B) | 5 U/m² bolus | i.v. | $D_1$ |
| lomustine (CCNU) | 100 mg/m² | oral | $D_1$ |
| doxorubicin (A) | 60 mg/m² bolus | i.v. | $D_1$ |
| vinblastine (Ve) | 5 mg/m² bolus | i.v. | $D_1$ | the cure comprising 8 cycles, at a rate of 1 cycle every 28 days.

3.2. Non-Hodgkin Lymphomas

3.2.1. With a Low Degree of Malignance i)—CVP protocol

According to C. M. Bagley et al. (Ann. Intern. Med. 1972; 76: 227–234) and C. S. Portlock et al. (Blood 1976; 47: 747–756)

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| cyclophosphamide (c) | 300–400 mg/m$^2$/day | oral | $D_1$, $D_5$ |
| vincristine (V) | 1.4 mg/m$^2$ bolus (max. 2 mg) | i.v. | $D_1$ |
| prednisone (P) | 100 mg/m$^2$/day | oral | $D_1$, $D_5$ | this cycle is repeated every 21 days up to the maximum response.

ii)—I-COPA protocol

According to R. V. Smalley et al. (N. Eng. J. Med. 1992; 327: 1336–1341)

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| cyclophosphamide (C) | 600 mg/m$^2$ day | i.v. | $D_1$ |
| vincristine (O) | 1.2 mg/m$^2$ bolus (max. 2 mg) | i.v. | $D_1$ |
| prednisone (P) | 100 mg/m$^2$/day | i.v. | $D_1$–$D_5$ |
| doxorubicin (A) | 50 mg/m$^2$ bolus | i.v. | $D_1$ |
| interferon-alpha (I) | 6 MU/m$^2$ | i.m. | $D_{22}$–$D_{26}$ | the cure comprises 8 to 10 cycles, at a rate of 1 cycle every 28 days.

iii)—Fludarabine-CdA protocol

According to P. Solol-Celigny et al. (Blood 1994; 84 (Supp. 1): 383a), H. Hoeschster et al.; (Blood 1994; 84 (Suppl. 1): 564a and A. C. Kay (J. Clin. Oncol. 1992; 10: 371–377)

|  | Dose | Route | Days |
|---|---|---|---|
| 2-quinolone | 200–2000 mg/m$^2$/day or 5–50 mg/kg/day infusion for 1 h | i.v. | $D_1$–$D_7$ |
| fludarabine | 25 mg/m$^2$ day infusion for 0.5 hour | i.v. | $D_1$–$D_5$ |
| or fludarabine and cyclophosphamide | 20 mg/m$^2$/day 600–1000 mg/m$^2$/day | i.v. i.v. | $D_1$–$D_5$ $D_1$ |
| or cladribine | 0.1 mg/m$^2$/day infusion for 24 hours | i.v. | $D_1$–$D_7$ | for fludarine, each cycle is repeated every 28 days; For cladribine, each cycle is repeated every 35 days.

3.2.2. With an Intermediate Degree of Malignance i)—CHOP or CNOP protocol

According to E M McKelvey et al. (Cancer 1976; 38: 1484–1493), J. O. Armitage et al. (J. Clin. Oncol. 1984; 2: 898–902), S. Paulovsky et al. (Ann. Oncol. 1992; 3: 205–209)

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| cyclophosphamide (C) | 750 mg/m$^2$ day | i.v. | $D_1$ |
| doxorubicin (H) | 50 mg/m$^2$ bolus | i.v. | $D_1$ |
| vincristine (O) | 1.4 mg/m$^2$ bolus (max: 2 mg) | i.v. | $D_1$ |
| prednisone (P) | 100 mg/m$^2$/day (as 1 dose/day) | oral | $D_1$–$D_5$ | for the CHOP protocol

Mitoxantrone (N) may be used to replace (CNOP protocol) doxorubicin in patients over 60 years old (dose: 12 mg/m$^2$ as i.v. bolus on day D1 of each cycle).

The cure with the CHOP or CNOP protocol comprises 6 to 8 cycles at a rate of 1 cycle every 21 days.

ii)—MACOP-B protocol

According to P. Klimo et al. (Ann. Intern. Med. 1985; 102: 596–602) and I. A. Cooper et al. (J. Clin. Oncol. 1994; 12: 769–778)

|  | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$ $D_{15}$–$D_{22}$, $D_{29}$–$D_{33}$ $D_{43}$–$D_{47}$, $D_{57}$–$D_{61}$, $D_{71}$–$D_{75}$ |
| methotrexate (M) | 100 mg/m$^2$ bolus then 300 mg/m$^2$ infusion for 4 hours | i.v. | $D_8$, $D_{36}$, $D_{64}$ |
| leucovorin | 15 mg qid | oral | $D_9$, $D_{37}$, $D_{65}$ |
| doxorubicin (A) | 50 mg/m$^2$ bolus | i.v. | $D_1$, $D_{15}$, $D_{29}$, $D_{43}$, $D_{57}$, $D_{71}$ |
| cyclophosphamide (c) | 350 mg/m$^2$ bolus | i.v. | $D_1$, $D_5$, $D_{29}$, $D_{43}$, $D_{57}$, $D_{71}$ |
| vincristine (O) | 1.4 mg/m$^2$ bolus (max: 2 mg) | i.v. | $D_8$, $D_{22}$, $D_{36}$, $D_{50}$, $D_{64}$, $D_{78}$ |
| prednisone (P) | 75 mg/day | oral | every day for 12 weeks |
| bleomycin (B) | 10 U/m$^2$ bolus | i.v. | $D_{22}$, $D_{50}$, $D_{78}$ | this treatment protocol spreads over 12 weeks and corresponds to 1 cycle.

iii)—VACOP-B protocol

According to J. M. Connors et al. (Proc. Am. Soc. Clin. Oncol. 1990; 9: 254):

|  | Dose | Route | Days |
|---|---|---|---|
| 2-quinolone | 200–2000 mg/m$^2$/day or 5–50 mg/kg/day infusion for 1 h | i.v. | $D_1$–$D_5$, $D_8$–$D_{12}$ $D_{15}$–$D_{22}$, $D_{29}$–$D_{34}$D $D_{43}$–$D_{47}$, $D_{57}$–$D_{61}$, $D_{71}$–$D_{75}$ |

| | Dose | Route | Days |
|---|---|---|---|
| etoposide (V) | 50 mg/m² | i.v. | $D_{13}$, $D_{43}$, $D_{71}$ |
| etoposide | 100 mg/m² | oral | $D_{16}$, $D_{17}$, $D_{44}$, $D_{45}$, $D_{72}$, $D_{73}$ |
| doxorubicin (A) | 50 mg/m² bolus | i.v. | $D_1$, $D_{15}$, $D_{29}$, $D_{43}$, $D_{57}$, $D_{71}$ |
| cyclophosphamide (c) | 350 mg/m²/day bolus | i.v. | $D_8$, $D_{22}$, $D_{36}$, $D_{50}$, $D_{64}$, $D_{78}$ |
| vincristine (O) | 1.2 mg/m² bolus | i.v. | $D_8$, $D_{22}$, $D_{36}$, $D_{50}$, $D_{64}$, $D_{78}$ |
| prednisone (P) | 45 mg/m²/day | oral | 1/day for 1 week, then 4/day for the next 11 weeks | each cycle lasting 12 weeks.

iv)—m-BACOD/M-BACOD protocol

According to M. A. Shipp et al. (Ann. Int. Med. 1986; 140; 757–765) and A. T. Skarin et al. (J. Clin. Oncol. 1983; 1: 91–98)

| | Dose | Route | Days |
|---|---|---|---|
| 2-quinolone | 200–2000 mg/m²/day or 5–50 mg/kg/day infusion for 1 h | i.v. | $D_1$–$D_5$, $D_6$–$D_{12}$ $D_{15}$–$D_{19}$ |
| methotrexate | | | |
| (m) | 200 mg/m² infusion for 4 hours | i.v. | $D_8$, $D_{15}$ |
| or | | | or |
| (M) | 3000 mg/m² infusion for 4 hours | i.v. | $D_{15}$ |
| leucovorin | 10 mg/m² qid (6 doses in total) | oral | $D_9$, $D_{16}$ or $D_{16}$ |
| bleomycin (B) | 4 U/m² bolus | i.v. | $D_1$ |
| doxorubicin (A) | 45 mg/m² bolus | i.v. | $D_1$ |
| cyclophosphamide (C) | 600 mg/m² bolus | i.v. | $D_1$ |
| vincristine (O) | 1 mg/m² bolus | i.v. | $D_1$ |
| dexamethasone (D) | 6 mg/m²/day | oral | $D_1$–$D_5$ | the cure comprising 10 cycles, at a rate of 1 cycle every 21 days.

v)—ProMACE/CytaBOM protocol

According to D. L. Longo et al. (J. Clin. Oncol. 1991; 9: 25–38):

| | Dose | Route | Days |
|---|---|---|---|
| 2-quinolone | 200–2000 mg/m²/day or 5–50 mg/kg/day infusion for 1 h | i.v. | $D_1$–$D_5$, $D_6$–$D_{12}$ |
| cyclophosphamide (C) | 650 mg/m² infusion for 0.5 hour | i.v. | $D_1$ |
| doxorubicin (A) | 25 mg/m² bolus | i.v. | $D_1$ |
| etoposide | 120 mg/m² infusion for 1 hour | i.v. | $D_1$ |
| prednisone (P) | 60 mg/day | oral | $D_1$–$D_{14}$ |
| cytarabine | 300 mg/m² bolus | i.v. | $D_8$ |
| bleomycin (B) | 5 U/m² bolus | i.v. | $D_8$ |
| vincristine (O) | 1.4 mg/m² bolus | i.v. | $D_8$ |
| methotrexate | 120 mg/m² bolus | i.v. | $D_8$ |
| leucovorin | 25 mg/m² qid (4 doses in total) | oral | $D_9$ | the cure comprising 6 to 8 cycles, at a rate of 1 cycle every 14 days.

3.2.3. With a Low or Intermediate Degree of Malignance i)—ESHAP rescue protocol

In the event of a relapse or of a failure of the first line treatment, according to W. S. Velasquez et al. (J. Clin. Oncol. 1994; 12: 1169–1176)

| | Dose | Route | Days |
|---|---|---|---|
| 2-quinolone | 200–2000 mg/m²/day or 5–50 mg/kg/day infusion for 1 h | i.v. | $D_1$–$D_5$ |
| etoposide (E) | 40 mg/m² infusion for 2 hours | i.v. | $D_1$–$D_4$ |
| methylprednisolone (S) | 500 mg/day infusion for 15 minutes | i.v. | $D_1$, $D_4$ |
| cytarabine (HA) | 2000 mg/m² infusion for 3 hours | i.v. | $D_5$ |
| cisplatin (P) | 25 mg/m²/day bolus continuous infusion for 24 hours | i.v. | $D_1$–$D_4$ | the cure comprising 6 cycles, at a rate of 1 cycle every 28 days.

ii)—MINE rescue protocol

In the event of a relapse or of a failure of the first line treatment, according to F. Cabanillas et al. (Semin. Oncol. 1990; 17 (suppl. 10): 28–33)

| | Dose | Route | Days |
|---|---|---|---|
| 2-quinolone | 200–2000 mg/m²/day or 5–50 mg/kg/day infusion for 1 h | i.v. | $D_1$–$D_5$ |
| ifosfamide (I) | 1330 mg/m² infusion for 1 hour | i.v. | $D_1$–$D_3$ |
| mesna (M) | 1330 mg/m² in the infusion of ifosfamide and then 266 mg/m² bolus 4 and 8 hours after each dose of ifosfamide | i.v. | $D_1$–$D_3$ |
| mitoxantrone (M) | 8 mg/m² infusion for 15 minutes | i.v. | $D_1$ |
| etoposide (E) | 65 mg/m²/day infusion for 1 hour | i.v. | $D_1$–$D_3$ | this cycle being repeated every 21 days.

3.3. Non-Hodgkin Lymphomas: Burkitt's Lymphoma, Small-cell Lymphoma, Lymphoblast Lymphoma 3.3.1. Magrath Protocol the products claimed may be combined with the Magrath protocols according to the following schemes:

i)—cycle 1 according to I. T. Magrath et al. (Blood 1984; 63: 1102–1111)

| | Dose | Route | Days |
|---|---|---|---|
| 2-quinolone | 200–2000 mg/m²/day or 5–50 mg/kg/day infusion for 1 h | i.v. | $D_1$–$D_5$, $D_8$–$D_{12}$ |

|  | Dose | Route | Days |
| --- | --- | --- | --- |
| cytarabine | 30 mg/m | intrathecal | $D_1, D_2, D_3, D_7$ |
| cyclophosphamide | 1200 mg/m² bolus | i.v. | $D_1$ |
| methotrexate | 12.5 mg/m² (max: 12.5 mg) | intrathecal | $D_{10}$ |
| methotrexate | 300 mg/m²/day infusion for 1 hour and then 60 mg/m²/h infusion for 41 hours | i.v. | $D_{10}$–$D_{11}$ |
| leucovorin | 15 mg/m² bolus qid (8 successive doses) | i.v. | to be started 42 hours after the start of the administration of methotrexate | ii)—Cycles 2 to 15

According to I. T. Magrath et al. (1984) also.

|  | Dose | Route | Days |
| --- | --- | --- | --- |
| 2-quinolone | 200–2000 mg/m²/day or 5–50 mg/kg/day infusion for 1 h | i.v. | $D_1$–$D_3$ $D_{10}$–$D_{11}$ |
| cytarabine | 45 mg/m² | intrathecal | $D_1, D_2$ (cycles 2 and 3) $D_1$ (cycles 4 and 6) |
| cyclophosphamide | 1200 mg/m² bolus | i.v. | $D_1$ |
| doxorubicin | 40 mg/m² bolus | i.v. | $D_1$ |
| vincristine | 1.4 mg/m² bolus (max: 2 mg) | i.v. | $D_1$ |
| methotrexate | 12.5 mg/m² (max: 12.5 mg) | intrathecal | $D_3, D_{10}$ (cycles 2 and 3) $D_{10}$ (cycles 4, 5, 6) |
| methotrexate | 300 mg/m² infusion for 1 hour and then 60 mg/m² continuous infusion for 41 hours | i.v. | $D_{10}, D_{11}$ (cycles 2 and 6) $D_{14}, D_{15}$ (cycles 7–15) |
| leucovorin | 15 mg/m² bolus qid (8 consecutive doses) | i.v. | start at the 42nd hour of the treatment with methotrexate | the cure comprising 14 cycles, at a rate of 1 cycle every 28 days.

3.4 Waldenström's Macroglobulinaemia
3.4.1 CVP Protocol according to the CVP protocol described by M. A. Dimopoulous et al. (Blood 1994; 83: 1452–1459) and C. S. Portlock et al. (Blood 1976; 47: 747–756):

|  | Dose | Route | Days |
| --- | --- | --- | --- |
| 2-quinolone | 200–2000 mg/m²/day or 5–50 mg/kg/day infusion for 1 h | i.v. | $D_1$–$D_5$ |

|  | Dose | Route | Days |
| --- | --- | --- | --- |
| cyclophosphamide (C) | 300–400 mg/m²/day | oral | $D_1$–$D_5$ |
| vincristine (V) | 1.4 mg/m²/day bolus (max: 2 mg) | i.v. | $D_1$ |
| prednisone (P) | 100 mg/m²/day | oral | $D_1$–$D_5$ | the cure being continued indefinitely (1 cycle every 21 days).

3.4.2 Fludarabine-CdA Protocol

According to H. M. Kantarjian et al. (Blood 1990; 75: 1928–1931) and M. A. Dinopoulous et al. (Ann. Intern. Med. 1993; 118: 195–198):

|  | Dose | Route | Days |
| --- | --- | --- | --- |
| 2-quinolone | 200–2000 mg/m²/day or 5–50 mg/kg/day infusion for 1 h | i.v. | $D_1$–$D_5$ |
| fludarabine | 25–30 mg/m² infusion for 0.5 hour | i.v. | $D_1$–$D_5$ |
| or |  |  |  |
| 2-quinolone | 200–2000 mg/m²/day or 5–50 mg/kg/day infusion for 1 h | i.v. | $D_1$–$D_7$ |
| cladribine (CdA) | 0.09 mg/m²/day continuous infusion | i.v. | $D_1$–$D_7$ | the cure comprising 6 to 12 cycles with an interval of 28 days in the case of fludarabine and 2 cycles with an interval of 28 days also in the case of cladribine.

3.5 Multiple Myeloma
3.5.1 MP Protocol

According to R. Alexanian et al. (JAMA 1969; 208: 1680–1685), A. Belch et al. (Br. J. Cancer 1988; 57: 94–99) and F. Mandelli et al. (N. Engl. J. med. 1990; 322: 1430–1434):

|  | Dose | Route | Days |
| --- | --- | --- | --- |
| 2-quinolone | 200–2000 mg/m²/day or 5–50 mg/kg/day infusion for 1 h | i.v. | $D_1$–$D_5$ |
| melphalan (M) | 0.25 mg/kg/day | oral | $D_1$–$D_4$ |
| prednisone (P) | 100 mg/day | oral | $D_1$–$D_4$ |
| or |  |  |  |
| 2-quinolone | 200–2000 mg/m²/day or 5–50 mg/kg/day infusion for 1 h | i.v. | $D_1$–$D_5$ |
| melphalan (M) | 9 mg/m²/day | oral | $D_1$–$D_4$ |
| prednisone (P) | 100 mg/day | oral | $D_1$–$D_4$ | the cure comprising at least 12 cycles, at a rate of 1 cycle every 4 to 6 weeks.

3.5.2 VAD Protocol

According to B. Barlogie et al. (N. Engl. J. Med. 1984; 310: 1353–1356):

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| vincristine (V) | 0.4 mg/day continuous 24-hour infusion | i.v. | $D_1$–$D_4$ |
| doxorubicin (A) | 9 mg/m$^2$/day continuous 24-hour infusion | i.v. | $D_1$–$D_4$ |
| dexamethasone (D) | 40 mg/day | i.v. | $D_1$–$D_4$, $D_9$–$D_{12}$, $D_{17}$–$D_{20}$ |

3.5.3 MP-interferon α Protocol according to O. Osterborg et al. (Blood 1993; 81: 1428–1434):

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| melphalan (M) | 0.25 mg/kg/day | oral | $D_1$–$D_4$ |
| prednisone (P) | 2 mg/kg/day | oral | $D_1$–$D_4$ |
| interferon-alpha | 7 MU/kg/day | s.c. | $D_1$–$D_5$ and $D_{22}$–$D_{26}$ | the cure comprising the indefinite repetition of this cycle, at a rate of 1 cycle every 42 days.

3.5.4 VCAP or VBAP Protocol

According to S. E. Salmon et al. (J. Clin. Oncol. 1983; 1: 453–461):

VCAP protocol:

|  | Dose | Route | Days |
|---|---|---|---|
| 2-quinolone | 200–2000 mg/m$^2$/day or 5–50 mg/kg/day infusion for 1 h | i.v. | $D_1$–$D_5$ |
| vincristine (V) | 1 mg/m$^2$ bolus (max: 1.5 mg) | i.v. | $D_1$ |
| doxorubicin (A) | 30 mg/m$^2$ bolus | i.v. | $D_1$ |
| prednisone (P) | 60 mg/m$^2$/day | oral | $D_1$–$D_4$ |
| cyclophosphamide (C) | 125 mg/m$^2$ infusion for 1 hour | oral | $D_1$–$D_4$ |

VBAP protocol: the cyclophosphamide is replaced with carmustine (BCNU), the remainder being identical:

|  | Dose | Route | Days |
|---|---|---|---|
| carmustine | 30 mg/m$^2$ infusion for 1 hour | i.v. | $D_1$ |

C. TUMORS IN CHILDREN—Pediatric oncology

The isoflavones can also be incorporated into polychemotherapy protocols for treating pediatric tumors in order to improve the antitumor efficacy while at the same time reducing the severity of the side effects by virtue of the action on the recruitment and mobilization of the clonogenic cells and by virtue of the possibility of reducing the active doses.

1/ Ewing's Sarcoma/primitive Neuroectodermal Tumor

The 2-quinolones may be introduced into the VCR-Doxo-CY-Ifos-Mesna-E protocol (E. D. Berger et al., J. Clin. Oncol. 1990; 8: 1514–1524; W. H. Meyer et al., J. Clin. Oncol. 1992; 10: 1737–1742):

|  | Dose | Route | Days |
|---|---|---|---|
| 2-quinolone | 100–200 mg/m$^2$/day or 2–50 mg/kg/day infusion for 1 h | i.v. | $D_1$–$D_5$ and $D_{22}$–$D_{27}$ and $D_{43}$–$D_{48}$ and $D_{63}$–$D_{66}$ |
| vincristine | 2 mg/m$^2$ bolus (maximum dose = 2 mg) | i.v. | $D_1$, $D_8$, $D_{15}$, $D_{43}$ |
| doxorubicin | 30 mg/m$^2$/day in infusion for 24 hours | i.v. | $D_1$–$D_3$, $D_{43}$–$D_{45}$ |
| cyclophosphamide | 2.2 g/m$^2$ in infusion for 0.5 hour | i.v. | $D_1$, $D_{43}$ |
| ifosfamide | 1800 mg/m$^2$/day in infusion for 1 hour | i.v. | $D_{22}$–$D_{26}$ $D_{63}$–$D_{67}$ |
| mesna | 360 mg/m$^2$ in infusion for 15 minutes at a rate of 5 doses every 3 hours | i.v. | administered with cyclophosphamide and ifosfamide |
| etoposide | 100 mg/m$^2$ in infusion for 1 hour | i.v. | $D_{22}$–$D_{26}$ $D_{63}$–$D_{67}$ | the cure comprises 6 to 10 of these cycles depending on the initial severity of the sarcoma and the amplitude of the response.

2/ Acute Pediatric Lymphoblast Leukemia

2.1. Induction Chemotherapy (Days $D_1$–$D_{30}$)

The 2-quinolones may be added to the recommended protocols (P. S. Gaynon et al., J. Clin. Oncol., 1993, 11, 2234–2242; J. Pullen et al., J. Clin. Oncol. 1993; 11: 2234–2242; J. Pullen et al., J. Clin. Oncol. 1993; 11: 839–849; V. J. Land et al., J. Clin. Oncol. 1994; 12: 1939–1945):

|  | Dose | Route | Days |
|---|---|---|---|
| 2-quinolone | 100–200 mg/m$^2$/day or 2–50 mg/kg/day infusion for 1 h | i.v. | $D_1$–$D_5$, $D_8$–$D_{11}$, $D_{15}$–$D_{18}$, $D_{22}$–$D_{27}$ |
| vincristine | 1.5 mg/m$^2$ bolus (maximum dose ≈ 2 mg) | i.v. | $D_1$, $D_8$, $D_{15}$, $D_{22}$ |
| L-asparaginase | 6000 IU/m$^2$ | i.m. | 3 times/week for 3 weeks |
| prednisone | 60 mg/m$^2$ in 3 doses/day | oral | $D_1$ to $D_{28}$ |
| daunorubicin | 25 mg/m$^2$/day in infusion for 15 minutes | i.v. | $D_1$, $D_8$, $D_{15}$ and $D_{22}$ |
| methotrexate | depending on the age | intrathecal | $D_{15}$, $D_{28}$ |
| cytarabine | depending on the age | intrathecal | $D_1$ | depending on the result of the bone marrow examination, passage to the consolidation phase takes place on day $D_{28}$ of the treatment protocol.

2.2. Consolidation/maintenance Chemotherapy

The 2-quinolones may be introduced into the maintenance protocol (P. S. Gaynon et al., J. Clin. Oncol., 1993, 11, 2234–2242; J. Pullen et al., J. Clin. Oncol. 1993; 11: 839–849; V. J. Land et al., J. Clin. Oncol. 1994; 12: 1939–1945) according to the following scheme:

| | Dose | Route | Days |
|---|---|---|---|
| 2-quinolone | 100–200 mg/m²/day or 2–50 mg/kg/day infusion for 1 h | i.v. | $D_1$–$D_5$, $D_{15}$–$D_{20}$ and $D_{94}$–$D_{99}$, $D_{101}$–$D_{106}$ $D_{108}$–$D_{113}$, $D_{122}$–$D_{127}$ |
| cyclophos-phamide | 1000 mg/m² in infusion for 0.5 hour | i.v. | $D_1$, $D_{15}$, $D_{122}$ |
| L-asparaginase | 6000 U/m² | i.m. | 3 times/week between $D_{97}$ and $D_{122}$ |
| cytarabine | 75 mg/m²/day in infusion for 15 minutes | i.v./s.c. | a sequence of 4 days starting $D_2$, $D_9$, $D_{16}$, $D_{23}$, $D_{123}$, $D_1$ |
| doxorubicin | 25 mg/m²/day in infusion for 15 minutes | i.v. | $D_{94}$, $D_{101}$, $D_{108}$ |
| mercaptopurine | 60 mg/m²/day | oral | $D_1$–$D_{93}$, $D_{143}$ to the end of the treatment |
| methotrexate | 20 mg/m²/day | oral | once/week between $D_{36}$ and $D_{72}$ and between $D_{143}$ and the end of the treatment |
| prednisone | 40 mg/m²/day (divided into 3 doses/day) | oral | 5 consecutive days per month between $D_{143}$ and the end of the treatment |
| thioguanine | 60 mg/m²/day | oral | $D_{122}$–$D_{135}$ |
| vincristine | 1.5 mg/m² bolus (maximum dose = 2 mg) | i.v. | $D_{94}$, $D_{101}$, $D_{108}$, then once/month between $D_{143}$ and the end of the treatment |
| methotrexate | depending on the age | intra-thecal | $D_1$, $D_8$, $D_{15}$, $D_{22}$, $D_{123}$, $D_{130}$ then once/3 months between $D_{143}$ and the end of the treatment |

3/ Acute Pediatric Myeloid Leukemia

The 2-quinolones are added to the induction and consolidation/maintenance protocols according to the following schemes:

3.1. Induction Chemotherapy

According to Y. Ravindranath et al., J. Clin. Oncol. 1991; 9: 572–580; M. E. Nesbit et al., J. Clin. Oncol. 1994; 12: 127–135; R. J. Wells et al., J. Clin. Oncol. 1994; 12: 2367–2377):

| | Dose | Route | Days |
|---|---|---|---|
| 2-quinolone | 100–200 mg/m²/day or 2–50 mg/kg/day infusion for 1 hour | i.v. | $D_1$–$D_5$, $D_{10}$–$D_{13}$ |
| cytarabine | depending on the age | intra-thecal | $D_1$ |
| daunorubicin | 20 mg/m²/day in infusion for 24 hours | i.v. | $D_1$–$D_4$, $D_{10}$–$D_{13}$ |
| cytarabine | 200 mg/m²/day in infusion for 24 hours | i.v. | $D_1$–$D_4$, $D_{10}$–$D_{13}$ |
| thioguanine | 100 mg/m²/day divided into 2 doses/day | oral | $D_1$–$D_4$, $D_{10}$–$D_{13}$ |
| etoposide | 100 mg/m²/day in infusion for 24 hours | i.v. | $D_1$–$D_4$, $D_{10}$–$D_{13}$ |
| dexamethasone | 6 mg/m² divided into 3 doses/day | i.v./oral | $D_1$–$D_4$, $D_{10}$–$D_{13}$ | this cycle being repeated from $D_{28}$.

3.2. Consolidation/maintenance Chemotherapy

According to Y. Ravindranath et al., J. Clin. Oncol. 1991; 9: 572–580; M. E. Nesbit et al., J. Clin. Oncol. 1994; 12: 127–135; R. J. Wells et al., J. Clin. Oncol. 1994; 12: 2367–2377):

| | Dose | Route | Days |
|---|---|---|---|
| cytarabine | depending on the age | intra-thecal | $D_1$, $D_{28}$, $D_{56}$ |
| 2-quinolone | 100–200 mg/m²/day or 2–50 mg/kg/day infusion for 1 hour | i.v. | $D_1$–$D_5$, $D_8$–$D_{13}$, $D_{28}$–$D_{33}$, $D_{56}$–$D_{61}$ $D_{89}$–$D_{94}$ |
| cytarabine | 3000 mg/m² in infusion for 3 hours every 12 hours | i.v. | $D_1$–$D_2$, and $D_8$–$D_9$ |
| L-asparaginase | 6000 IU/m² 3 hours after cytarabine | i.m. | $D_2$, $D_9$ |
| vincristine | 1.5 mg/m² bolus (maximum dose = 2 mg) | i.v. | $D_{28}$, $D_{56}$ |
| thioguanine | 75 mg/m²/day | oral | $D_{28}$–$D_{84}$ |
| cytarabine | 75 mg/m²/day bolus | i.v. | $D_{28}$–$D_{31}$, $D_{56}$–$D_{59}$ |
| cyclophos-phamide | 75 mg/m²/day in infusion for 0.5 hour | i.v. | $D_{28}$–$D_{31}$, $D_{56}$–$D_{59}$ |
| cytarabine | 25 mg/m²/day bolus | sc/i.v. | $D_{89}$–$D_{93}$ |
| thioguanine | 50 mg/m²/day | oral | $D_{89}$–$D_{93}$ |
| etoposide | 100 mg/m²/day in infusion for 1 hour | i.v. | $D_{89}$, $D_{92}$ |
| dexamethasone | 2 mg/m²/day | oral | $D_{89}$–$D_{92}$ |
| daunorubicin | 30 mg/m² in infusion for 15 minutes | i.v. | $D_{89}$ |

4/ Pediatric Hodgkin's Disease

The 2-quinolones may be added to the MOPP-ABVD protocol according to E. A. Gehan et al. (Cancer 1990; 65: 1429–1437), S. P. Hunger et al. (J. Clin. Oncol. 1994; 12: 2160–2166) and M. M. Hudson et al. (J. Clin. Oncol. 1993; 11: 100–108):

| | Dose | Route | Days |
|---|---|---|---|
| 2-quinolone | 100–200 mg/m²/day or 2–50 mg/kg/day infusion for 1 hour | i.v. | $D_1$–$D_5$ and $D_8$–$D_{12}$ |

-continued

| | Dose | Route | Days |
|---|---|---|---|
| mechlorethamine (M) | 6 mg/m$^2$ bolus | i.v. | $D_1$, $D_8$ |
| vincristine (O) | 1.5 mg/m$^2$ bolus (maximum 2 mg) | i.v. | $D_1$, $D_8$ |
| procarbazine (P) | 100 mg/m$^2$/day | oral | $D_1$–$D_{14}$ |
| prednisone (P) | 40 mg/m$^2$/day (divided into 3 doses/d) | oral | $D_1$–$D_{14}$ |
| doxorubicin (A) | 25 mg/m$^2$/day in infusion for 15 minutes | i.v. | $D_{29}$, $D_{43}$ |
| bleomycin (B) | 10 U/m$^2$ in infusion for 15 minutes | i.v. | $D_{29}$, $D_{43}$ |
| vinblastine (V) | 6 mg/m$^2$ bolus (maximum 2 mg) | i.v. | $D_{29}$, $D_{43}$ |
| dacarbazine (D) | .375 mg/m$^2$ in infusion for 15 minutes | i.v. | $D_{29}$, $D_{43}$ | this cycle should be repeated 6 times at a rate of 1 cycle every 8 weeks, the cure comprising 6 cycles.

If an autologous bone marrow transplant (auto-graft) is prescribed, the CVB protocol described by R. Chopra et al. (Blood 1993; 81: 1137–1145), C. Wheeler et al. (J. Clin. Oncol. 1990; 8: 648–656) and R. J. Jones et al. (J. Clin. Oncol. 1990, 8, 527–537) may be used according to the following scheme (the allograft taking place on day $D_0$):

| | Dose | Route | Days |
|---|---|---|---|
| 2-quinolone | 100–200 mg/m$^2$/day or 2–50 mg/kg/day infusion for 1 hour | i.v. | $D_{-7}$, $D_{-1}$ |
| cyclophosphamide | 1800 mg/m$^2$/day in 2 infusions for 1 hour | i.v. | $D_{-7}$, $D_{-6}$ $D_{-5}$, $D_{-4}$ |
| carmustine (BCNU) | 112 mg/m$^2$/day in infusion for 0.5 hour | i.v. | $D_{-7}$, $D_{-6}$ $D_{-5}$, $D_{-4}$ |
| etoposide | 500 mg/m$^2$/day in 2 infusions for 1 hour | i.v. | $D_{-7}$, $D_{-6}$ $D_{-5}$, $D_{-4}$ |

5/ Pediatric Lymphoblast Lymphoma

The compounds claimed may also be combined with the induction chemotherapy protocols (A. T. Meadows et al., J. Clin. Oncol. 1989; 7: 92–99-C. Patte et al., Med. Ped. Oncol. 1992; 20: 105–113 and A. Reiter et al., J. Clin. Oncol. 1995; 13: 359–372) and the maintenance chemotherapy protocols:

5.1 Induction Chemotherapy

| | Dose | Route | Days |
|---|---|---|---|
| 2-quinolone | 100–200 mg/m$^2$/day or 2–50 mg/kg/day infusion for 1 hour | i.v. | $D_1$–$D_5$, $D_{17}$–$D_{22}$, $D_{24}$–$D_{29}$ |
| cyclophosphamide | 1200 mg/m$^2$ in infusion for 0.5 hour | i.v. | $D_1$ |
| cytarabine | depending on the age | intra-thecal | $D_1$ |
| vincristine | 1.5 mg/m$^2$ bolus (maximum 2 mg) | i.v. | $D_3$, $D_{10}$, $D_{17}$, $D_{24}$ |
| prednisone | 60 mg/m$^2$/day divided into 3 doses/day | oral | $D_3$–$D_{28}$ |
| daunorubicin | 60 mg/m$^2$ in infusion for 15 minutes | i.v. | $D_{17}$ |
| L-asparaginase | 6000 U/m$^2$/day in infusion for 15 minutes | im | $D_{17}$–$D_{35}$ 3 times/week |
| methotrexate | depending on the age | intra-thecal | $D_{17}$, $D_{31}$ |

5.2 Maintenance Chemotherapy according to the following scheme

| | Dose | Route | Days |
|---|---|---|---|
| 2-quinolone | 100–200 mg/m$^2$/day or 2–50 mg/kg/day infusion for 1 hour | i.v. | $D_1$–$D_5$, $D_{15}$–$D_{20}$, $D_{29}$–$D_{34}$ |
| cyclophosphamide | 1000 mg/m$^2$ in infusion for 0.5 hour | i.v. | $D_1$ |
| vincristine | 1.5 mg/m$^2$ bolus (maximum 2 mg) | oral | $D_1$, $D_5$ (from cycles 2 to 10) |
| methotrexate | 300 mg/m$^2$/day (60% in infusion for 15 minutes and 40% in infusion for 4 hours) | i.v. | $D_{15}$ |
| leucovorin | 10 mg/m$^2$/every 4 h | oral | $D_{16}$ |
| daunorubicin | 30 mg/m$^2$ in infusion for 0.5 hour | i.v. | $D_{29}$ |
| methotrexate | depending on the age | intra-thecal | $D_1$, $D_8$, $D_{15}$ (cycle 1) and then once/month (cycles 2 to 10) | the cure comprising 10 cycles.

6/ Pediatric Neuroblastoma

The recommended polychemotherapy protocol Doxo-E-Cy-Pt is adapted from R. P. Castleberry et al. (J. Clin. Oncol. 1992; 10: 1299–1304), A. Garaventa et al. (J. Clin. Oncol. 1993; 11: 1770–1779) and D. C. West et al. (J. Clin. Oncol. 1992; 11: 84–90):

| | Dose | Route | Days |
|---|---|---|---|
| 2-quinolone | 100–200 mg/m$^2$/day or 2–50 mg/kg/day infusion for 1 hour | i.v. | $D_1$–$D_5$, $D_{28}$–$D_{35}$, $D_{58}$–$D_{65}$ |
| doxorubicin | 25 mg/m$^2$/day in infusion for 15 minutes | i.v. | $D_2$, $D_{30}$, $D_{58}$ |
| etoposide | 100 mg/m$^2$ in infusion for 1 hour | oral/naso-gastric | $D_2$, $D_5$, $D_{30}$, $D_{33}$, $D_{58}$, $D_{61}$ |

-continued

| | Dose | Route | Days |
|---|---|---|---|
| cyclophos-phamide | 1000 mg/m² in infusion for 0.5 hour | i.v. | $D_3$, $D_4$, $D_{31}$, $D_{32}$, $D_{59}$, $D_{60}$ |
| cisplatin | 60 mg/m² in infusion for 6 hours | i.v. | $D_1$, $D_{28}$, $D_{56}$ | the evaluation of the therapeutic response is carried out after 9 weeks in order to determine the approach: surgical resection, radiotherapy or new chemotherapy.

7/ Pediatric Osteosarcoma

The 2-quinolones may be added to the Doxo-Pt-Mtx-Lcv protocol as described by M. Hudson et al. (J. Clin. Oncol. 1990; 8: 1988–1997), P. A. Meyers (J. Clin. Oncol. 1992; 10: 5–15) and V. H. C. Bramwell et al. (J. Clin. Oncol. 1992; 10: 1579–1591):

| | Dose | Route | Days |
|---|---|---|---|
| 2-quinolone | 100–200 mg/m²/day or 2–50 mg/kg/day infusion for 1 hour | i.v. | $D_1$–$D_5$, $D_{21}$–$D_{26}$, $D_{28}$–$D_{33}$ |
| doxorubicin | 25 mg/m²/day in infusion for 24 hours | i.v. | $D_1$–$D_3$ |
| cisplatin | 120 mg/m² in infusion for 6 hours | i.v. | $D_1$ |
| methotrexate | 12 mg/m²/day in infusion for 1 hour | i.v. | $D_{21}$, $D_{28}$ |
| leucovorin | 100 mg/m² every 6 hours | oral | $D_{22}$, $D_{29}$ |

8/ Pediatric Rhabdomyosarcoma

The Vcr-Dact-CY-Mesna protocol (H. Maurer et al., Cancer 1993; 71: 1904–1922 and L. R. Mandell et al., Oncology 1993; 7: 71–83) may include the i.v. infusion of the compounds claimed according to the following scheme:

| | Dose | Route | Days |
|---|---|---|---|
| 2-quinolone | 100–200 mg/m²/day or 2–50 mg/kg/day infusion for 1 hour | i.v. | $D_1$–$D_5$, $D_8$–$D_{12}$, $D_{22}$–$D_{27}$, $D_{43}$–$D_{47}$ |
| vincristine | 1.5 mg/m² bolus (max. 2 mg) | i.v. | $D_1$, $D_8$, $D_{15}$, $D_{22}$, $D_{29}$, $D_{36}$, $D_{43}$, $D_{50}$ and $D_{57}$ |
| dactinomycin | 0.015 mg/kg bolus (max. daily dose: 0.5 mg) | i.v. | $D_1$–$D_5$, $D_{22}$–$D_{27}$, $D_{43}$–$D_{47}$ |
| cyclophos-phamide | 2.2 g/m² in infusion for 1 hour | i.v. | $D_1$, $D_{22}$, $D_{43}$ |
| mesna | 360 mg/m² in infusion for 1 hour every 3 hours for 5 doses | i.v. | $D_1$, $D_{22}$, $D_{43}$ |

At the end of the 9th week of treatment, the efficacy should be evaluated to decide the follow-up treatment (surgery, radiotherapy, continuation of the chemotherapy).

9/ Wilms' Tumor in Children

In the Vcr-Dact protocol as described by G. J. D'Angio et al. (Cancer, 1989; 64: 349–360) and D. M. Green et al. (J. Clin. Oncol. 1993; 11: 91–95):

| | Dose | Route | Days |
|---|---|---|---|
| 2-quinolone | 100–200 mg/m²/day or 2–50 mg/kg/day infusion for 1 hour | i.v. | $D_1$–$D_5$, $D_8$–$D_{12}$ and then every week |
| vincristine | 2 mg/m² bolus (max. dose: 2 mg) | i.v. | $D_7$ and then every week |
| dactinomycin | 0.045 mg/kg bolus (P ≤ 30 kg) 1.35 mg/m² (P > 30 kg) (max. dose: 3 mg) | i.v. | $D_1$ and then every 3 weeks | this protocol being started after the surgical resection.

In the event of autologous bone marrow transplants 10 (auto-graft) according to A. Garaventar et al. (Med. Pediatr. Oncol. 1994; 22: 11–14), the E-Thio-Cy protocol may be modified as follows:

| | Dose | Route | Days |
|---|---|---|---|
| 2-quinolone | 100–200 mg/m²/day or 2–50 mg/kg/day infusion for 1 hour | i.v. | $D_{-8}$–$D_{-1}$ |
| etoposide | 1800 mg/m² (infusion for 24 hours) | i.v. | $D_{-8}$ |
| thiotepa | 300 mg/m²/day in infusion for 2 hours | i.v. | $D_{-7}$, $D_{-6}$, $D_{-5}$ |
| cyclophosphamide | 50 mg/kg/day in infusion for 1 hour | i.v. | $D_{-4}$, $D_{-3}$, $D_{-2}$, $D_{-1}$ |

The bone marrow transplant taking place on day $D_0$.

What is claimed is:

1. A method for treating cancer comprising the administration of (a) at least one antitumor agent chosen from cytotoxic agents and (b) an effective amount of a compound of formula (I) or (Ia):

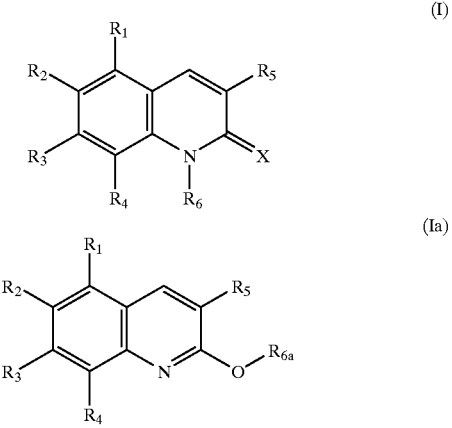

in which:
X is chosen from =O, =S and =N—NH—$R_7$, $R_7$ being a phenyl or pyridyl group, $R_1$, $R_2$, $R_3$, and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$, or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —$OCOR_8$, a phenyl ($C_1$–$C_4$ alkoxy) group, a group —O—$SO_2$—$R'_8$, $R'_8$ being a $C_1$–$C_4$ alkyl group or a $CF_3$ group, and a group derived from a saccharide, $R_6$ is chosen from H, a $C_1$–$C_4$ alkyl group, a group —CO—$R_9$ and a group —A—$R_{10}$, $R_{6a}$ is chosen from a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —$COOR_{11}$, —$CONR_{12}R_{13}$, a group —$NR_{14}R_{15}$ and a group —$COR_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl ($C_1$–$C_4$ alkyl) group, $R_4$ and $R_6$ together also possible forming a —CO—$CH_2$—$CH_2$— group.

2. Method according to claim 1, in which the compound is a compound of formula (I) in which:

$R_1$ is a $C_1$–$C_4$ alkoxy group $R_2$ is a hydrogen atom $R_3$ is a $C_1$–$C_4$ alkoxy group $R_4$ is a hydrogen atom.

3. Method according to claim 2, in which the compound is a compound of formula (I) in which:

$R_5$ is a 4-($C_1$–$C_4$ alkoxy) phenyl group.

4. Method according to claim 3, in which:

$R_1$ is a methoxy group, $R_3$ is a methoxy group, and $R_5$ is a 4-methoxyphenyl group.

5. Method according to claim 4, in which the compound is 5,7-dimethoxy-3-(4-methoxyphenyl)-1,2-dihydro-2-quinolinone.

6. Method according to claim 4, in which the compound is 3-[5,7-dimethoxy-3-(4-methoxyphenyl)-2-oxo-1,2-dihydro-1-quinolinyl]propanenitrile.

7. Method according to claim 4, in which the compound is 1-[2-(1H-1,2,3,4-tetrazol-5-yl)ethyl]-5,7-dimethoxy-3(4-methoxyphenyl)-1,2-dihydro-2-quinolinone.

8. Method according to claim 4, in which the compound is N,N-diethyl-3-[5,7-dimethoxy-3-(4-methoxyphenyl)-2-oxo-1,2-dihydro-1-quinolinyl]propanamide.

9. Pharmaceutical composition having activity on the proliferation of clonogenic cells in tumors and which comprises an effective amount of a compound of formula (I) or (Ia):

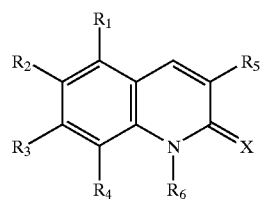

(I)

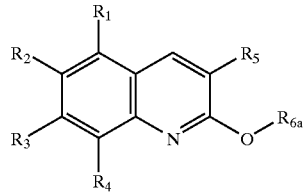

(Ia)

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —$OCOR_8$, a phenyl ($C_1$–$C_4$ alkoxy) group, a group —O—$SO_2$—$R'_8$, $R'_8$ being a $C_1$–$C_4$ alkyl group or a $CF_3$ group, and a group derived from a saccharide, $R_6$ is chosen from H, a $C_1$–$C_4$ alkyl group, a group —CO—$R_9$ and a group —A—$R_{10}$, $R_{6a}$ is chosen from a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —$COOR_{11}$, —$CONR_{12}R_{13}$, a group —$NR_{14}R_{15}$, and a group —$COR_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl ($C_1$–$C_4$ alkyl) group, $R_4$ and $R_6$ together also possibly forming a —CO—$CH_2$—$CH_2$— group.

10. Composition according to claim 9, in which the compound is a compound of formula (I) in which:

$R_1$ is a $C_1$–$C_4$ alkoxy group $R_2$ is a hydrogen atom $R_3$ is a $C_1$–$C_4$ alkoxy group $R_4$ is a hydrogen atom.

11. Composition according to claim 10, in which the compound is a compound of formula (I) in which:

$R_5$ is a 4-($C_1$–$C_4$ alkoxy) phenyl group.

12. Composition according to claim 11, in which the compound is a compound of formula (I), $R_1$ is a methoxy group, $R_3$ is a methoxy group and $R_5$ is a 4-methoxyphenyl group.

13. Composition according to claim 12, in which the compound is 5,7-dimethoxy-3-(4-methoxyphenyl)-1,2-dihydro-2-quinolinone.

14. Composition according to claim 12, in which the compound is 3-[5,7-dimethoxy-3-(4-methoxyphenyl)-2-oxo-1,2-dihydro-1-quinolinyl]propanenitrile.

15. Composition according to claim 12, in which the compound is 1-[2-(1H-1,2,3,4-tetrazol-5-yl)ethyl]-5,7-dimethoxy-3-(4-methoxyphenyl)-1,2-dihydro-2-quinolinone.

16. Composition according to claim 12, in which the compound is N,N-diethyl-3-[5,7-dimethoxy-3-(4-methoxyphenyl)-2-oxo-1,2-dihydro-1-quinolinyl]propanamide.

17. Compound of formula (I) or (Ia):

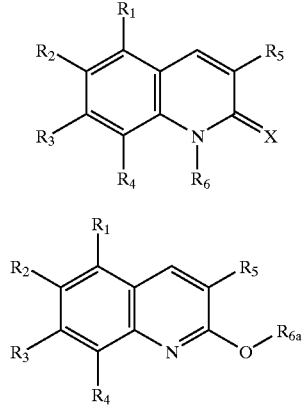

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCOR$_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group substituted 1 to 3 times with groups chosen from H, OH, a $C_1$–$C_4$ alkoxy group, a group —OCOR$_8$, a phenyl ($C_1$–$C_4$ alkoxy) group, a group —O—SO$_2$R'$_8$, R'$_8$ being a $C_1$–$C_4$ alkyl group or a CF$_3$ group, and a group derived from a saccharide, $R_6$ is chosen from a $C_1$–$C_4$ alkyl group, a group —CO—$R_9$ and a group —A—$R_{10}$, $R_{6a}$ is chosen from a group —CO—$R_9$ and group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hereto atoms chosen from oxygen, sulfur and nitrogen, the CN group, a group —COO4$_{11}$, —CONR$_{12}$R$_{13}$, a group —NR$_{14}$R$_{15}$ and a group —COR$_{16}$, $R_{11}$, $R_{12}$) $R_{13}$, $R_{14}$, $R_{15}$ and $R_{16}$ being chosen independently from a hydrogen atom, a $C_1$–$C_4$ alkyl group and a phenyl ($C_1$–$C_4$ alkyl) group, $R_4$ and $R_6$ together also possibly forming a —CO—CH$_2$—CH$_2$— group.

18. Compound according to claim 17, which is 3-[5,7-dimethoxy-3-(4-methoxyphenyl)-2-oxo-1,2-dihydro-1-quinolinyl]propanenitrile.

19. Compound according to claim 17, which is 1-[2-(1H-1,2,3,4-tetrazol-5-yl)ethyl]-5,7-dimethoxy-3-(4-methoxyphenyl)-1,2-dihydro-2-quinolinone.

20. Compound according to claim 17, which is N,N-diethyl-3-[5,7-dimethoxy-3-(4-methoxyphenyl)-2-oxo-1,2-dihydro-1-quinolinyl]propanamide.

21. Compound of formula:

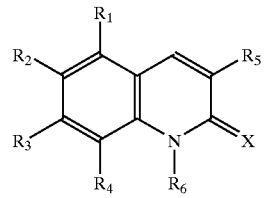

in which:

X is chosen from =O, =S and =N—NH—$R_7$, $R_7$ being a phenyl or pyridyl group, $R_1$, $R_2$, $R_3$ and $R_4$ are chosen, independently of each other, from H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$, alkoxy group, a group —OCOR$_8$, a phenyl ($C_1$–$C_4$ alkoxy) group, a group —O—SO$_2$—R'$_8$, R'$_8$ being a $C_1$–$C_4$ alkyl group or a CF$_3$ group, and a group derived from a saccharide, $R_6$ is chosen from a group —A—$R_{10}$, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —COOR$_{11}$, —CONR$_{12}$R$_{13}$, a group —NR$_{14}$R$_{15}$ and a group —COR$_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl ($C_1$–$C_4$ alkyl) group.

22. Compound of formula:

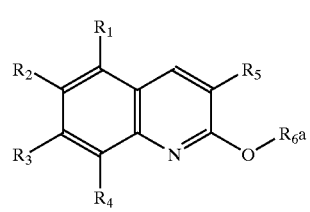

in which:

$R_1$, $R_2$, $R_3$ and $R_4$ are chosen, independently of each other, from, H, OH, a $C_1$–$C_4$ alkyl group, a $C_1$–$C_4$ alkoxy group, a group —OCO—$R_8$, $R_8$ being a $C_1$–$C_4$ alkyl group, and a group derived from a saccharide, at least one of the substituents $R_1$, $R_2$, $R_3$ or $R_4$ being other than H, and $R_2$ and $R_3$ together possibly forming a methylenedioxy group, $R_5$ is a phenyl group or a phenyl group substituted 1 to 3 times with groups chosen from H, OH, a $C_1$–$C_4$ alkoxy group, a group —OCOR$_8$, a phenyl ($C_1$–$C_4$ alkoxy) group, a group —O—SO$_2$—R'$_8$, R'$_8$ being a $C_1$–$C_4$ alkyl group or a CF$_3$ group, and a group derived from a saccharide, $R_{6a}$ is chosen from a group —CO—$R_9$ and a group —A—$R_{10}$, $R_9$ being a $C_1$–$C_4$ alkyl group, A being a $C_1$–$C_4$ alkylene group, $R_{10}$ being chosen from 5- or 6-membered heterocyclic groups containing 1 to 4 hetero atoms chosen from oxygen, sulfur and nitrogen, the CN group, a group —$COOR_{11}$, —$CONR_{12}R_{13}$, a group —$NR_{14}R_{15}$ and a group —$COR_{16}$, $R_{11}$, $R_{12}$, $R_{13}$, $R_{14}$, $R_{15}$ and $R_{16}$ being chosen independently from a hydrogen atom, a $C_1$–$C_4$ alkyl group and a phenyl ($C_1$–$C_4$ alkyl) group.

* * * * *